US009458206B2

(12) United States Patent
Takumi et al.

(10) Patent No.: US 9,458,206 B2
(45) Date of Patent: Oct. 4, 2016

(54) L-AMINO ACID-PRODUCING BACTERIUM AND A METHOD FOR PRODUCING AN L-AMINO ACID

(75) Inventors: Kazuhiro Takumi, Kawasaki (JP); Gen Nonaka, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 1483 days.

(21) Appl. No.: 12/706,032

(22) Filed: Feb. 16, 2010

(65) Prior Publication Data

US 2010/0209977 A1 Aug. 19, 2010

(30) Foreign Application Priority Data

Feb. 16, 2009 (JP) ................................ 2009-032835

(51) Int. Cl.
*C12P 13/24* (2006.01)
*C07K 14/245* (2006.01)

(52) U.S. Cl.
CPC .................................. *C07K 14/245* (2013.01)

(58) Field of Classification Search
USPC ........................................................ 435/107
See application file for complete search history.

(56) References Cited

U.S. PATENT DOCUMENTS

| | | | | |
|---|---|---|---|---|
| 5,827,698 | A | 10/1998 | Kikuchi et al. | |
| 5,972,663 | A | 10/1999 | Winterhalter et al. | |
| 6,218,168 | B1 | 4/2001 | Leinfelder et al. | |
| 8,034,767 | B2 * | 10/2011 | Kutukova et al. | 435/87 |
| 2004/0038352 | A1 | 2/2004 | Maier | |
| 2005/0221453 | A1 | 10/2005 | Takagi et al. | |
| 2008/0076163 | A1 | 3/2008 | Takagi et al. | |
| 2008/0307548 | A1 | 12/2008 | Yamada et al. | |
| 2009/0226983 | A1 | 9/2009 | Nonaka et al. | |
| 2009/0226984 | A1 | 9/2009 | Nonaka et al. | |

FOREIGN PATENT DOCUMENTS

| | | |
|---|---|---|
| EP | 0 643 135 | 3/1995 |
| EP | 0 733 712 | 9/1996 |
| EP | 0 796 912 | 9/1997 |
| EP | 0 837 134 | 4/1998 |
| EP | 1 013 765 | 6/2000 |
| EP | 1 170 376 | 1/2002 |
| EP | 1 253 195 | 10/2002 |
| EP | 1 477 565 | 11/2004 |
| EP | 1650296 | 4/2006 |
| JP | 11-056381 | 3/1999 |
| JP | 11-155571 | 6/1999 |
| JP | 2000-504926 | 4/2000 |
| JP | 2000-189180 | 7/2000 |
| JP | 2003-169668 | 6/2003 |
| JP | 2004-049237 | 2/2004 |
| JP | 2005-245311 | 9/2005 |
| JP | 2005-287333 | 10/2005 |
| WO | WO96/17930 | 6/1996 |
| WO | WO01/53459 | 7/2001 |
| WO | WO2005/010175 | 2/2005 |
| WO | WO2006/013807 | 2/2006 |

OTHER PUBLICATIONS

European Search Report for EP Patent App. No. 10001535.3 (Apr. 29, 2010).

Daβler, T., et al., "Identification of a major facilitator protein from *Escherichia coli* involved in efflux of metabolites of the cysteine pathway," Mol. Microbiol. 2000;36(5):1101-1112.

Kutukova, E. A., et al., "The *yeaS* (*leuE*) gene of *Escherichia coli* encodes an exporter of leucine, and the Lrp protein regulates its expression," FEBS Letters 2005;579:4629-4634.

Wiriyathanawudhiwong, N., et al., "The outer membrane TolC is involved in cysteine tolerance and overproduction in *Escherichia coli*," Appl. Microbiol. Biotechnol. 2009;81:903-913.

U.S. Appl. No. 12/711,299, Nonaka et al., filed Feb. 24, 2010.

U.S. Appl. No. 12/722,094, Nonaka et al., filed Mar. 11, 2010.

* cited by examiner

*Primary Examiner* — Tekchand Saidha

(74) *Attorney, Agent, or Firm* — Shelly Guest Cermak; Cermak Nakajima & McGowan LLP

(57) ABSTRACT

A bacterium belonging to the family Enterobacteriaceae, which has an ability to produce an amino acid such as L-cysteine and has been modified to have specific mutation in the yeas gene, is cultured in a medium, and the L-amino acid is collected from the medium.

15 Claims, 3 Drawing Sheets

```
                                   -35(Pnlp2)                       -10(Pnlp2)
aaaacgtgaggaaatacctggatttttcctggttattttgccgcaggtcagcgtatcgtg
                  -35(Pnlp1)                     -10(Pnlp1)   trancr start
aagatcttttccagtgttcagtagggtgccttgcacggtaattatgtcactggttattaa
                          M   S
ccaatttttcctggggataaatgagc
```

L-AMINO ACID-PRODUCING BACTERIUM AND A METHOD FOR PRODUCING AN L-AMINO ACID

This application claims priority under 35 U.S.C. §119 to Japanese Patent Application No. 2009-032835, filed on Feb. 16, 2009, which is incorporated in their entireties by reference. The Sequence Listing in electronic format filed herewith is also hereby incorporated by reference in its entirety (File Name: 100216T_US-424_Seq_List; File Size: 70 KB; Date Created: Feb. 16, 2010).

BACKGROUND OF THE INVENTION

1. Field of the Invention

The present invention relates to a method for producing an L-amino acid such as L-cysteine. More precisely, the present invention relates to a bacterium suitable for production of an L-amino acid and a method for producing an L-amino acid utilizing such a bacterium. L-Amino acids are used in various fields, for example, as seasonings, food additives, animal feed additives, chemicals, drugs, and so forth.

2. Background Art

L-Amino acids are industrially produced by fermentation using microorganisms belonging to the genus *Brevibacterium, Corynebacterium, Escherichia*, or the like. In such methods, strains are used which are isolated from nature or artificial variants of such strains. Furthermore, microorganism strains can be used which are modified by recombinant DNA techniques so that the activity of a basic L-amino acid biosynthesis enzyme is increased, and so forth (EP 0643135 B, EP 0733712 B, EP 1477565 A, EP 0796912 A, EP 0837134 A, WO01/53459, EP 1170376 A, WO2005/010175, WO96/17930, WO2006/013807).

Furthermore, L-cysteine, for example, is obtained by extraction from substances containing keratin, such as hair, horns, and feathers. L-cysteine can also be obtained by converting the precursor DL-2-aminothiazoline-4-carboxylic acid using a microbial enzyme (Sano, K. et al., Appl. Environ. Microibol., 34, 806-810 (1977)).

Furthermore, L-cysteine has also been produced by fermentation utilizing a bacterium. For example, a method has been disclosed for producing L-cysteine using an *Escherichia* bacterium with a suppressed L-cysteine decomposition system and a serine acetyltransferase (EC 2.3.1.30, henceforth also referred to as "SAT") with attenuated feedback inhibition by L-cysteine is attenuated (Japanese Patent Laid-open (Kokai) No. 11-155571). Furthermore, coryneform bacteria or *Escherichia* bacteria attenuated or deleted activity of cystathionine-β-lyase (Japanese Patent Laid-open (Kokai) No. 11-155571), tryptophanase (Japanese Patent Laid-open No. 2003-169668), or O-acetylserine sulfhydrylase B (Japanese Patent Laid-open No. 2005-245311) are examples of bacteria with an enhanced ability to produce L-cysteine by suppressing the decomposition of L-cysteine. A method for producing L-cysteine by using a bacterium in which L-cysteine metabolism is decontrolled by using a DNA sequence coding for SAT that has a specific mutation for attenuating feedback inhibition by L-cysteine is also known (National Publication of Translated Version in Japan (Kohyo) No. 2000-504926).

Furthermore, it is known that the ydeD gene which encodes the YdeD protein (Dabler et al., Mol. Microbiol., 36, 1101-1112 (2000)), and the yfiK gene which encodes the YfiK protein (Japanese Patent Laid-open No. 2004-49237), participate in secretion of the metabolic products of the cysteine pathway. Techniques are also known for enhancing the L-cysteine-producing ability by increasing expression of the mar-locus, acr-locus, cmr-locus, mex-gene, bmr-gene, or qacA-gene, which encode proteins responsible for secreting toxic substances from cells (U.S. Pat. No. 5,972,663), or emrAB, emrKY, yojIH, acrEF, bcr, or cusA genes (Japanese Patent Laid-open No. 2005-287333).

Moreover, a method has been reported for producing L-cysteine using a bacterium which overexpresses a gene coding for a protein responsible for releasing an antibiotic or a substance toxic to a bacterium directly from a cell (Japanese Patent Laid-open No. 11-56381).

Moreover, it is known that production of L-amino acids by bacteria, not only L-cysteine, can be improved by increasing expression of an L-amino acid secretion protein. It is known that, in coryneform bacteria, L-lysine production is improved by increasing expression of an L-lysine secretion carrier, named LysE (Japanese Patent Laid-open No. 2000-189180). Furthermore, for *Escherichia* bacteria, several membrane proteins are known to be amino acid secretion carriers. For example, it has been reported that, by increasing the copy number of a gene named rhtB, resistance to a high concentration of L-homoserine, L-threonine, L-alanine, L-valine, and L-isoleucine is improved, and the product of this gene is a secretion carrier of these L-amino acids (Japanese Patent Laid-open No. 2000-189180).

The yeaS gene belongs to the family of the aforementioned rhtB gene, the product of which is presumed to be a membrane protein, and it has been reported that, by increasing expression of this gene, resistance to a high concentration of L-threonine, L-homoserine, L-lysine, L-glutamic acid, L-histidine, L-proline, and α-aminobutyric acid is improved as compared to a control strain, and by increasing expression of this gene in an L-amino acid-producing bacterium, production of L-valine, L-isoleucine, L-alanine, L-proline, and L-histidine is improved (EP 1013765 A1).

As described above, the effect of increasing yeaS gene expression on the production of various amino acids has been investigated (Kutukova et al., FEBS Lett., 579, 4629-4634 (2005)). However, mutations of the yeaS gene which improve L-amino acid productivity have not been previously reported.

SUMMARY OF THE INVENTION

Aspects of the present invention include to develop novel techniques for improving the ability of bacteria to produce L-amino acids, and thereby provide an bacterium which is able to produce one or more L-amino acids, and a method for producing an L-amino acid using such a bacterium.

These aspects were achieved by finding that the ability of a bacterium to produce an L-amino acid can be improved by introducing a specific mutation into the yeaS gene.

It is an aspect of the present invention to provide a method for producing an L-amino acid comprising:

a) culturing in a medium a bacterium belonging to the family Enterobacteriaceae, which is able to produce an L-amino acid, and has been modified to have a mutation in the yeaS gene selected from the group consisting of:

(I) replacing the threonine residue at position 28 with an amino acid residue other than threonine in the protein encoded by the yeaS gene, (II) replacing the phenylalanine residue at position 137 with an amino acid residue other than phenylalanine in the protein encoded by the yeaS gene, (III) replacing the leucine residue at position 188 with an amino acid residue other than leucine in the protein encoded by the yeaS gene, and, (IV) combinations thereof; and b) collecting the L-amino acid from the medium, wherein the yeaS gene without said mutation encodes a protein selected from the group consisting of:

(A) a protein comprising the amino acid sequence of SEQ ID NO: 2, and (B) a protein comprising the amino acid sequence of SEQ ID NO: 2, but wherein 1 to 10 amino acid residues are substituted, deleted, inserted or added, and the protein has an activity of improving an ability to produce L-cysteine when overexpressed in the bacterium belonging to the family Enterobacteriaceae as compared to a bacterium in which the protein is not overexpressed.

It is a further aspect of the present invention to provide the method as described above, wherein the yeaS gene without said mutation is selected from the group consisting of:

(a) a DNA comprising the nucleotide sequence of SEQ ID NO: 1, and (b) a DNA which is able to hybridize with a sequence complementary to the nucleotide sequence of SEQ ID NO: 1, or a probe which can be prepared from the nucleotide sequence, under stringent conditions, and wherein said DNA encodes a protein having an activity of improving an ability to produce L-cysteine when overexpressed in the bacterium belonging to the family Enterobacteriaceae as compared to a bacterium in which the protein is not overexpressed.

It is a further aspect of the present invention to provide the method as described above, wherein (i) said amino acid residue other than threonine is asparagine, (ii) said amino acid residue other than phenylalanine is selected from the group consisting of serine, glutamine, alanine, histidine, cysteine, and glycine, and (iii) said amino acid residue other than leucine is glutamine.

It is a further aspect of the present invention to provide the method as described above, wherein said amino acid other than phenylalanine is serine or glutamine.

It is a further aspect of the present invention to provide the method as described above, wherein the L-amino acid is selected from the group consisting of L-cysteine, L-leucine, L-threonine, L-serine, L-methionine, L-histidine, L-valine, L-glutamic acid, L-arginine, L-isoleucine, L-phenylalanine, L-tyro sine, L-tryptophan, and L-proline.

It is a further aspect of the present invention to provide the method as described above, wherein the L-amino acid is L-cysteine.

It is a further aspect of the present invention to provide the method as described above, wherein the bacterium has been further modified to increase activity of an L-cysteine biosynthesis system enzyme.

It is a further aspect of the present invention to provide the method as described above, wherein the L-cysteine biosynthesis system enzyme is serine acetyltransferase.

It is a further aspect of the present invention to provide the method as described above, wherein feedback inhibition of serine acetyltransferase by L-cysteine is reduced.

It is a further aspect of the present invention to provide the method as described above, wherein the bacterium is a *Pantoea* bacterium.

It is a further aspect of the present invention to provide the method as described above, wherein the bacterium is *Pantoea ananatis*.

It is a further aspect of the present invention to provide the method as described above, wherein the bacterium is *Escherichia coli*.

It is a further aspect of the present invention to provide a bacterium belonging to the family Enterobacteriaceae, which is able to produce an L-amino acid, and has been modified to have a mutation in a yeas gene selected from the group consisting of:

(I) replacing the threonine residue at position 28 with an amino acid residue other than threonine in the protein encoded by the yeaS gene, (II) replacing the phenylalanine residue at position 137 with an amino acid residue other than phenylalanine in the protein encoded by the yeaS gene, (III) replacing the leucine residue at position 188 with an amino acid residue other than leucine in the protein encoded by the yeaS gene, and, (IV) combinations thereof; and wherein the yeaS gene without said mutation encodes a protein selected from the group consisting of:

(A) a protein comprising the amino acid sequence of SEQ ID NO: 2, and (B) a protein comprising the amino acid sequence of SEQ ID NO: 2, but wherein 1 to 10 amino acid residues are substituted, deleted, inserted or added, and the protein has an activity of improving the ability to produce L-cysteine when overexpressed in a bacterium belonging to the family Enterobacteriaceae as compared to a bacterium in which the protein is not overexpressed.

It is a further aspect of the present invention to provide the bacterium as described above, wherein the L-amino acid is L-cysteine.

It is a further aspect of the present invention to provide a DNA which encodes a protein selected from the group consisting of:

(A) a protein comprising the amino acid sequence of SEQ ID NO: 2, and (B) a protein comprising the amino acid sequence of SEQ ID NO: 2, but wherein 1 to 10 amino acid residues are substituted, deleted, inserted or added, and the protein has an activity of improving the ability to produce L-cysteine when overexpressed in a bacterium belonging to the family Enterobacteriaceae as compared to a bacterium in which the protein is not overexpressed, wherein the protein has a mutation selected from the group consisting of:

(I) replacing the threonine residue at position 28 with an amino acid residue other than threonine, (II) replacing the phenylalanine residue at position 137 with an amino acid residue other than phenylalanine, and (III) replacing the leucine residue at position 188 with an amino acid residue other than leucine.

According to the present invention, the ability of a bacterium belonging to the family Enterobacteriaceae to produce an L-amino acid can be improved. Moreover, by using the bacterium of the present invention, L-amino acids can be efficiently produced by fermentation.

Moreover, the present invention also provides a novel gene coding for a protein having an activity of improving the ability of a host cell to produce L-amino acids when overexpressed as compared with a bacterium in which the protein is not overexpressed.

DETAILED DESCRIPTION OF EXEMPLARY EMBODIMENTS

<1> Bacterium

Figures 1, 2:
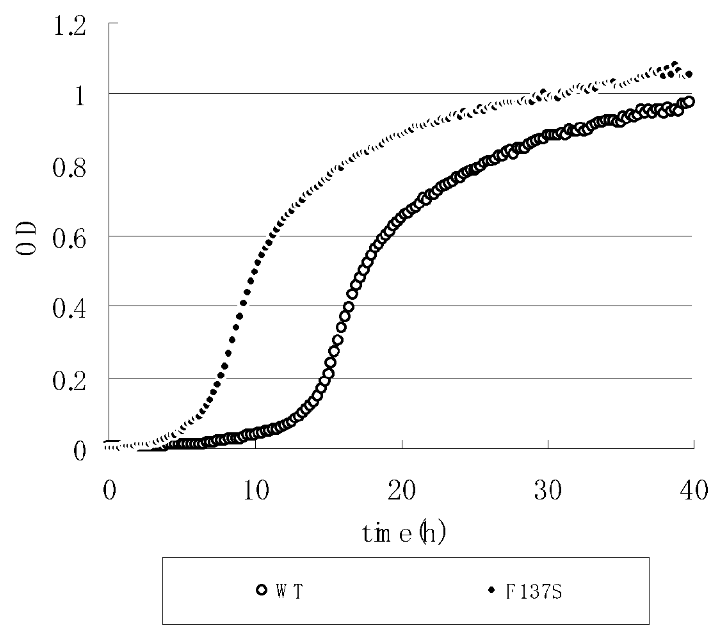
FIG. 1 shows the sequence of the promoter Pnlp (SEQ ID NO: 54).
FIG. 2 shows cysteine resistance of a YeaSF137S-enhanced strain of *E. coli* MG1655 (growth curve). The symbol ○ represents the results for a wild-type or non-mutant, and the symbol ● represents the results for the F137S mutant strain.

The bacterium in accordance with the presently disclosed subject matter has an ability to produce one or more L-amino acid, and has been modified to have a mutation in the yeaS gene.

Although the type of the L-amino acid is not particularly limited, examples include basic amino acids such as L-lysine, L-ornithine, L-arginine, L-histidine and L-citrulline, aliphatic amino acids such as L-isoleucine, L-alanine, L-valine, L-leucine and L-glycine, amino acids which are hydroxy-monoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, and acidic amino acids such as L-glutamic acid, L-aspartic acid, L-glutamine and L-asparagine. L-Cysteine, L-leucine, L-threonine, L-serine, L-methionine, L-histidine, L-valine, L-glutamic acid, L-arginine, L-isoleucine, L-phenylalanine, L-tyrosine, L-tryptophan, and L-proline, and especially L-cysteine are particular examples. The bacterium in accordance with the presently disclosed subject matter can be able to produce two or more kinds of amino acids.

The L-amino acid includes L-amino acids in free form and salts thereof, such as sulfates, hydrochlorides, carbonates, ammonium salts, sodium salts, and potassium salts.

The ability to produce an L-amino acid can mean an ability of the bacterium to produce and cause accumulation of an L-amino acid in a medium or cells of the bacterium in such an amount that the L-amino acid can be collected from the medium or cells when the bacterium is cultured in the medium. The bacterium which is able to produce an L-amino acid can mean a bacterium which can produce and cause accumulation of an increased amount of L-amino acid in a medium as compared to a wild-type or parent strain, and can also mean a bacterium which can produce and cause accumulation of an L-amino acid in a medium in an amount of 0.2 g/L or more, 0.3 g/L or more, or even 0.4 g/L or more.

When the L-amino acid is L-cysteine, a portion of the L-cysteine produced by the bacterium can be converted into L-cystine in the medium by the formation of a disulfide bond. Furthermore, as described below, S-sulfocysteine can be generated by the reaction of L-cysteine and thio sulfuric acid which are present in the medium (Szczepkowski T. W., Nature, vol. 182 (1958)). Furthermore, L-cysteine generated in bacterial cells can be condensed with a ketone, aldehyde, or, for example, pyruvic acid, which is present in the cells, to produce a thiazolidine derivative via a hemithioketal (refer to Japanese Patent No. 2992010). Thiazolidine derivatives and hemithioketals can exist as an equilibrated mixture. Therefore, the ability to produce L-cysteines not limited the production of only L-cysteine in a medium or cells, but also includes the production of L-cystine or derivatives thereof such as S-sulfocysteine, a thiazolidine derivative, or a hemithioketal, or a mixture thereof. The "L-cysteine" produced by the method in accordance with the presently disclosed subject matter refers to, unless specifically mentioned, reduced-type L-cysteine, L-cystine, and derivatives such as those mentioned above or a mixture thereof.

The ability to produce an L-amino acid can be inherent to the bacterium, or it can be obtained by modifying a bacterium such as those described below by mutagenesis or recombinant DNA techniques.

The bacterium is not particularly limited so long as the bacterium belongs to the family Enterobacteriaceae such as those of the genera *Escherichia, Enterobacter, Pantoea, Klebsiella, Serratia, Erwinia, Salmonella* and *Morganella*, and has L-cysteine-producing ability. Specifically, those classified into the family Enterobacteriaceae according to the taxonomy used in the NCBI (National Center for Biotechnology Information) database can be used. As a parent strain of the family Enterobacteriaceae used for the modification, a bacterium of the genus *Escherichia, Enterobacter, Pantoea, Erwinia*, or *Klebsiella* can be used.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. Among these, *Escherichia coli* is one example. Examples of *Escherichia coli* include bacteria derived from the prototype wild-type strain, K12 strain, such as *Escherichia coli* W3110 (ATCC 27325), *Escherichia coli* MG1655 (ATCC 47076), and so forth.

These strains are available from, for example, American Type Culture Collection (Address: 12301 Parklawn Drive, Rockville, Md. 20852, P.O. Box 1549, Manassas, Va. 20108, United States of America). That is, accession numbers are given to each of the strains, and the strains can be ordered by using these registration numbers. The accession numbers of the strains are listed in the catalogue of the American Type Culture Collection.

Examples of the *Enterobacter* bacteria include *Enterobacter agglomerans, Enterobacter aerogenes* and so forth, and examples of the *Pantoea* bacteria include *Pantoea ananatis*. Some strains of *Enterobacter agglomerans* were recently reclassified into *Pantoea agglomerans, Pantoea ananatis*, or *Pantoea stewartii* on the basis of nucleotide sequence analysis of 16S rRNA etc. A bacterium belonging to the genus *Enterobacter* or *Pantoea* can be used so long as it is classified into the family Enterobacteriaceae.

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; International Journal of Systematic Bacteriology, October 1997, pp. 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39:337-345). Furthermore, some bacteria belonging to the genus *Erwinia* were reclassified as *Pantoea ananas* or *Pantoea stewartii* (refer to International Journal of Systematic Bacteriology, January 1993, 43(1), pp. 162-173).

Examples of the *Enterobacter* bacteria include, but are not limited to, *Enterobacter agglomerans, Enterobacter aerogenes*, and so forth. Specifically, the strains exemplified in European Patent Publication No. 952221 can be used. A typical strain of the genus *Enterobacter* is the *Enterobacter agglomeranses* ATCC 12287 strain.

Typical strains of the *Pantoea* bacteria include, but are not limited to, *Pantoea* ananatis, *Pantoea stewartii, Pantoea agglomerans*, and *Pantoea citrea*. Specific examples of *Pantoea ananatis* include the *Pantoea ananatis* AJ13355 strain, the SC17 strain, and the SC17(0) strain. The SC17 strain is selected as a low phlegm-producing mutant strain from the AJ13355 strain (FERM BP-6614) isolated from soil in Iwata-shi, Shizuoka-ken, Japan as a strain that can proliferate in a low pH medium containing L-glutamic acid and a carbon source (U.S. Pat. No. 6,596,517). The SC17(0) strain was constructed to be resistant to the λ Red gene product for performing gene disruption in *Pantoea ananatis* (WO2008/075483). The SC17 strain was deposited at the National Institute of Advanced Industrial Science and Technology, International Patent Organism Depository (address: Tsukuba Central 6, 1-1, Higashi 1-Chome, Tsukuba-shi, Ibaraki-ken, 305-8566, Japan) on Feb. 4, 2009, and assigned an accession number of FERM ABP-11091. The SC17(0) strain was deposited at the Russian National Collection of Industrial Microorganisms (VKPM), GNII Genetika (address: Russia, 117545 Moscow, 1 Dorozhny proezd. 1) on Sep. 21, 2005 with an accession number of VKPM B-9246.

The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was identified as *Enterobacter agglomerans* when it was isolated and deposited as the *Enterobacter agglomerans* AJ13355 strain. However, it was recently reclassified as *Pantoea ananatis* on the basis of nucleotide sequencing of 16S rRNA and so forth.

Examples of the *Erwinia* bacteria include, but are not limited to, *Erwinia amylovora* and *Erwinia carotovora*, and examples of the *Klebsiella* bacteria include *Klebsiella planticola.*

Imparting or Enhancing the Ability to Produce an L-Amino Acid

To impart the ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an analogue-resistant strain, or a metabolic regulation mutant, or by constructing a recombinant strain so that it overexpresses an L-amino acid biosynthesis enzyme. Here, in the breeding of L-amino acid-producing bacteria, one or more of the above-described properties such as auxotrophy, analogue resistance, and metabolic regulation mutation can be imparted. The expression of L-amino acid biosynthesis enzyme(s) can be enhanced alone or in combinations of two or more. Furthermore, the methods of imparting properties such as an auxotrophy, analogue resistance, or metabolic regulation mutation can be combined with enhancement of the biosynthesis enzymes.

An auxotrophic mutant strain, L-amino acid analogue-resistant strain, or metabolic regulation mutant strain with the ability to produce an L-amino acid can be obtained by subjecting a parent or wild-type strain to conventional mutatagenesis, such as exposure to X-rays or UV irradiation, or treatment with a mutagen such as N-methyl-N'-nitro-N-nitrosoguanidine or ethyl methanesulfonate (EMS), then selecting those which exhibit autotrophy, analogue resistance, or a metabolic regulation mutation and which also have the ability to produce an L-amino acid.

Moreover, the ability to produce an L-amino acid can also be imparted or enhanced by increasing the enzymatic activity by gene recombination. An example of the method for increasing enzymatic activity includes modifying the bacterium so that the expression of a gene coding for an enzyme involved in the biosynthesis of an L-amino acid is enhanced. Gene expression can also be increased by introducing an amplification plasmid prepared by introducing a DNA fragment containing the gene into an appropriate plasmid which contains, for example, at least a gene responsible for replication and proliferation of the plasmid in the microorganism, increasing the copy number of the gene on the chromosome by conjugation, transfer, or the like, or introducing a mutation into the promoter region of the gene (refer to International Patent Publication WO95/34672).

When an objective gene is introduced into the aforementioned amplification plasmid or chromosome, any promoter can be used to express the gene so long as the chosen promoter functions in bacteria belonging to the family Enterobacteriaceae. The promoter can be the native promoter for the gene, or a modified promoter. The expression of a gene can also be controlled by suitably choosing a promoter that strongly functions in bacteria belonging to the family Enterobacteriaceae, or by making the −35 and −10 regions of the promoter closer to the consensus sequence. These methods for enhancing expression of enzyme genes are fully described in International Patent Publication WO00/18935, European Patent Publication No. 1010755, and so forth.

Specific methods for imparting an L-amino acid-producing ability to bacteria and bacteria imparted with L-amino acid-producing ability are exemplified below.

L-Cysteine-Producing Bacteria

Examples of L-cysteine-producing bacteria and parent strains which can be used to derive L-cysteine-producing bacteria include, but are not limited to, strains belonging to the genus *Escherichia*, such as *E. coli* JM15 which is transformed with different cysE alleles encoding feedback-resistant serine acetyltransferases (SAT) (U.S. Pat. No. 6,218,168); *E. coli* W3110 having over-expressed genes which encode proteins suitable for secreting substances toxic for cells (U.S. Pat. No. 5,972,663); *E. coli* strains having lowered cysteine desulfohydrase activity (Japanese Patent Laid-open No. 11-155571); *E. coli* W3110 with increased activity of a positive transcriptional regulator for cysteine regulon encoded by the cysB gene (WO01/27307), and so forth. The bacterium in accordance with the presently disclosed subject matter has been modified to have a yeaS gene having a specific mutation. As will be described below, it is presumed that the protein encoded by the yeaS gene (henceforth also referred to as "YeaS protein") has an activity of secreting L-amino acids such as L-cysteine out of cells.

For *E. coli*, proteins are known which have an activity of secreting L-cysteine, such as the protein encoded by ydeD (Japanese Patent Laid-open No. 2002-233384), the protein encoded by yfiK (Japanese Patent Laid-open No. 2004-49237) and the proteins encoded by emrAB, emrKY, yojIH, acrEF, bcr, and cusA, respectively (Japanese Patent Laid-open No. 2005-287333) as described above. In addition to mutating the yeaS gene in the bacterium, the activities of a SAT resistant to feedback inhibition and L-cysteine secreting proteins can be increased.

Hereafter, as the method for imparting an ability to produce L-cysteine, enhancing an activity of L-cysteine biosynthesis system enzyme will be described.

Examples of the L-cysteine biosynthesis enzyme include, for example, serine acetyltransferase (SAT). The SAT activity in cells of a bacterium belonging to the family Enterobacteriaceae can be enhanced by increasing the copy number of a gene coding for SAT, or modifying an expression control sequence such as promoter of the gene coding for SAT. For example, a recombinant DNA can be prepared by ligating a gene fragment coding for SAT with a vector, such as a multi-copy vector, which is able to function in the chosen host bacterium belonging to the family Enterobacteriaceae to prepare a recombinant DNA. This recombinant DNA can then introduced into a host bacterium belonging to the family Enterobacteriaceae to transform it. More specifically, a method similar to the method for the yeaS gene described later can be applied.

As the SAT gene, an SAT derived from *Escherichia* bacteria and or an SAT gene derived from other organisms can be used. As the gene coding for SAT of *Escherichia coli*, cycE has been cloned from a wild-type strain and an L-cysteine excretion mutant strain, and the nucleotide sequence thereof has been elucidated (Denk, D. and Boeck, A., J. General Microbiol., 133, 515-525 (1987)). Therefore, a SAT gene can be obtained by PCR utilizing primers prepared based on the nucleotide sequence (SEQ ID NO: 3) and chromosomal DNA of *Escherichia* bacterium as the template (refer to Japanese Patent Laid-open No. 11-155571). Genes coding for SAT of other organisms can also be obtained in a similar manner. Expression of the SAT gene as described above can be enhanced in the same manner as that explained above.

When a suppression mechanism such as "feedback inhibition by L-cysteine" exists for the expression of the SAT gene, expression of the SAT gene can also be enhanced by modifying an expression regulatory sequence or a gene involved in the suppression so that the expression of the SAT gene is insensitive to the suppression mechanism.

For example, the SAT activity can be further increased by mutating the SAT so that the feedback inhibition by L-cysteine is reduced or eliminated in the bacterium (henceforth also referred to as "mutant SAT"). Examples of the mutant SAT include SAT having a mutation replacing an amino acid residue corresponding to the methionine residue at position 256 of a wild-type SAT (SEQ ID NO: 4) with an amino acid residue other than lysine residue and leucine residue, or a mutation deleting a C-terminus side region from an amino acid residue corresponding to the methionine residue as position 256. Examples of the amino acid residues other than lysine and leucine include the 17 amino acid residues which typically make up proteins, except for methionine, lysine and leucine. Isoleucine and glutamic acid are examples. To introduce a desired mutation into a wild-type SAT gene, site-specific mutagenesis can be used. As a mutant SAT gene, a mutant cysE coding for a mutant SAT of *Escherichia coli* is known (refer to International Patent Publication WO97/15673 and Japanese Patent Laid-open No. 11-155571). *Escherichia coli* JM39-8 strain harboring a plasmid pCEM256E containing a mutant cysE coding for a mutant SAT in which methionine residue at position 256 is replaced with a glutamic acid residue (*E. coli* JM39-8 (pCEM256E), private number: AJ13391) was deposited at the National Institute of Bioscience and Human-Technology, Agency of Industrial Science and Technology (Postal code: 305, 1-3 Higashi 1-Chome, Tsukuba-shi, Ibaraki-ken, Japan) on Nov. 20, 1997 and assigned an accession number of FERM P-16527. The deposit was then converted to an international deposit under the provisions of Budapest Treaty on Jul. 8, 2002, and assigned an accession number of FERM BP-8112.

Although a "SAT insensitive to feedback inhibition by L-cysteine" can be a SAT which has been modified so that it is insensitive to the feedback inhibition by L-cysteine, it can be a SAT which in its native form is insensitive to feedback inhibition by L-cysteine. For example, SAT of *Arabidopsis thaliana* is known to be not subject to feedback inhibition by L-cysteine and can be suitably used. As a plasmid containing the SAT gene derived from *Arabidopsis thaliana*, pEAS-m is known (FEMS Microbiol. Lett., 179 (1999) 453-459).

Furthermore, the ability to produce L-cysteine can also be improved by enhancing expression of the cysPTWAM cluster genes coding for the sulfate/thiosulfate transport system proteins (Japanese Patent Laid-open No. 2005-137369, EP 1528108).

Furthermore, a sulfide can be incorporated into O-acetyl-L-serine via a reaction catalyzed by the O-acetylserine (thiol)-lyase A or B encoded by the cysK and cysM genes, respectively, to produce L-cysteine. Therefore, the ability to produce L-cysteine can also be improved by enhancing expression of the genes coding for these enzymes.

An objective gene can be modified to enhance expression by, for example, increasing the copy number of the objective gene in the cells by means of genetic recombination techniques. For example, a recombinant DNA can be prepared by ligating a DNA fragment containing the objective gene with a vector, such as a multi-copy vector, which is able to function in a host microorganism, and introduced into a bacterium to transform it.

The copy number of an objective gene can also be increased by introducing multiple copies of the objective gene into a chromosomal DNA of a bacterium. Multiple copies of the objective gene can be introduced into a chromosomal DNA of a bacterium by the method described later for the mutant yeaS gene.

Besides amplifying the copy number of gene described above, expression of an objective gene can also be enhanced by replacing an expression regulatory sequence of the objective gene yeaS, such as a promoter, on a chromosomal DNA or a plasmid with a stronger promoter, amplifying a regulator which increases expression of the objective gene, or deleting or attenuating a regulator which reduces expression of the objective gene. As a regulator which reduces expression of an objective gene, the Lrp protein and so forth are known (Kutukova et al., FEBS Lett., 579, 4629-4634 (2005)). As strong promoters, for example, lac promoter, trp promoter, trc promoter and so forth are known. Furthermore, a promoter of an objective gene can also be modified to be stronger by introducing substitution of nucleotides or the like into the promoter region of the objective gene. The aforementioned substitution or modification of the promoter enhances expression of the objective gene. Examples of methods for evaluating the strength of promoters and strong promoters are described in an article by Goldstein and Doi (Goldstein, M. A. and Doi R. H., 1995, Prokaryotic promoters in biotechnology. Biotechnol. Annu. Rev., 1, 105-128), and so forth. Modification of an expression regulatory sequence can be combined with the increasing the copy number of an objective gene. Furthermore, in order to enhance production of an objective gene product, a mutation can be introduced near the translation initiation site of the objective gene to increase translation efficiency, and this can be combined with enhancing the expression of the objective gene.

Increase of expression level of the objective gene can be confirmed by comparing the amount of mRNA transcribed from the objective gene with that of the wild-type or non-modified strain. Examples of the method for confirming mRNA amount include Northern hybridization and reverse transcriptase PCR (RT-PCR, Sambrook, J., and Russell, D. W., Molecular Cloning A Laboratory Manual/Third Edition, Cold Spring Harbor Laboratory Press, Cold Spring Harbor (USA), 2001).

Increase of the amount of an objective gene product can also be confirmed by Western blotting using an antibody ("Molecular Cloning . . . " mentioned above).

Moreover, L-cysteine-producing ability can also be improved by suppressing the L-cysteine decomposition system. "L-cysteine decomposition system is suppressed" can mean that intracellular L-cysteine decomposition activity is decreased as compared to that of a non-modified strain such as a wild-type or parent strain. As proteins responsible for the L-cysteine decomposition system, cystathionine-β-lyase (metC product, Japanese Patent Laid-open No. 11-155571, Chandra et al., Biochemistry, 21 (1982) 3064-3069), tryptophanase (tnaA product, Japanese Patent Laid-open No. 2003-169668, Austin Newton et al., J. Biol. Chem., 240 (1965) 1211-1218)), O-acetylserine sulfhydrylase B (cysM gene product, Japanese Patent Laid-open No. 2005-245311) and the malY gene product (Japanese Patent Laid-open No. 2005-245311) are known. By decreasing the activities of these proteins, L-cysteine-producing ability can be improved.

Activity of a protein can be decreased by, for example, reducing expression of a gene coding for the protein. Specifically, for example, intracellular activity of the protein can be reduced by deleting a part of, or the entire coding region of the gene on a chromosome. Expression of a gene can also be decreased by modifying an expression control sequence of the gene such as promoter and Shine-Dalgarno (SD) sequence. Furthermore, the expression of the gene can also be reduced by modification of a non-translation region other than the expression control sequence. Furthermore, the entire gene including the sequences on both sides of the gene on a chromosome can be deleted. Furthermore, the expression of the gene can also be reduced by introducing a mutation for an amino acid substitution (missense mutation), a stop codon (nonsense mutation), or a frame shift mutation which adds or deletes one or two nucleotides into the coding region of the objective gene on a chromosome (Journal of Biological Chemistry, 272:8611-8617 (1997); Proceedings of the National Academy of Sciences, USA, 95 5511-5515 (1998); Journal of Biological Chemistry, 266, 20833-20839 (1991)).

Furthermore, the modification can be caused by a typical mutagenesis caused by X-ray or ultraviolet irradiation, or by use of a mutagen such as N-methyl-N'-nitro-N-nitrosoguanidine, so long as the modification results in a decrease of the activity of the target protein.

Modification of an expression control sequence is performed for one or more nucleotides in one example, two or more nucleotides in another example, three or more nucleotides in another example. When a coding region is deleted, the region to be deleted can be an N-terminal region, an internal region or a C-terminal region, or even the entire coding region, so long as the function of the target protein is decreased or deleted. Deletion of a longer region can usually more surely inactivate a gene. Furthermore, reading frames upstream and downstream of the region to be deleted can be the same or different.

To inactivate a gene by inserting a sequence into the coding region of the gene, the sequence can be inserted into any part of the coding region of the gene. The longer the inserted sequence, the greater the likelihood of inactivating the gene. Reading frames located upstream and downstream of the insertion site can be the same or different. The sequence to be inserted is not particularly limited so long as the insertion decreases or deletes the function of the encoded protein, and examples include, for example, a transposon carrying an antibiotic resistance gene, a gene useful for L-cysteine production and so forth.

L-Threonine-Producing Bacteria

Examples of microorganisms having L-threonine-producing ability include bacteria in which one or more activities of L-threonine biosynthesis system enzymes are enhanced. Examples of L-threonine biosynthetic enzymes include aspartokinase III (lysC), aspartate semialdehyde dehydrogenase (asd), aspartokinase I (thrA), homoserine kinase (thrB), threonine synthase (thrC) encoded by thr operon, and aspartate aminotransferase (aspartate transaminase) (aspC). The names of the genes coding for the respective enzymes are mentioned in the parentheses after the names of the enzymes (the same shall apply throughout this specification). Among these enzymes, aspartate semialdehyde dehydrogenase, aspartokinase I, homoserine kinase, aspartate aminotransferase, and threonine synthase are examples. The genes coding for the L-threonine biosynthetic enzymes can be introduced into an *Escherichia* bacterium which has a reduced ability to decompose threonine. An example of such an *Escherichia* bacterium is the TDH6 strain which is deficient in threonine dehydrogenase activity (Japanese Patent Laid-open No. 2001-346578).

The enzymatic activities of the L-threonine biosynthetic enzymes are inhibited by the end product, L-threonine. Therefore, the genes for the L-threonine biosynthetic enzymes can be modified so that the enzymes are desensitized to feedback inhibition by L-threonine in the L-threonine-producing strains. The aforementioned thrA, thrB, and thrC genes constitute the threonine operon, which contains an attenuator. The expression of the threonine operon is inhibited by isoleucine and threonine in the culture medium and also suppressed by attenuation. Therefore, the threonine operon can be modified by removing the leader sequence or the sequence responsible for attenuation in the attenuator region (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808).

The native promoter of the threonine operon is present upstream of the threonine operon, and can be replaced with a non-native promoter (refer to WO98/04715), or a threonine operon which has been modified so that expression of the threonine biosynthesis gene is controlled by the repressor and promoter of λ-phage can be constructed (EP 0593792). Furthermore, in order to modify a bacterium so that it is desensitized to feedback inhibition by L-threonine, a strain resistant to α-amino-β-hydroxyisovaleric acid (AHV) can be selected.

The copy number of the threonine operon that is modified to desensitize to feedback inhibition by L-threonine can be increased, or the expression of the threonine operon can be increased by ligating it to a potent promoter. The copy number can also be increased by, besides amplification using a plasmid, transferring the threonine operon to a genome using a transposon, Mu-phage, or the like.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of such genes include the genes encoding transhydrogenase (pntAB, EP 733712 B), phosphoenolpyruvate carboxylase (pepC, WO95/06114), phosphoenolpyruvate synthase (pps, EP 877090 B), and a gene encoding pyruvate carboxylase from coryneform bacterium or *Bacillus* bacterium (WO99/18228, EP 1092776 A).

Resistance to L-threonine, L-homoserine, or both can be imparted to the host by, for example, enhancing expression of a gene that imparts resistance to L-threonine or L-homoserine. Examples of these genes include rhtA (Res. Microbiol., 154:123-135 (2003)), rhtB (EP 0994190 A), rhtC (EP 1013765 A), yfiK, and yeaS (EP 1016710 A). The methods for imparting L-threonine resistance to a host are described in EP 0994190 A and WO90/04636.

Examples of L-threonine-producing bacteria and parent strains which can be used to derive such bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and so forth.

The TDH-6 strain is deficient in the thrC gene, as well as being sucrose-assimilative, and the ilvA gene has a leaky mutation. This strain also has a mutation in the rhtA gene, which imparts resistance to high concentration of threonine or homoserine. The B-3996 strain contains the plasmid pVIC40, which was obtained by inserting the thrA*BC operon, including a mutant thrA gene, into the RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792 B) can also be used as an L-threonine-producing bacterium or a parent strain for deriving it. The B-5318 strain is prototrophic with regard to isoleucine, and a temperature-sensitive lambda-phage Cl repressor and PR promoter replace the regulatory region of the threonine operon in the plasmid pVIC40. The VKPM B-5318 strain was deposited at the Russian National Collection of Industrial Microorganisms (VKPM) (1 Dorozhny proezd., 1 Moscow 117545, Russia) on May 3, 1990 under the accession number of VKPM B-5318.

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC 000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC 000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feedback inhibition by threonine, as well as the thrB and thrC genes can be obtained as one operon from the well-known pVIC40 plasmid, which is present in the threonine-producing *E. coli* strain VKPM B-3996. pVIC40 is described in detail in U.S. Pat. No. 5,705,371.

The rhtA gene is present at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi: 440181) and is located between the pexB and ompX genes. The unit expressing the protein encoded by the ORP1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide numbers 3572511 to 3571408, GenBank accession NC_000913.1, gi: 16131307), and can be obtained by PCR (polymerase chain reaction; refer to White, T. J. et al., Trends Genet, 5, 185 (1989)) utilizing primers prepared based on the nucleotide sequence of the gene. The asd genes of other microorganisms can also be obtained in a similar manner.

Also, the aspC gene of *E. coli* has already been elucidated (nucleotide numbers 983742 to 984932, GenBank accession NC 000913.1, gi: 16128895), and can be obtained by PCR. The aspC genes of other microorganisms can also be obtained in a similar manner.

L-Lysine-Producing Bacteria

Examples of L-lysine-producing bacteria belonging to the genus *Escherichia* include mutants having resistance to an L-lysine analogue. L-lysine analogues inhibit the growth of *Escherichia* bacteria, but this inhibition is fully or partially desensitized when L-lysine is present in the medium. Examples of these L-lysine analogues include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting *Escherichia* bacteria to conventional artificial mutagenesis treatments. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

Examples of L-lysine-producing bacteria and parent strains which can be used to derive L-lysine-producing bacteria also include strains in which expression of one or more genes encoding an L-lysine biosynthetic enzyme are enhanced. Examples of such enzymes include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), diaminopimelate epimerase (dapF), aspartate semialdehyde dehydrogenase gene (asd), tetrahydrodipicolinate succinylase (dapD), succinyl diaminopimelate deacylase (dapE), and aspartase (aspA) (EP 1253195 A). Among these enzymes, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase are particular examples. In addition, the parent strains can express increased levels of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of L-lysine-producing bacteria and parent strains which can be used to derive L-lysine-producing bacteria also include strains in which the activity of one or more enzymes that catalyze one or more reactions which direct synthesis of one or more compounds other than L-lysine, for example, by directing synthesis away from the biosynthetic pathway of L-lysine, is reduced or eliminated. Examples of these enzymes include homoserine dehydrogenase, lysine decarboxylase (U.S. Pat. No. 5,827,698), and the malic enzyme (WO2005/010175).

Decrease of enzyme activity can be achieved by, for example, deleting a part of or entire region of the coding region of a target enzyme gene on a chromosome, or inserting another sequence into the coding region. These techniques are also called gene disruption. A target gene can also be inactivated by decreasing expression of the gene via modification of an expression control sequence of the target gene such as a promoter or Shine Dargarno (SD) sequence. Decrease of expression includes decrease of transcription and translation. Expression of a gene can also be reduced by modifying a non-translation region other than expression control regions.

Furthermore, entire target gene including upstream and downstream regions of the gene on a chromosome can be deleted. In addition, a target gene can also be inactivated by introducing a mutation for an amino acid substitution (missense mutation), a stop codon (nonsense mutation), or a frame shift mutation which adds or deletes one or two nucleotides into the coding region of the target gene on a chromosome (Journal of Biological Chemistry, 272:8611-8617 (1997), Proceedings of the National Academy of Sciences, USA, 95 5511-5515 (1998), Journal of Biological Chemistry, 266, 20833-20839 (1991)).

An example of an L-lysine producing strain is *E. coli* WC196ΔcadAΔldcC/pCABD2 (WO2006/078039). This strain was obtained by introducing the pCABD2 plasmid containing lysine biosynthesis enzyme genes (U.S. Pat. No. 6,040,160) into the WC196 strain, in which the cadA and ldcC genes coding for lysine decarboxylase are disrupted. The WC196 strain was bred from the W3110 strain, which was derived from *Escherichia coli* K-12, by replacing the wild type lysC gene on the chromosome of the W3110 strain with a mutant lysC gene encoding a mutant aspartokinase III desensitized to feedback inhibition by L-lysine in which threonine at position 352 had been replaced with isoleucine, and conferring AEC resistance to the resulting strain (U.S. Pat. No. 5,661,012). The WC196 strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldcC strain per se is also L-lysine producing strain. The WC196ΔcadAΔldcC strain was designated *Escherichia coli* AJ110692 and was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit under the provisions of the Budapest Treaty and assigned an accession number of FERM BP-11027.

The pCABD2 plasmid contains the dapA gene derived from *Escherichia coli*, which has been mutated to encode dihydrodipicolinate synthase (DDPS) which is desensitized to the feedback inhibition by L-lysine, the lysC gene derived from *Escherichia coli*, which has been mutated to encode aspartokinase III which is desensitized to feedback inhibition by L-lysine, the dapB gene derived from *Escherichia coli* coding for dihydrodipicolinate reductase, and the ddh gene derived from *Brevibacterium lactofermentum* coding for diaminopimelate dehydrogenase (WO95/16042, WO01/53459).

L-Leucine-Producing Bacteria

Examples of L-leucine-producing bacteria and parent strains which can be used to derive L-leucine-producing bacteria include, but are not limited to, *Escherichia* bacterial strains, such as *E. coli* strains resistant to leucine (for example, the 57 strain (VKPM B-7386, U.S. Pat. No. 6,124,121)) or leucine analogues including β-2-thienylalanine, 3-hydroxyleucine, 4-azaleucine, 5,5,5-trifluoroleucine, and so forth (Japanese Patent Publication (Kokoku) No. 62-34397 and Japanese Patent Laid-open No. 8-70879), *E. coli* strains obtained by the genetic engineering method described in WO96/06926, *E. coli* H-9068 (Japanese Patent Laid-open No. 8-70879), and so forth.

The bacterium can be improved by enhancing expression of one or more genes involved in L-leucine biosynthesis. Examples of such genes include the genes of the leuABCD operon, a typical example of which is the mutant leuA gene coding for isopropyl malate synthase which has been mutated to be desensitized to feedback inhibition by L-leucine (U.S. Pat. No. 6,403,342). In addition, the bacterium can be improved by enhancing expression of one or more genes coding for proteins which increase secretion of L-amino acid from bacterial cells. Examples of such genes include the b2682 and b2683 (the ygaZH genes) (EP 1239041 A2).

L-Histidine-Producing Bacteria

Examples of L-histidine-producing bacteria and parent strains which can be used to derive L-histidine-producing bacteria include, but are not limited to, *Escherichia* bacterial strains, such as *E. coli* strain 24 (VKPM B-5945, RU2003677), *E. coli* strain 80 (VKPM B-7270, RU2119536), *E. coli* NRRL B-12116-B 12121 (U.S. Pat. No. 4,388,405), *E. coli* H-9342 (FERM BP-6675), *E. coli*

H-9343 (FERM BP-6676) (U.S. Pat. No. 6,344,347), *E. coli* H-9341 (FERM BP-6674) (EP 1085087), *E. coli* AI80/pFM201 (U.S. Pat. No. 6,258,554), and so forth.

Examples of L-histidine-producing bacteria and parent strains which can be used to derive L-histidine-producing bacteria also include strains in which the expression of one or more genes encoding L-histidine biosynthetic enzymes is enhanced. Examples of such genes include the genes encoding ATP phosphoribosyltransferase (hisG), phosphoribosyl AMP cyclohydrolase (histI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore the ability to produce L-histidine can also be efficiently enhanced by introducing a mutation which confers resistance to feedback inhibition into the gene coding for ATP phosphoribosyltransferase (hisG) (Russian Patent Nos. 2003677 and 2119536).

Specific examples of strains which are able to produce L-histidine include *E. coli* FERM-P 5038 and 5048 which have been transformed with a vector carrying a DNA encoding an L-histidine-biosynthetic enzyme (Japanese Patent Laid-open No. 56-005099), *E. coli* strains transformed with a gene encoding a protein involved in amino acid export (EP 1016710 A), *E. coli* 80 strain which is resistant to sulfaguanidine, DL-1,2,4-triazole-3-alanine, and streptomycin (VKPM B-7270, Russian Patent No. 2119536), and so forth.

L-Glutamic Acid-Producing Bacteria

Examples of L-glutamic acid-producing bacteria and parent strains which can be used to derive L-glutamic acid-producing bacteria include, but are not limited to, *Escherichia* bacterial strains, such as *E. coli* VL334thrC$^+$ (EP 1172433). *E. coli* VL334 (VKPM B-1641) is auxotrophic for L-isoleucine and L-threonine and contains mutant thrC and ilvA genes (U.S. Pat. No. 4,278,765). A wild-type allele of the thrC gene was transferred by general transduction using bacteriophage P1 grown on wild-type *E. coli* K12 (VKPM B-7) cells, resulting in a strain, which is able to produce L-glutamic acid. This strain was named VL334thrC$^+$ (VKPM B-8961).

Examples of L-glutamic acid-producing bacteria and parent strains which can be used to derive L-glutamic acid-producing bacteria also include, but are not limited to, strains in which expression of one or more genes encoding an L-glutamic acid biosynthetic enzyme is enhanced. Examples of such genes include the genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), methyl citrate synthase gene (prpC), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), glucose phosphate isomerase (pgi), and so forth. Among these enzymes, glutamate dehydrogenase, citrate synthase, phosphoenolpyruvate carboxylase, and methyl citrate synthase are examples.

Examples of strains which have been modified so that expression of the citrate synthetase gene, the phosphoenolpyruvate carboxylase gene, and/or the glutamate dehydrogenase gene is enhanced include those disclosed in EP 1078989 A, EP 955368 A, and EP 952221 A.

Examples of L-glutamic acid-producing bacteria and parent strains which can be used to derive L-glutamic acid-producing bacteria also include strains in which the activity of one or more enzymes that catalyze one or more reactions which direct synthesis of one or more compounds other than L-glutamic acid, for example, by directing synthesis away from the biosynthetic pathway of L-glutamic acid, is reduced or eliminated. Examples of these enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and so forth. *Escherichia* bacteria without α-ketoglutarate dehydrogenase activity or with reduced α-ketoglutarate dehydrogenase activity and methods to obtain such bacteria are described in U.S. Pat. Nos. 5,378,616 and 5,573,945.

Specifically, these strains include the following:

*E. coli* W3110sucA::Km$^r$

*E. coli* AJ12624 (FERM BP-3853)

*E. coli* AJ12628 (FERM BP-3854)

*E. coli* AJ12949 (FERM BP-4881)

*E. coli* W3110sucA::Km$^r$ is obtained by disrupting the α-ketoglutarate dehydrogenase gene (hereinafter also referred to as the "sucA gene") of *E. coli* W3110. This strain is completely deficient in α-ketoglutarate dehydrogenase.

Other examples of L-glutamic acid-producing bacterium include *Escherichia* bacteria which are resistant to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally is unable to decompose L-glutamic acid (U.S. Pat. No. 5,393,671); AJ13138 (FERM BP-5565) (U.S. Pat. No. 6,110,714), and so forth.

An example of an L-glutamic acid-producing bacterium which belongs to *Pantoea ananatis* is the *Pantoea ananatis* AJ13355 strain. This strain was isolated from soil in Iwata-shi, Shizuoka-ken, Japan, and was identified as being able to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was originally identified as *Enterobacter agglomerans* when it was isolated, and deposited as *Enterobacter agglomerans* AJ13355. However, it was recently re-classified as *Pantoea ananatis* on the basis f nucleotide sequencing of 16S rRNA and so forth.

Furthermore, examples of an L-glutamic acid-producing bacterium of *Pantoea ananatis* also include *Pantoea ananatis* deficient in α-ketoglutarate dehydrogenase (αKGDH) activity or having reduced αKGDH activity. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517) which also does not have the sucA gene, and was selected from AJ13355 for its low phlegm production properties. The AJ13356 strain was deposited at the National Institute of Bioscience and Human-Technology, Agency of Industrial Science and Technology, Ministry of International Trade and Industry (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains were deposited at the aforementioned depository as *Enterobacter agglomerans*, they are referred to as *Pantoea ananatis* in this specification. The SC17sucA strain was assigned the private number of AJ417, and deposited at the National Institute of Advanced Industrial Science and Technology, International Patent Organism Depositary on Feb. 26, 2004, under an accession number of FERM BP-08646.

Examples of L-glutamic acid-producing *Pantoea ananatis* bacteria further include SC17sucA/RSFCPG+pSTVCB, AJ13601, NP106, and NA1 strains. The SC17sucA/RSFCPG+pSTVCB strain was obtained by introducing the plasmid RSFCPG containing the citrate synthase gene (gltA), phosphoenolpyruvate carboxylase gene (ppsA), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain for its resistance to high concentration of L-glutamic acid at a low pH. Furthermore, the NP106 strain was derived from the AJ13601 strain by eliminating the RSFCPG+pSTVCB plasmid as described in the examples. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned accession number FERM P-17516. Then, the deposit was converted into an international deposit under the provisions of the Budapest Treaty on Jul. 6, 2000, and assigned an accession number FERM BP-7207.

L-Phenylalanine-Producing Bacteria

Examples of L-phenylalanine-producing bacteria and parent strains which can be used to derive L-phenylalanine-producing bacteria include, but are not limited to, *Escherichia* bacterial strains, such as *E. coli* AJ12739 (tyrA::Tn10, tyrR) (VKPM B-8197) which lacks chorismate mutase-prephenate dehydrogenase and the tyrosine repressor (WO03/044191), *E. coli* HW1089 (ATCC 55371) which contains the pheA34 gene coding for chorismate mutase-prephenate dehydratase which has been mutated to be desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Also, the following strains can be used to derive L-phenylalanine producing bacteria: *E. coli* K-12 [W3110(tyrA)/pPHAB (FERM BP-3566) which contains genes coding for chorismate mutase-prephenate dehydratase which has been mutated to be desensitized to feedback inhibition, *E. coli* K-12 [W3110(tyrA)/pPHAD] (FERM BP-12659), *E. coli* K-12 [W3110(tyrA)/pPHATerm] (FERM BP-12662), and *E. coli* K-12 [W3110(tyrA)/pBR-aroG4, pACMAB] (also known as AJ12604 (FERM BP-3579) (EP 488-424 B1). Furthermore, *Escherichia* L-phenylalanine-producing bacteria with enhanced activity of the protein encoded by the yedA gene or the yddG gene can also be used (U.S. Patent Published Applications Nos. 2003/0148473 A1 and 2003/0157667 A1, WO03/044192).

L-Tryptophan-Producing Bacteria

Examples of L-tryptophan-producing bacteria and parent strains which can be used to derive L-tryptophan-producing bacteria include, but are not limited to, *Escherichia* bacterial strains, such as *E. coli* JP4735/pMU3028 (DSM10122) and *E. coli* JP6015/pMU91 (DSM10123) which lack tryptophanyl-tRNA synthetase encoded by a mutant trpS gene (U.S. Pat. No. 5,756,345), *E. coli* SV164 (pGH5) which contains the serA allele encoding phosphoglycerate dehydrogenase and the trpE allele encoding anthranilate synthase, which are desensitized to feedback inhibition by serine and tryptophan, respectively (U.S. Pat. No. 6,180,373), *E. coli* AGX17 (pGX44) (NRRL B-12263), and *E. coli* AGX6(pGX50)aroP (NRRL B-12264) which lack tryptophanase (U.S. Pat. No. 4,371,614), and *E. coli* AGX17/pGX50, pACKG4-pps in which phosphoenolpyruvate-producing ability is enhanced (WO9708333, U.S. Pat. No. 6,319,696). L-Tryptophan-producing bacteria belonging to the genus *Escherichia* with enhanced activity of the protein encoded by the yedA gene or the yddG gene can also be used (U.S. Patent Published Application Nos. 2003/0148473 A1 and 2003/0157667 A1).

Examples of L-tryptophan-producing bacteria and parent strains which can be used to derive L-tryptophan-producing bacteria also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (CM-PD). Among these enzymes, phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, and chorismate mutase-prephenate dehydratase are particular examples. Anthranilate synthase and phosphoglycerate dehydrogenase both suffer from feedback inhibition by L-tryptophan and L-serine, and therefore a mutation desensitizing feedback inhibition can be introduced into the genes encoding these enzymes. Specific examples of strains having such a mutation include *E. coli* SV164 having a desensitized type anthranilate synthase and a transformant strain obtained by introducing pGH5 (WO94/08031) containing a mutant serA gene coding for phosphoglycerate dehydrogenase desensitized to feedback inhibition into *E. coli* SV164.

Examples of L-tryptophan-producing bacteria and parent strains which can be used to derive L-tryptophan-producing bacteria also include strains which have been transformed with the tryptophan operon and which contain a gene encoding inhibition-desensitized anthranilate synthase (Japanese Patent Laid-open Nos. 57-71397, 62-244382, U.S. Pat. No. 4,371,614). Moreover, L-tryptophan-producing ability can be imparted by enhancing expression of a gene which encodes tryptophan synthase in the tryptophan operon (trpBA). Tryptophan synthase includes both α and β subunits, which are encoded by trpA and trpB, respectively. In addition, L-tryptophan-producing ability can be improved by enhancing expression of the isocitrate lyase-malate synthase operon (WO2005/103275).

L-Proline-Producing Bacteria

Examples of L-proline-producing bacteria and parent strains which can be used to derive L-proline-producing bacteria include, but are not limited to, *Escherichia* bacterial strains, such as *E. coli* 702ilvA (VKPM B-8012) which lacks the ilvA gene and can produce L-proline (EP 1172433).

The bacterium can be improved by enhancing expression of one or more genes involved in L-proline biosynthesis. Examples of genes include the proB gene coding for glutamate kinase which is desensitized to feedback inhibition by L-proline (DE Patent 3127361). In addition, the bacterium can be improved by enhancing expression of one or more genes coding for proteins responsible for secretion of L-amino acids from the bacterial cell. Examples of such genes are b2682 and b2683 genes (ygaZH genes) (EP 1239041 A2).

*Escherichia* bacteria which produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami Winter Symposium, 1983, p. 34), and so forth.

L-Arginine-Producing Bacteria

Examples of L-arginine-producing bacteria and parent strains which can be used to derive L-arginine-producing bacteria include, but are not limited to, *Escherichia* bacterial strains, such as *E. coli* strain 237 (VKPM B-7925) (U.S. Patent Published Application No. 2002/058315 A1) and its derivative strains harboring mutant N-acetylglutamate synthase (Russian Patent Application No. 2001112869), *E. coli* strain 382 (VKPM B-7926) (EP 1170358A1), and an arginine-producing strain transformed with an argA gene encoding N-acetylglutamate synthetase (EP 1170361 A1).

Examples of L-arginine-producing bacteria and parent strains which can be used to derive L-arginine-producing bacteria also include strains in which the expression of one or more genes encoding an L-arginine biosynthetic enzyme is enhanced. Examples of such genes include the genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by the produced L-valine. Furthermore, the ilvA gene in the operon is desirably disrupted so that threonine deaminase activity is decreased.

Examples of L-valine-producing bacteria and parent strains which can be used to derive L-valine-producing bacteria also include mutants having amino-acyl t-RNA synthetase mutations (U.S. Pat. No. 5,658,766). An example is *E. coli* VL1970, which has a mutation in the ileS gene encoding isoleucine tRNA synthetase. *E. coli* VL1970 was deposited at the Russian National Collection of Industrial Microorganisms (VKPM) (1 Dorozhny proezd., 1 Moscow 117545, Russia) on Jun. 24, 1988 under the accession number VKPM B-4411.

Furthermore, mutant strains which require lipoic acid for growth and/or lack $H^+$-ATPase (WO96/06926) are also effective to derive L-valine-producing bacteria.

L-Isoleucine-Producing Bacteria

Examples of L-isoleucine producing bacteria and parent strains which can be used to derive L-isoleucine-producing bacteria include, but are not limited to, mutants which are resistant to 6-dimethylaminopurine (Japanese Patent Laid-open No. 5-304969), mutants which are resistant to isoleucine analogues such as thiaisoleucine and isoleucine hydroxamate, and mutants which are additionally resistant to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxate synthase, are also effective to derive L-isoleucine-producing bacteria (Japanese Patent Laid-open No. 2-458, FR 0356739, and U.S. Pat. No. 5,998,178).

L-Tyrosine-Producing Bacteria

Examples of tyrosine-producing bacteria include *Escherichia* bacteria with a desensitized prephenate dehydratase gene (tyrA). The expression product of this gene is desensitized to inhibition by tyrosine (European Patent Application Laid-open No. 1616940).

In the bacterium, in order to enhance glycerol assimilability, expression of the glpR gene (EP 1715056) can be attenuated, or expression of the glycerol metabolism genes (EP 1715055 A) such as glpA, glpB, glpC, glpD, glpE, glpF, glpG, glpK, glpQ, glpT, glpX, tpiA, gldA, dhaK, dhaL, dhaM, dhaR, fsa, and talC genes can be enhanced.

Mutant yeaS Gene

The bacterium in accordance with the presently disclosed subject matter can be obtained by modifying a bacterium belonging to the family Enterobacteriaceae which is able to produce an L-amino acid as described above to have a specific mutation in the yeaS. However, after a bacterium is modified as described above, and the ability to produce an L-amino acid can be imparted. The "specific mutation" will be explained later. The yeaS gene not having the specific mutation can be called "wild-type yeaS gene". A yeaS gene not having the specific mutation but having another mutation is also a "wild-type yeaS gene", so long as it has an activity of improving an L-cysteine-producing ability of a bacterium belonging to the family Enterobacteriaceae as compared to a non-modified strain when expression thereof is increased in the bacterium.

The yeaS gene will be explained below.

Specific examples of the yeaS gene include a gene of the nucleotide sequence of SEQ ID NO: 1. A nucleotide sequence of a wild-type yeaS gene of an *Escherichia coli* strain is shown in SEQ ID NO: 1. The amino acid sequence encoded by this gene is shown in SEQ ID NO: 2.

Although it is known that the ability to produce various amino acids can be improved by enhancing expression of the yeaS gene (FEBS Lett., 579, 4629-4634 (2005)), the relationship between the yeaS gene and L-cysteine production is not known. The inventors of the present invention found that L-cysteine-producing ability was improved by enhancing expression of the yeaS gene.

The yeaS gene can also encode a protein having a sequence corresponding to the aforementioned amino acid sequence, but which includes substitutions, deletions, insertions, or additions of one or several amino acid residues at one or several positions, so long as the gene encodes a protein having an activity of improving an L-cysteine-producing ability in a bacterium belonging to the family Enterobacteriaceae when overexpressed in the bacterium as compared to a bacterium in which the protein is not overexpressed. The protein having the aforementioned amino acid sequence can include substitutions, deletions, insertions, or additions of one or several amino acid residues, but maintains 70% or more, 80% or more, or even 90% or more, of the activity of improving an L-cysteine-producing ability as compared to the protein having the aforementioned amino acid sequence, but which does not include the substitutions, deletions, insertions, or additions of one or several amino acid residues. Although the number of the "one or several" amino acid residues can differ depending on their position in the three-dimensional structure or the types of amino acid residues of the proteins, it can be 1 to 20, 1 to 10, or even 1 to 5.

The aforementioned substitutions, deletions, insertions, or additions of one or several amino acid residues can be a conservative mutation that preserves the normal function of the protein. The conservative mutation is typically a conservative substitution. The conservative substitution is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion etc. can be the result of a naturally-occurring mutation (mutant or variant) due to an individual difference, a difference of species, or the like of a bacterium from which the gene is derived.

Specific examples of gene coding for a YeaS protein having an activity of improving an L-amino acid-producing ability of a host cell, and having an amino acid sequence including substitutions, deletions, insertions or additions of one or several amino acid residues include genes coding for a YeaS protein having the sequence of SEQ ID NO: 2, but including at least one or more mutations such as a mutation for substitution of a glycine residue for the tryptophan residue at position 11, a mutation for substitution of an arginine residue for the lysine residue at position 33, a mutation for substitution of a valine residue for the isoleucine residue at position 52, a mutation for substitution of a serine residue for the phenylalanine residue at position 59, a mutation for substitution of a glutamine residue for the leucine residue at position 60, a mutation for substitution of a glutamic acid residue for the valine residue at position 65, a mutation for substitution of an alanine residue for the threonine residue at position 72, a mutation for substitution of a serine residue for the asparagine residue at position 77, a mutation for substitution of an isoleucine residue for the phenylalanine residue at position 85, and a mutation for substitution of a phenylalanine residue for the tyrosine residue at position 86. These mutations are presumed to be silent mutations since the activity in Example 2 described later is not reduced. The conservative mutation is not limited to these, and a gene coding for a YeaS protein having an amino acid sequence including substitutions of one or several amino acid residues but maintaining an activity of improving an L-amino acid-producing ability when expression thereof is increased in a bacterium belonging to the family Enterobacteriaceae can be obtained from yeaS genes artificially introduced with random mutations, as shown in Example 2.

Furthermore, the gene having such a conservative mutation as described above can be a gene encoding a protein showing a homology of 80% or more, 90% or more, 95% or more, 97% or more, or even 99% or more, to the entire encoded amino acid sequence, and having an activity of improving an L-amino acid-producing ability of a bacterium belonging to the family Enterobacteriaceae when the protein is overexpressed as compared to a bacterium in which the protein is not overexpressedSequence information of genes coding for a protein homologous to such YeaS (YeaS homologues) can be easily obtained from databases opened to public by BLAST searching or FASTA searching using the wild-type yeaS gene of the aforementioned *Escherichia coli* strain as a query sequence, and a yeaS homologue can be obtained by using oligonucleotides produced based on such known gene sequences as primers. The term "homology" can mean "identity".

The yeaS gene can be a gene which hybridizes with a sequence complementary to the aforementioned nucleotide sequences or a probe that can be prepared from the aforementioned nucleotide sequences under stringent conditions, so long as it is a gene which encodes a protein having an activity of improving an L-amino acid-producing ability of a bacterium belonging to the family Enterobacteriaceae when expression thereof is increased in the bacterium. Examples of the "stringent conditions" include conditions of washing at 60° C., 1×SSC, 0.1% SDS, preferably 60° C., 0.1×SSC, 0.1% SDS, once or preferably twice or three times.

The probe used for the aforementioned hybridization can have a partial sequence of a complementary sequence of the gene. Such a probe can be prepared by PCR using oligonucleotides prepared based on the known nucleotide sequences of the gene as primers, and a DNA fragment containing these sequences as the template. When a DNA fragment of a length of about 300 bp is used as the probe, the conditions of washing after hybridization can be, for example, 50° C., 2×SSC, and 0.1% SDS.

The activity of a protein which results in improving an L-amino acid-producing ability of a bacterium belonging to the family Enterobacteriaceae when the protein is overexpressed in the bacterium as compared to a bacterium in which the protein is not overexpressed can mean an activity of causing production and accumulation of an increased amount of an L-amino acid such as L-cysteine in a medium as compared to a non-modified strain such as a wild-type or parent strain, for example, an activity of imparting an ability to accumulate an L-amino acid in a medium in an amount of 0.1 g/L or more, 0.2 g/L or more, or even 0.3 g/L or more, to a bacterium belonging to the family Enterobacteriaceae when the protein is overexpressed in the bacterium.

Whether a protein has an activity of improving an L-amino acid-producing ability of a bacterium belonging to the family Enterobacteriaceae as compared to a bacterium in which the protein is not overexpressed in the bacterium can be confirmed by preparing a bacterium in which expression of the gene coding for the protein is increased from a wild-type or parent strain, culturing this bacterium in a medium, and quantifying the amount of L-amino acid which accumulates in the medium. When the L-amino acid is L-cysteine, examples of the wild-type or parent strain include an *E. coli* MG1655 strain in which a gene coding for a mutant SAT desensitized to feedback inhibition is enhanced.

It can also be easily confirmed that a certain protein has an activity of improving an L-amino acid-producing ability of a bacterium belonging to the family Enterobacteriaceae as compared to a non-modified strain when expression thereof is increased in the bacterium by confirming that growth of a bacterium in which expression of the gene is increased is more favorable as compared to a wild-type or parent strain in a medium containing an L-amino acid at a higher concentration as compared to a wild-type or parent strain, i.e., examining L-amino acid resistance of the strain. When the L-amino acid is L-cysteine, it can be confirmed by, specifically, inoculating the bacterium in a medium containing about 0.1 to 10 mM L-cysteine, measuring diameters of colonies after an appropriate period of 10 to 120 hours, and confirming that the value thereof is larger than that observed for the wild type or parent strain. The inventors of the present invention found that there was considerable correlation between the activity of improving L-cysteine-producing ability of a host cell as compared to a non-modified strain and the L-cysteine resistance.

The "specific mutation" in the mutant yeaS gene can be one or more of the following:

(I) replacing the threonine residue at position 28 with an amino acid residue other than threonine in the protein encoded by the yeaS gene, (II) replacing the phenylalanine residue at position 137 with an amino acid residue other than phenylalanine in the protein encoded by the yeaS gene, (III) replacing the leucine residue at position 188 with an amino acid residue other than leucine in the protein encoded by the yeaS gene.

Specific examples of the mutations can be the following:

(i) substituting an asparagine residue for the threonine residue at position 28, (ii) substituting a serine, glutamine, alanine, histidine, cysteine or glycine residue for the phenylalanine residue at position 137, (iii) substituting a glutamine residue for the leucine residue at position 188.

The mutation one of the aforementioned mutations, or an arbitrary combination of any of the mutations.

An example is the substitution of a serine or glutamine residue for the phenylalanine residue at position 137.

The positions 28, 137, and 188 in the mutations of (I) to (III) are not necessarily absolute positions from the N-terminus of the protein encoded by a yeaS gene (YeaS), but can indicate relative positions with respect to the amino acid sequence of SEQ ID NO: 2. For example, if one amino acid residue is deleted from the YeaS protein having the amino acid sequence shown in SEQ ID NO: 2 at a position upstream of position 28, the position 28 then becomes position 27. Even in such a case, the amino acid residue of the position 27 is still regarded as an amino acid residue of the "position 28". Absolute position of amino acid substitution can be determined by alignment of amino acid sequence of an objective YeaS protein and the amino acid sequence of SEQ ID NO: 2.

The mutations of (I) to (III) can be introduced into a yeaS gene by introducing a predetermined mutation at a codon corresponding to the mutation of a wild-type yeaS gene by, for example, site-specific mutagenesis method, overlap extension method, or the like. Although the codon used after the introduction of the mutation is not particularly limited, so long as it codes for a predetermined amino acid, it is preferable to use a codon frequently used in the objective bacterium belonging to the family Enterobacteriaceae.

The mutations of (I) to (III) can be introduced into the yeaS gene on the chromosome of bacterium by substituting a mutant yeaS gene containing a mutation point or a fragment thereof for a corresponding portion of the yeaS gene on the chromosome. It can also be attained by transforming the bacterium with the mutant yeaS gene or a vector containing the gene. In this case, the mutant yeaS gene can be introduced into a chromosome or a plasmid. The wild-type yeaS gene can continue to be carried on the chromosome, or deleted.

Furthermore, one or two or more copies of the mutant yeaS gene can be contained in the bacterium. Furthermore, the promoter for expressing the mutant yeaS gene can be a promoter of a wild-type yeaS gene or another promoter such as lac promoter, trp promoter and trc promoter.

Examples of the vector used for transformation include a plasmid which can autonomously replicates in a chosen microorganism. Examples of plasmid autonomously replicable in a microorganism belonging to the family Enterobacteriaceae include pUC19, pUC18, pBR322, RSF1010, pHSG299, pHSG298, pHSG399, pHSG398, pSTV28, pSTV29, pTWV228, pTWV229 (pHSG, pSTV and pTWV series vectors are available from Takara Bio), pMW119, pMW118, pMW219, pMW218 (pMW series vectors are available from Nippon Gene), and so forth. Furthermore, plasmids for coryneform bacteria include pAM330 (Japanese Patent Laid-open No. 58-67699), pHM1519 (Japanese Patent Laid-open No. 58-77895), pSFK6 (Japanese Patent Laid-open No. 2000-262288), pVK7 (U.S. Patent Published Application No. 2003/0175912), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491), and so forth.

Examples of transformation methods include treating recipient cells with calcium chloride to increase permeability for DNA, which has been reported for *Escherichia coli* K-12 (Mandel, M. and Higa, A., J. Mol. Biol., 1970, 53:159-162), preparing competent cells from cells which are at the growth phase, followed by transformation with DNA, which has been reported for *Bacillus subtilis* (Duncan, C. H., Wilson, G. A. and Young, F. E., 1977, Gene, 1:153-167), and so forth. Alternatively, a method of making DNA-recipient cells into protoplasts or spheroplasts, which can easily take up recombinant DNA, followed by introducing a recombinant DNA into the cells, which is known to be applicable to *Bacillus subtilis*, actinomycetes and yeasts (Chang, S, and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Sci., USA, 75:1929-1933) can also be employed. In addition, transformation of microorganisms can also be performed by the electric pulse method (Japanese Patent Laid-open No. 2-207791).

The mutant yeaS gene can also be introduced into a bacterium by introduction into a chromosome of the host microorganism, as described later for the mutant yeaS gene.

The mutant yeaS gene can be introduced into a chromosome of a microorganism by a method of randomly introducing it into a chromosome using a transposon or Mini-Mu (Japanese Patent Laid-open No. 2-109985, U.S. Pat. No. 5,882, 888, EP 805867 B1), or by homologous recombination using a sequence present on a chromosomal DNA in a multiple copy number as a target. As a sequence present on a chromosomal DNA in a multiple copy number, repetitive DNA, and inverted repeat located at the end of a transposable element can be used. Alternatively, by using the Red driven integration method (WO2005/010175), it is also possible to introduce an objective gene into a chromosome. Moreover, an objective gene can also be introduced into a chromosome by transduction using phages such as P1 phage, or by using a conjugative transfer vector. Furthermore, it is also possible to introduce a mutant yeaS gene using a gene unnecessary for production of an objective substance as a target, as described in WO03/040373. One or plural copies of a mutant yeaS gene cab be introduced into a target sequence by such methods.

Transfer of an objective gene on a chromosome can be confirmed by Southern hybridization using a probe having a sequence complementary to the objective gene or a part thereof, PCR using primers prepared on the basis of the sequence of the objective gene, and so forth.

<2> Method for Producing L-Amino Acid

An L-amino acid can be produced by culturing a bacterium in accordance with the presently disclosed subject matter obtained as described above in a medium, and collecting the L-amino acid from the medium. The L-amino acid can be a derivative of the L-amino acid. When L-amino acid is L-cysteine, examples of derivative of L-cysteine include S-sulfocysteine, a thiazolidine derivative, a hemithioketal corresponding to the thiazolidine derivative, and so forth, as described above.

Examples of the medium used for the culture include ordinary media containing a carbon source, nitrogen source, sulfur source, inorganic ions, and other organic components as required.

As the carbon source, saccharides such as glucose, fructose, sucrose, glycerol, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the sulfur source, inorganic sulfur compounds, such as sulfates, sulfites, sulfides, hyposulfites and thiosulfates can be used.

As organic trace amount nutrients, it is desirable to add required substances such as vitamin $B_1$, yeast extract and so forth in appropriate amounts. Other than these, potassium phosphate, magnesium sulfate, iron ions, manganese ions and so forth are added in small amounts.

The culture is preferably performed under aerobic conditions for 30 to 90 hours. The culture temperature is preferably controlled to be at 25° C. to 37° C., and pH is preferably controlled to be 5 to 8 during the culture. For pH adjustment, inorganic or organic acidic or alkaline substances, ammonia gas and so forth can be used.

For collection of L-amino acid from the medium after completion of the culture, any special method is not required. The L-amino acid collected can contain bacterial cells, medium components, moisture, and by-product metabolites of the microorganism in addition to the L-amino acid. Purity of the collected L-amino acid is, for example, 50% or higher, 85% or higher, or even 95% or higher (U.S. Pat. No. 5,431,933, Japanese Patent Publication No. 1-214636, U.S. Pat. Nos. 4,956,471, 4,777,051, 4,946,654, 5,840,358, 6,238,714, U.S. Patent Published Application No. 2005/0025878).

The L-amino acid can be collected by a combination of conventionally known ion-exchange resin method (Nagai, H. et al., Separation Science and Technology, 39(16), 3691-3710), membrane separation method (Japanese Patent Laid-open Nos. 9-164323 and 9-173792), crystallization method (WO2008/078448, WO2008/078646), and other methods.

L-Cysteine obtained as described above can be used for production of L-cysteine derivatives. The L-cysteine derivatives include methylcysteine, ethylcysteine, carbocistein, sulfocysteine, acetylcysteine, and so forth.

Furthermore, when a thiazolidine derivative of L-cysteine is accumulated in the medium, L-cysteine can be produced by changing the reaction equilibrium between the thiazolidine derivative and L-cysteine to the L-cysteine side. Furthermore, when S-sulfocysteine is accumulated in the medium, it can be converted into L-cysteine by reduction using a reducing agent such as dithiothreitol.

EXAMPLES

Hereinafter, the present invention will be explained more specifically with reference to examples.

Example 1

L-Cysteine Production Increasing Effect of Enhancement of Wild-Type YeaS

In order to investigate the effect of enhancing expression of a wild-type yeaS gene in *P. ananatis* on L-cysteine production, a strain introduced with the gene cysE5 coding for a mutant SAT (U.S. Patent Published Application No. 2005/0112731) and having an increased copy number of the yeaS gene was constructed.

First, a plasmid for constructing the aforementioned strain was constructed. The method for it is described below.

By PCR using the chromosomal DNA of *E. coli* MG1655 (ATCC No. 47076) as a template as well as P1 (agctgagtcg acccccagga aaaattggtt aataac, SEQ ID NO: 20) and P2 (agctgagcat gcttccaact gcgctaatga cgc, SEQ ID NO: 21) as primers, a DNA fragment containing a promoter region of the nlpD gene (henceforth wild-type nlpD gene promoter is referred to as "Pnlp0") of about 300 bp was obtained. At the 5' and 3' ends of the aforementioned primers, sites for the restriction enzymes SalI and PaeI were designed, respectively. The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and 72° C. for 5 minutes as the final cycle. The obtained fragment was treated with SalI and PaeI, and inserted into pMIV-5JS (Japanese Patent Laid-open No. 2008-99668) at the SalI-PaeI site to obtain a plasmid pMIV-Pnlp0. The nucleotide sequence of the PaeI-SalI fragment of the Pnlp0 promoter inserted into this pMIV-Pnlp0 plasmid was as shown in SEQ ID NO: 5.

Then, by PCR using the chromosomal DNA of MG1655 as a template, as well as P3 (agctgatcta gaaaacagaa tttgcctggc ggc, SEQ ID NO: 22) and P4 (agctgaggat ccaggaagag tttgtagaaa cgc, SEQ ID NO: 23) as primers, a DNA fragment containing a terminator region of the rrnB gene of about 300 bp was obtained. At the 5' ends of the aforementioned primers, sites for the restriction enzymes XbaI and BamHI were designed, respectively. The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 59° C. for 20 seconds, and 72° C. for 15 seconds, and 72° C. for 5 minutes as the final cycle. The obtained fragment was treated with XbaI and BamHI, and inserted into pMIV-Pnlp0 at the XbaI-BamHI site to obtain a plasmid pMIV-Pnlp0-ter.

Then, by PCR using the chromosomal DNA of the MG1655 strain as a template, as well as P5 (agctgagtcg acgtgttcgc tgaatacggg gt, SEQ ID NO: 24) and P6 (agctgatcta gagaaagcat caggattgca gc, SEQ ID NO: 25) as primers, a DNA fragment of about 700 bp containing the yeaS gene was obtained. At the 5' ends of the aforementioned primers, sites for the restriction enzymes SalI and XbaI were designed, respectively. The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and 72° C. for 5 minutes as the final cycle. The obtained fragment was treated with SalI and XbaI, and inserted into pMIV-Pnlp0-ter at the SalI-XbaI site to obtain a plasmid pMIV-Pnlp0-YeaS3. As described above, a yeaS expression unit comprising the pMIV-5JS vector on which the nlpD promoter, the yeaS gene, and the rrnB terminator were ligated in this order was constructed.

In order to modify the −10 region of the nlpD promoter to make it a stronger promoter, the −10 region was randomized by the following method. The nlpD promoter region contains two of regions presumed to function as promoters (FIG. 1), and they are indicated as pnlp1 and pnlp2, respectively, in the drawing. By PCR using the plasmid pMIV-Pnlp0 as a template as well as P1 and P7 (atcgtgaaga tcttttccag tgttnannag ggtgccttgc acggtnatna ngtcactgg ("n" means that the corresponding residue can be any of a, t, g and c), SEQ ID NO: 26) as primers, a DNA fragment in which the −10 region contained in the 3' end sequence of the nlpD promoter (referred to as −10(Pnlp1)) was randomized was obtained (FIG. 1). The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and 72° C. for 5 minutes as the final cycle.

Furthermore, by PCR using the plasmid pMIV-Pnlp0 as a template as well as P2 and P8 (tggaaaagat cttcannnnn cgctgacctg cg ("n" means that the corresponding residue can be any of a, t, g and c), SEQ ID NO: 27) as primers, a DNA fragment in which the −10 region contained in the 5' end sequence of the nlpD promoter (referred to as −10(Pnlp2)) was randomized was similarly obtained (FIG. 1). The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and 72° C. for 5 minutes as the final cycle.

The obtained 3' and 5' end fragments could be ligated using the BglII sites designed in the primers P7 and P8, and the full length of the nlpD promoter in which two −10 regions were randomized could be constructed by such ligation. By PCR using this fragment as a template as well as P1 and P2 as primers, a DNA fragment corresponding to a modified type nlpD promoter of the full length was obtained. The PCR cycle was as follows: 95° C. for 3 minutes, then 2 cycles of 95° C. for 60 seconds, 50° C. for 30 seconds, and 72° C. for 40 seconds, 12 cycles of 94° C. for 20 seconds, 60° C. for 20 seconds, and 72° C. for 15 seconds, and 72° C. for 5 minutes as the final cycle.

The amplified fragment was treated with the restriction enzymes SalI and PaeI, for which sites were designed in the 5' ends of the primers, and inserted into the plasmid pMIV-Pnlp0-YeaS3 similarly treated with SalI and PaeI to substitute the mutant Pnlp for the wild-type nlpD promoter region (Pnlp0) on the plasmid. From such plasmids, one having the promoter sequence (Pnlp8) shown in FIG. 1 was selected, and designated pMIV-Pnlp8-YeaS7. The nucleotide sequence of the PaeI-SalI fragment of the Pnlp8 promoter inserted into this plasmid was as shown in SEQ ID NO: 6. In the same manner, a DNA fragment of the nlpD promoter region containing a mutation was inserted into the plasmid pMIV-Pnlp0-ter treated with SalI and PaeI to substitute the mutant Pnlp for the nlpD promoter region (region of Pnlp0) on the plasmid. One of them was designated pMIV-Pnlp23-ter. The nucleotide sequence of the PaeI-SalI fragment of the Pnlp23 promoter inserted into this plasmid was as shown in SEQ ID NO: 7.

Then, from pMW-Pomp-cysE5 (WO2005/007841), the Pomp-cysE5 cassette portion was excised with PaeI and SacI, and inserted into the same site of pMIV-5JS to construct pMIV-Pomp-CysE5. pMW-Pomp-cysE5 was a plasmid obtained by inserting the cysE5 gene coding for the mutant SAT ligated with the ompC gene promoter into pMW118. From pACYC184 (GenBank/EMBL accession number X06403, available from NIPPON GENE), the tetracycline resistance gene was excised with XbaI and Eco88I, and this gene fragment was treated with the Klenow fragment, and then inserted into pMIV-Pomp-CysE5 at the PvuI site to construct pMT-Pomp-CysE5. Then, pMIV-Pnlp8-YeaS7 was digested with HindIII, blunt-ended with the Klenow fragment, and then digested with NcoI to excise a fragment containing the cassette of the Pnlp8-YeaS-rrnB terminator and the chloramphenicol resistance marker. This fragment was ligated with a SmaI and NcoI digestion fragment of pMT-Pomp-CysE5 similarly having pMIV-5JS as the backbone to construct pMT-EY2. pMT-EY2 is a plasmid having the Pnlp8-YeaS-rrnB terminator cassette and the Pomp-CysE5 cassette on one plasmid.

In order to investigate the effect of enhancing expression of the wild-type yeaS gene on L-cysteine production, pMT-Pomp-CysE5 and pMT-EY2 constructed by the methods described above were introduced into the *P. ananatis* SC17 strain (U.S. Pat. No. 6,596,517), and L-cysteine-producing ability of the obtained transformants was evaluated.

An L-cysteine production medium (composition: 15 g/L of ammonium sulfate, 1.5 g/L of potassium dihydrogenphosphate, 1 g/L of magnesium sulfate heptahydrate, 0.1 g/L of tryptone, 0.05 g/L of yeast extract, 0.1 g/L sodium chloride, 20 g/L of calcium carbonate, 40 g/L of glucose, and 20 mg/L of tetracycline) was used for the culture.

The L-cysteine production culture was performed by the following procedure. The SC17/pMT-PompCysE5 strain and SC17/pMT-EY2 strain were each applied on the LB agar medium to perform preculture overnight at 34° C., then cells corresponding to ⅛ of the plate were scraped with an inoculation loop, inoculated into 2 ml of the L-cysteine production medium contained in a large test tube (internal diameter: 23 mm, length: 20 cm), and cultured at 32° C. with shaking at 220 to 230 rpm, and the culture was terminated after two days. L-Cysteine produced in the medium was quantified by the method described by Gaitonde, M. K. (Biochem. J., 1967 Aug., 104(2):627-33). As shown in Table 1, it was found that enhancement of expression of the yeaS gene had an effect of increasing L-cysteine production amount. The L-cysteine quantified above include L-cysteine as well as L-cystine, and derivatives thereof such as S-sulfocysteine, thiazolidine derivatives, hemithioketals, and mixtures thereof, and the same shall apply to L-cysteine quantified in the examples unless particularly indicated.

TABLE 1

Effect of enhancement of yeaS in SC17 strain

| Plasmid introduced | L-Cysteine (g/L) |
|---|---|
| pMT-CysE5 | 0.20 |
| pMT-EY2 | 1.54 |

Example 2

Acquisition of Mutant yeaS Gene and L-Cysteine Production-Increasing Effect

Then, in order to obtain a mutant having a higher activity of improving L-cysteine producing ability of a host cell as compared to a wild-type YeaS, random mutations were artificially introduced into the yeaS gene by error-prone PCR.

(1) Error-Prone PCR of yeaS and Preparation of Mutation Introduction Library

First, conditions of error-prone PCR for introducing 1 to 3 mutations into the yeaS gene were examined on the basis of prior findings (Evert Bokma et al., FEBS Letters, 580: 5339-5343 (2006); Zao et al., Nat. Biotechnol. Mar., 16(3): 258-61 (1998)). As the DNA polymerase, taq polymerase (produced by QIAGEN) was used, and the composition of the reaction mixture consisted of 10 mM Tris-HCl (pH 8.3), 50 mM KCl, 7 mM $MgCl_2$, 0.2 mM dGTP and dATP, 1 mM dCTP and dTTP, and 12.5 μM $MnCl_2$. As the primers, P9 (catgccatgg tcgctgaata cggggttctg, SEQ ID NO: 28) and P10 (aactgcagtc aggattgcag cgtcgcc, SEQ ID NO: 29), to which NcoI site and the PstI site were added, respectively, were used, and the amplification was performed with a PCR cycle consisting of 94° C. for 5 minutes, then 50 cycles of 94° C. for 30 seconds, 50° C. for 45 seconds, and 72° C. for 45 seconds, and 72° C. for 7 minutes as the final cycle. The reaction was performed in the reaction mixture divided into 16 of independent PCR tubes to obviate biased mutation.

The amplified fragment was digested with NcoI and PstI, ligated with pTrc99-Kmr treated with the same enzymes, and used to transform the *E. coli* JM109 strain. pTrc99-Kmr was prepared by treating pTrc99A (GenBank/EMBL accession number M22744, available from Amersham Bioscience) with the restriction enzyme DraI to removes the ampicillin resistance gene, and inserting a kanamycin resistance gene into that site. The kanamycin resistance gene was obtained by amplifying pACYC177 (GenBank/EMBL accession number X06402, available from NIPPON GENE) as a template by PCR using P11 (aaagccacgt tgtgtctcaa aatc, SEQ ID NO: 30) and P12 (ggtgttgctg actcatacca ggc, SEQ ID NO: 31) as primers with a program of 94° C. for 1 minute, then 30 cycles of 94° C. for 30 seconds, 55° C. for 30 seconds, and 72° C. for 75 seconds, and 72° C. for 5 minutes as the final cycle.

Selection of the aforementioned transformants were performed on the LB agar medium containing 25 mg/L of kanamycin, and it was confirmed that the transformants had yeaS introduced with a mutation by performing PCR using a strain randomly picked up from the obtained colonies as a template as well as P13 (gacaattaatcatccggctc g, SEQ ID NO: 32) and P14 (tttatcagac cgcttctgcg, SEQ ID NO: 33) as primer with a program of 94° C. for 5 minutes, then 30 cycles of 98° C. for 5 seconds, 60° C. for 10 seconds, and 72° C. for 45 seconds, and 72° C. for 2 minutes as the final cycle. All the colonies on the plate were scraped, and plasmids were collected with WizardR Plus Midipreps DNA Purification System (Promega) to obtain a library.

(2) Screening of Mutant yeaS Based on L-Cysteine Resistance as Marker

The obtained library was introduced into the MG1655 strain by electroporation, and the cells were applied on an M9 selection plate (12.8 g/L of disodium hydrogenphosphate heptahydrate, 3.0 g/L of potassium dihydrogenphosphate, 0.5 g/L of sodium chloride, 1.0 g/L of ammonium chloride, 2 mM magnesium sulfate, 0.4% of glucose, 0.1 mM potassium chloride, 25 mg/L of kanamycin, and 1.5% of agarose) containing 3 mM or 6 mM L-cysteine. After this selection plate was incubated at 37° C. for 2 days, slightly less than 100 of resistant strains were obtained when the M9 selection plate contained 6 mM L-cysteine, and 200 to 300 resistant strains were obtained when the plate contained 3 mM L-cysteine. Single colony isolation was performed for 80 strains obtained on the plate containing 6 mM L-cysteine and 12 strains obtained on the plate containing 3 mM L-cysteine, and DNA fragments containing the yeaS gene region on the plasmids were amplified by PCR using these colonies as templates as well as P13 and P14 as primers with a program of 94° C. for 5 minutes, then 30 cycles of 98° C. for 5 seconds, 60° C. for 10 seconds, and 72° C. for 45 seconds, and 72° C. for 2 minutes as the final cycle. The nucleotide sequences of those fragments were determined using P13 as a sequencing primer to confirm the mutation-introduced sites in the yeaS gene. The clones of which sequence could be determined were divided into groups of those showing the same results, then plasmids were extracted from typical clones and introduced into the L-cysteine-producing bacterium mentioned below, and the bacterium was evaluated by culture. Among the obtained clones, considerable number of them contained the T28N mutation, and many double and triple mutant strains into which other mutations were simultaneously introduced together with T28N as shown in Table 2 were obtained. Moreover, plural clones containing the F137S mutation were also obtained. Furthermore, clones independently having the L188Q mutation were also obtained.

(3) Construction of L-Cysteine-Producing Bacterium for Confirming the Effect of Mutant yeaS (1) (Introduction of cysE5 and Mutant yeaS into *P. ananatis* SC17 Strain)

pMT-EY2 described above has the attachment sites of Mu phage originated from pMIV-5JS (Japanese Patent Laid-open No. 2008-99668). By allowing this plasmid to coexist with the helper plasmid pMH10 having Mu transposase (Zimenkov D. et al., Biotechnologiya and (in Russian), 6, 1-22 (2004)) in the same cell, the cassette of PompC-cysE5-Pnlp8-YeaS-rrnB terminator including the chloramphenicol resistance marker located between the attachment sites of Mu phage on this pMT-EY2 plasmid can be inserted into the chromosome of the *P. ananatis* SC17 strain (U.S. Pat. No. 6,596,517). Furthermore, since the chloramphenicol resistance marker located on the pMT-EY2 plasmid exists between two attachment sites of λ phage (λattR and λattL), the chloramphenicol resistance marker can be excised and removed by the method described later.

First, an SC17 strain introduced with pMH10 by electroporation was selected by overnight culture at 30° C. on the LB agar medium containing 20 mg/L of kanamycin. The obtained transformant was cultured at 30° C., and pMT-E2 was further introduced into this strain by electroporation. This strain transformed with both pMH10 and pMT-EY2 was given a heat shock with the conditions of 42° C. for 20 minutes, and colonies of chloramphenicol resistant strains were selected on the LB agar medium containing 20 mg/L of chloramphenicol. The culture temperature for this selection was 39° C. As described above, about 50 clones were obtained, and curing of pMH10 and pMT-EY2 was performed by culturing each clone at 39° C. for 48 hours on the LB agar medium. A strain showing chloramphenicol resistance due to the insertion of the cassette on the chromosome and showing kanamycin and ampicillin sensitivities due to the curing of both the plasmids was obtained. Furthermore, it was confirmed that the objective cassette was inserted in the chromosome of the obtained strain by PCR using the chromosomal DNA of this strain as a template as well as P1 and P6 as primers. All the obtained clones were designated EY01 to EY50, respectively, and L-cysteine production culture was performed by using the EY01 to EY50 strains. For the culture, the method described in Example 1 mentioned above was used. The EY19 strain was selected, which was a clone that produced L-cysteine in the largest amount as a result of the culture.

The chloramphenicol resistance marker introduced into the EY19 strain was removed with an excision system derived from λ phage. Specifically, the EY19 strain was transformed with pMT-Int-Xis2 (WO2005/010175) carrying the Int-Xis gene of λ phage, and an EY19(s) strain showing chloramphenicol sensitivity was obtained from the obtained transformants.

(4) Construction of L-Cysteine-Producing Bacterium for Confirming Effect of Mutant yeaS (2) (Preparation of cysPTWA Gene Expression-Enhanced Strain of EY19(s) Strain)

Then, in order to enhance expression of the cysPTWA gene, the promoter located upstream of the cysPTWA gene cluster on the chromosome was replaced with the aforementioned potent promoter Pnlp8. A DNA fragment containing the nlp8 promoter of about 300 bp was obtained by PCR using pMIV-Pnlp8-YeaS7 as a template as well as P1 and P2. The PCR cycle was as follows: 95° C. for 3 minutes, then 2 cycles of 95° C. for 60 seconds, 50° C. for 30 seconds, and 72° C. for 40 seconds, 20 cycles of 94° C. for 20 seconds, 59° C. for 20 seconds, and 72° C. for 15 seconds, and 72° C. for 5 minutes as the final cycle.

The amplified DNA fragment containing nlp8 promoter was treated with the Klenow fragment, inserted into the plasmid pMW118-(λattL-KmR-λattR) (WO2006/093322A2) digested with XbaI and then treated with the Klenow fragment to obtain a plasmid pMW-Km-Pnlp8. By PCR using pMW-Km-Pnlp8 as a template as well as primers P15 (tccgctcacg atttttttca tcgctggtaa ggtcatttat cccccaggaa aaattggtta, SEQ ID NO: 34) and P16 (tttcacaccg ctcaaccgca gggcataacc ggcccttgaa gcctgctttt ttatactaag ttg, SEQ ID NO: 35), a DNA fragment of about 1.6 kb containing the Km-Pnlp8 cassette was amplified. The PCR cycle for this amplification was as follows: 95° C. for 3 minutes, then 2 cycles of 95° C. for 60 seconds, 50° C. for 30 seconds, and 72° C. for 40 seconds, 30 cycles of 94° C. for 20 seconds, 54° C. for 20 seconds, and 72° C. for 90 seconds, and 72° C. for 5 minutes as the final cycle. On both the primers, a sequence serving as a target on the chromosome for inserting an objective fragment by λ-dependent integration (the method called "Red-driven integration" (Proc. Natl. Acad. Sci. USA, 2000, vol. 97, No. 12, pp. 6640-6645)) (in this case, a sequence near the promoter of cysPTWA) was designed. Therefore, if the obtained DNA fragment is inserted into the objective strain by this λ-dependent integration, there is provided a structure that Km-Pnlp8 is inserted immediately before the cysPTWA gene on the chromosome, and the cysPTWA gene is ligated with the nlp8 promoter. The nucleotide sequence of the cysPTWA gene cluster is shown in SEQ ID NO: 12, and the amino acid sequences encoded by the cysP, cysT and cysW genes are shown in SEQ ID NOS: 13 to 15, respectively. The nucleotide sequence of the cysA gene and the amino acid sequence encoded by this gene are shown in SEQ ID NOS: 16 and 17, respectively.

The *P. ananatis* SC17(0)/RSF-Red-TER strain is a host strain for efficiently performing the λ-dependent integration, and it is a strain obtained by introducing the helper plasmid RSF-Red-TER which expresses gam, bet and exo genes (henceforth referred to as "λ Red genes") into the SC17(0) strain, which is a λ Red gene product-resistant *P. ananatis* strain (WO2008/075483). The SC17(0) strain was deposited at the Russian National Collection of Industrial Microorganisms (VKPM), GNII Genetika (address: Russia, 117545 Moscow, 1 Dorozhny proezd. 1) on Sep. 21, 2005 with an accession number of VKPM B-9246. A method for constructing the RSF-Red-TER plasmid is disclosed in detail in WO2008/075483.

The aforementioned SC17(0)/RSF-Red-TER strain was cultured with addition of IPTG for inducing expression of λ Red genes to prepare cells for electroporation. The aforementioned objective DNA fragment was introduced into these cells by electroporation, and a recombinant strain in which the nlp8 promoter was inserted upstream of the cysPTWA gene by λ-dependent integration was obtained by using the kanamycin resistance as a marker. By PCR using the chromosomal DNA of the obtained strain as a template, as well as P17 (ctttgtccct ttagtgaagg, SEQ ID NO: 36) and P18 (agctgatcta gaagctgact cgagttaatg gcctcccaga cgac, SEQ ID NO: 37) as primers, it was confirmed that the objective structure, Km-Pnlp8-cysPTWA, was formed, and this strain was designated SC17(0)-Pnlp8-PTWA strain.

Then, the chromosomal DNA of the SC17(0)-Pnlp8-PTWA strain was purified, and 10 μg of this chromosomal DNA was introduced into the EY19(s) strain by electroporation to obtain a kanamycin resistant strain. Amplification was performed by PCR using the chromosomal DNA of the obtained strain as a template as well as P17 and P18 as primers to confirm that the structure of Km-Pnlp8-cysPTWA had been introduced into the chromosome of the EY19(s) strain. The strain obtained as described above was designated EYP197 strain. Furthermore, the kanamycin resistance marker was removed from the chromosome by using pMT-Int-Xis2 as described above, and the strain that became kanamycin sensitive was designated EYP197(s) strain.

(5) Construction of L-Cysteine-Producing Bacterium for Confirming Effect of Mutant yeaS (3) (Preparation of Mutant 3-Phosphoglycerate Dehydrogenase (serA348) Gene-Carrying Strain of EYP197(s) Strain)

As a gene of 3-phosphoglycerate dehydrogenase to be introduced into the L-cysteine-producing bacterium, the serA348 gene which is a gene coding for 3-phosphoglycerate dehydrogenase of *Pantoea ananatis* and coding for a mutant enzyme including a mutation for substitution of an alanine residue for the asparagine residue at the 348th position (N348A) (J. Biol. Chem., 1996, 271 (38):23235-8) was constructed by the following method.

The sequence of the wild-type serA gene derived from *Pantoea ananatis* is shown in SEQ ID NO: 10. In order to obtain a 3'-end side DNA fragment of the serA gene into which the aforementioned mutation was introduced, PCR was performed by using the chromosomal DNA of the SC17 strain as a template as well as P19 (agctgagtcg acatggcaaa ggtatcactg gaa, SEQ ID NO: 38) and P20 (gagaacgccc gggcgggctt cgtgaatatg cagc, SEQ ID NO: 39) as primers (95° C. for 3 minutes, then 2 cycles of 95° C. for 60 seconds, 50° C. for 30 seconds, and 72° C. for 40 seconds, 25 cycles of 94° C. for 20 seconds, 60° C. for 20 seconds, and 72° C. for 60 seconds, and 72° C. for 5 minutes as the final cycle). Then, in order to obtain a 5'-end side DNA fragment into which the mutation was introduced, PCR was performed in the same manner by using the chromosomal DNA of the SC17 strain as a template as well as P21 (agctgatcta gacgtgggat cagtaaagca gg, SEQ ID NO: 40) and P22 (aaaac-cgccc gggcgttctc ac, SEQ ID NO: 41) as primers (95° C. for 3 minutes, then 2 cycles of 95° C. for 60 seconds, 50° C. for 30 seconds, and 72° C. for 40 seconds, 20 cycles of 94° C. for 20 seconds, 60° C. for 20 seconds, and 72° C. for 20 seconds, and 72° C. for 5 minutes as the final cycle). Both the obtained PCR fragments were treated with the restriction enzyme SmaI, and ligated by using a DNA ligase to obtain a DNA fragment corresponding to a full length mutant serA gene including the objective mutation (N348A). This DNA fragment was amplified by PCR using it as a template as well as P19 and P21 as primers (95° C. for 3 minutes, then 2 cycles of 95° C. for 60 seconds, 50° C. for 30 seconds, and 72° C. for 40 seconds, 15 cycles of 94° C. for 20 seconds, 60° C. for 20 seconds, and 72° C. for 75 seconds, and 72° C. for 5 minutes as the final cycle). The SalI and the XbaI restriction enzyme sites designed in the P19 and P21 primers were treated with SalI and XbaI, and the fragment was inserted into pMIV-Pnlp8-ter similarly treated with SalI and XbaI to prepare pMIV-Pnlp8-serA348.

The constructed pMIV-Pnlp8-serA348 carried the attachment site of Mu originating in pMIV-5JS (Japanese Patent Laid-open No. 2008-99668). By using this plasmid together with the helper plasmid pMH10 having Mu transposase, the cassette of Pnlp8-serA348-rrnB terminator including the chloramphenicol resistance marker can be inserted into the chromosome of the *P. ananatis* SC17 strain, as described above. The pMIV-Pnlp8-serA348 plasmid and pMH10 were introduced into the SC17(0) strain to obtain a strain in which the cassette of Pnlp8-serA348-rrnB terminator was inserted into the chromosome. By PCR using the primers P1 and P21, it was confirmed that the objective cassette existed in the cells. The 3-phosphoglycerate dehydrogenase activity in cell extracts of about 50 of the obtained clones was measured, and a strain which showed the highest activity was selected, and designated SC17int-serA348 strain. Then, 10 μg of the chromosomal DNA of the SC17int-serA348 strain was introduced into the EYP197(s) strain by electroporation to obtain a chloramphenicol resistant strain, and by PCR using the primers P1 and P21, it was confirmed that the structure of Pnlp8-serA348 had been introduced together with the chloramphenicol resistance marker into the chromosome of the EYP197(s) strain. The strain obtained as described above was designated EYPS1976 strain.

By the aforementioned method for removing marker using pMT-Int-Xis2, the chloramphenicol resistance marker was removed, and the strain that became chloramphenicol sensitive was designated EYPS1976(s) strain.

(6) Construction of L-Cysteine-Producing Bacterium for Confirming Effect of Mutant yeaS (4) (Preparation of O-Acetyl-L-Serine Sulfhydrylase B Gene (cysM) Carrying Strain) of EYPS1976(s) Strain)

First, in order to clone the cysM gene with a promoter of suitable strength, a new promoter was prepared. First, a DNA fragment containing the promoter region of about 180 bp for the nlpD gene was obtained by using the genome of *P. ananatis* SC17 strain as a template. The primers used were P23 (agctgaaagc ttgcatgcac gcgtggcgat ctggcctgac tgc, SEQ ID NO: 42) and P24 (agctgagtcg accccgtggt ggcaaccttt aaaaaactg, SEQ ID NO: 43), and restriction enzyme SalI and PaeI sites were designed at the 5' ends of these primers, respectively. The PCR cycle was as follows: 95° C. for 5 minutes, then 27 cycles of 94° C. for 20 seconds, 59° C. for 20 seconds, and 72° C. for 20 seconds, and 72° C. for 5 minutes as the final cycle.

The nucleotide sequence of the *Escherichia coli* cysM gene and the amino acid sequence encoded by the gene are shown in SEQ ID NOS: 14 and 15, respectively.

The obtained DNA fragment was treated with SalI and PaeI, and inserted into pMIV-Pnlp0-ter similarly treated with SalI and PaeI to obtain pMIV-Pnlp-4-ter. The nucleotide sequence of the PaeI-SalI fragment of the promoter Pnlp4 inserted into the above pMIV-Pnlp-4-ter plasmid was as shown in SEQ ID NO: 8. In a similar manner, by PCR using the plasmid pMIV-Pnlp-4-ter as a template as well as P23 and P25 (agctgagtcg acnnngtggt ggcaaccttt aaaaaactg ("n" means that the corresponding residue can be any of a, t, g and c), SEQ ID NO: 44) as primers (95° C. for 5 minutes, then 27 cycles of 94° C. for 20 seconds, 59° C. for 20 seconds, and 72° C. for 20 seconds, and 72° C. for 5 minutes as the final cycle), a DNA fragment in which the −7 to −9 region contained in the 5'-end side of the nlpD promoter was randomized was prepared, treated with SalI and PaeI, and inserted into pMIV-Pnlp0-ter treated with the same enzymes to obtain pMIV-Pnlp1-ter. The nucleotide sequence of the PaeI-SalI fragment of the Pnlp1 promoter inserted into the above pMIV-Pnlp1 plasmid was as shown in SEQ ID NO: 9. The −7 to −9 region means the positions of 7th to 9th nucleotides on the 5' side from the transcription initiation site of the nlpD promoter.

The cysM gene cloned from the *E. coli* MG1655 strain was incorporated into the above vector. Specifically, the genome of the *E. coli* MG1655 strain as a template was amplified by PCR using P26 (agctgagtcg acgtgagtacatta-gaacaa acaat, SEQ ID NO: 45) and P27 (agctgatcta gaagtctccg atgctattaa tcc, SEQ ID NO: 46) as primers (95° C. for 5 minutes, then 30 cycles of 98° C. for 5 seconds, 50° C. for 10 seconds, and 72° C. for 60 seconds, and 72° C. for 2 minutes as the final cycle). The DNA fragment obtained as described above was treated with restriction enzymes SalI and XbaI, and inserted into pMIV-Pnlp-4-ter and pMIV-Pnlp1-ter treated with the same enzymes to prepare pMIV-Pnlp-4-CysM and pMIV-Pnlp1-CysM, respectively.

By using pMIV-Pnlp-4-CysM and pMIV-Pnlp1-CysM constructed as described above, SC17 strains in which a cassette comprising the cysM gene was inserted in the chromosome were obtained by the aforementioned method using pMH10, respectively. The strains prepared as described above were designated SC17int-4M and SC17int-1M, and the chromosomal DNA was extracted from each of the strains. This chromosomal DNA in an amount of 10 μg was introduced into the EYP1976(s) strain by electroporation to obtain a chloramphenicol resistant strain. The strains prepared as described above were designated EYPSint-4M and EYPSint-1M, respectively, the chloramphenicol resistance marker was removed by the aforementioned method for eliminating marker using pMT-Int-Xis2, and the strains that became chloramphenicol sensitive were designated EYPSint-4M(s) and EYPSint-1M(s) strains, respectively.

(7) Influence of Mutant yeaS on L-Cysteine Production

Some of the mutant yeaS genes prepared in Example 2, (2) mentioned above were selected and introduced into the cysteine-producing bacterium prepared above, EYPSint1M (s), and L-cysteine production culture was performed. The strains to be evaluated were each applied on the LB agar medium, preculture was performed overnight at 34° C., and the cells in about 7 square centimeters of the plate was scraped with an inoculation loop of 10 μl size (NUNC), and inoculated into 2 ml of an L-cysteine production medium (composition: 15 g/L of ammonium sulfate, 1.5 g/L of potassium dihydrogenphosphate, 1 g/L of magnesium sulfate heptahydrate, 0.1 mg/L of thiamine hydrochloride, 1.7 mg/L of ferrous sulfate heptahydrate, 0.15 mg/L of sodium molybdate dihydrate, 0.7 mg/L of cobalt chloride hexahydrate, 1.6 mg/L of manganese chloride tetrahydrate, 0.3 mg/L of zinc sulfate heptahydrate, 0.25 mg/L of copper sulfate pentahydrate, 0.6 g/L of tryptone, 0.3 g/L of yeast extract, 0.6 g/L of sodium chloride, 20 g/L of calcium carbonate, 135 mg/L of L-histidine hydrochloride monohydrate, 4 g/L of sodium thio sulfate, 2 mg/L of pyridoxine hydrochloride, 20 g/L of glucose, 20 mg/L of kanamycin, and 1 mM IPTG) contained in a large test tube (internal diameter: 23 mm, length: 20 cm), so that the cell amounts at the start of the culture should be substantially the same.

Culture was performed at 32° C. with shaking, and terminated when glucose was fully consumed (about 15 to 19 hours), and L-cysteine produced in the medium was quantified. For the test Nos. 1 and 2 mentioned in Table 2, the experiment was performed triplicate to quintuplicate simultaneously, and for the test No. 3, the single experiment was separately performed twice. The averages and standard deviations of the produced L-cysteine amounts obtained as a result are shown in Table 2. It was found that the mutants obtained by the aforementioned screening system were also effective in L-cysteine production culture. On the basis of these results, it was found that at least the mutations at the 28th position and the 188th position were independently effective. Moreover, in plural strains of which L-cysteine-producing ability was improved, triple mutation including the mutation at the 137th position (F137S) was observed. Therefore, it was thought that F137S could be independently involved in the improvement in L-cysteine-producing ability. Moreover, on the basis of various analyses, it is thought that the mutations at the positions 11, 33, 52, 59, 60, 65, 72, 77, 85, and 86 are silent mutations that do not decrease the activity of the YeaS protein.

TABLE 2

Evaluation of strains obtained by screening by culture

| Test No. | Mutation introduced into yeaS | L-Cysteine (g/L) |
|---|---|---|
| 1 | None (WT) | 0.03 ± 0.01 |
| | T28N | 0.27 ± 0.05 |
| | W11G, T28N, Y86F | 0.34 ± 0.06 |
| | T28N, I52V, N77S | 0.36 ± 0.07 |
| 2 | None (WT) | 0.06 ± 0.07 |
| | T28N, V65E, T72A | 0.36 ± 0.09 |
| | K33R, F59S, F137S | 0.90 ± 0.23 |
| | L188Q | 0.30 ± 0.17 |
| 3 | None (WT) | 0.02 ± 0.03 |
| | L60Q, F85I, F137S | 0.79 |

(8) Introduction of Typical Mutation into yeaS Gene and Evaluation of L-Cysteine Resistance of Mutation-Introduced Strain in Liquid Medium By independently introducing the F137S mutation for substitution of a serine residue for the phenylalanine residue at position 137 into the yeaS gene, and further transferring the mutant gene to pSTV29 (Takara Bio), the effect of this mutation alone was examined.

By the overlap PCR method, a vector incorporated with the objective mutation, the proper promoter and terminator of yeas was prepared. A primer P28 containing the mutation (cgataaactg tacgaaagac gacacataga ac, SEQ ID NO: 47) was designed first, and used together with a primer P29 (cgcggatcca gtggtcattt agtgc, SEQ ID NO: 48) as primers, and the genome of *E. coli* MG1655 as a template to amplify a DNA 'fragment 1' by PCR. The program consisted of 94° C. for 5 minutes, then 30 cycles of 98° C. for 5 seconds, 55° C. for 10 seconds, and 72° C. for 45 seconds, and 72° C. for 2 minutes as the final cycle. Furthermore, a DNA 'fragment 2' was amplified by PCR using P9 and P30 (cgcggatcct gtgggatttg aagcatcc, SEQ ID NO: 49) with a program consisting of 94° C. for 5 minutes, then 30 cycles of 98° C. for 5 seconds, 55° C. for 10 seconds, and 72° C. for 60 seconds, and 72° C. for 2 minutes as the final cycle. The obtained fragments were subjected to agarose gel electrophoresis, and the bands were excised and purified. PCR was performed by using a mixture of the DNA 'fragment 1' and the DNA 'fragment 2' diluted 10 times as a template as well as P29 and P30 as primers with a cycle consisting of 94° C. for 5 minutes, then 30 cycles of 98° C. for 5 seconds, 55° C. for 10 seconds, and 72° C. for 1 minute and 10 seconds, and 72° C. for 2 minutes as the final cycle, and the amplified DNA fragment was subjected to agarose gel electrophoresis and then purified in the same manner as that described above.

The purification product and a vector pSTV29 were digested with BamHI, the end of the vector was dephosphorylated with CIAP (Takara Bio), then they were ligated, and JM109 was transformed with the obtained plasmid. The plasmids were extracted from the transformants to obtain pSTV-YeaSF137S carrying a mutant yeaS gene coding for YeaS including substitution of a serine residue for the phenylalanine residue at the 137th position. As a control, pSTV-YeaSWT carrying a wild-type yeaS gene in the same structure as that of pSTV-YeaSF137S was also constructed. However, because it was not necessary to introduce the mutation, the steps of preparing the 'fragment 1' and the 'fragment 2' were omitted, and a fragment containing the yeaS gene was obtained by PCR using the genome of *E. coli* MG1655 as a template as well as P29 and P30 as primers.

Then, L-cysteine resistance of the mutant yeaS gene-introduced strain in a liquid medium was confirmed. *E. coli* MG1655 was transformed with pSTV-YeaSWT and pSTV-YeaSF137S to prepare MG1655/pSTV-YeaSWT and MG1655/pSTV-YeaSF137S. Each of the strains was inoculated into the M9 medium containing 25 mg/L of chloramphenicol and 0.4% of glucose (Sambrook et al., Molecular Cloning, 3rd edition, 2001, Cold Spring Harbor Laboratory Press), and cultured at 37° C. for 24 hours to obtain a seed culture. This seed culture was inoculated in a 1/50 amount to the M9 medium newly prepared. Culture was performed at 37° C. for 14 hours, and then absorbance was measured at 660 nm (OD660). Cell densities of all the test strains were adjusted so that OD660 values of them should be the same as the OD660 value of the strain that showed the lowest OD660 value, and each strain was inoculated in a 1/100 amount to the M9 medium containing 200 μM L-cysteine contained in an L-shaped test tube. Growth of the cells was observed by setting the above L-shaped test tube on an automatically OD measuring culture apparatus BIO-PHOTORECORDER TN-1506 (ADVANTEC) and measuring OD660 every 10 minutes. Difference in L-cysteine resistance of the test strains was evaluated as determined on the basis of quickness of rise of growth in the aforementioned medium. In this culture, as the resistance to L-cysteine was higher, increase of the OD660 value started earlier, and as the resistance to L-cysteine was lower, increase of the OD660 value started more slowly, and the period where apparent growth could not be observed (lag) became longer. The growth curves are shown in FIG. 2. As shown in FIG. 2, the start of increase in the OD660 value of the strain having YeaS having the F137S mutation (YeaSF137S) was earlier compared with that of the strain having the wild-type YeaS (YeaSWT), and it was suggested that L-cysteine resistance was imparted to the former.

(9) Influence of YeaSF137S on L-Cysteine Production

In order to confirm L-cysteine-producing ability of the YeaSF137S-enhanced strain, which showed higher L-cysteine resistance compared with the YeaSWT-enhanced strain in the M9 liquid culture containing L-cysteine, a plasmid ligated with a gene coding for YeaSF137S under the control of the stronger Pnlp8 promoter was constructed. This plasmid was introduced into the L-cysteine-producing bacterium EYPSint-4M, and the effect on L-cysteine production was confirmed. First, by using pSTV-YeaSWT and pSTV-YeaSF137S as templates together with P31 (aagtcgacgt gttcgctgaa tacggggttc tg, SEQ ID NO: 50) and P32 (aatctagatc aggattgcag cgtcgcc, SEQ ID NO: 51) as primers, PCR was performed with a program consisting of 94° C. for 5 minutes, then 30 cycles of 98° C. for 5 seconds, 60° C. for 10 seconds, and 72° C. for 60 seconds, and 72° C. for 2 minutes as the final cycle to amplify the yeaSWT gene fragment and yeaSF137S gene fragment, which were added Sail and XbaI sites at the 5' end and 3' end, respectively. These and the aforementioned pMIV-Pnlp8 were digested with SalI and XbaI, and ligated, and JM109 was transformed with the ligation reaction product. Plasmids were extracted from the transformants, and introduced into the L-cysteine-producing strain EYPSint-4M(s) to obtain EYPSint-4M/pMIV-Pnlp8-YeaSWT and EYPSint-4M/pMIV-Pnlp8-YeaSF137S, respectively. Moreover, EYPSint-4M/pMIV-5JS introduced with only the vector was also prepared as a control, and evaluation by test tube culture was performed by the method described in (3) mentioned above. However, the glucose concentration was changed to 40 g/L, and IPTG was not added.

The results are shown in Table 3. It can be seen that while L-cysteine just slightly increased with enhancement of YeaSWT, enhancement of YeaSF137S markedly increased L-cysteine production. That is, it was considered that YeaSF137S more improved the activity of markedly improving the L-cysteine-producing ability of the host cell compared with a non-modified strain, compared with the conventional YeaSWT.

TABLE 3

Effect of enhancement of YeaSWT and YeaSF137S in cysteine-producing strain

| Plasmid introduced | L-Cysteine (g/L) |
|---|---|
| pMIV-5JS | 0.31 ± 0.14 |
| PMIV-Pnlp8-YeaS$^{WT}$ | 0.41 ± 0.12 |
| pMIV-Pnlp8-YeaS$^{F137S}$ | 0.89 ± 0.06 |

(10) Influence of YeaSF137S on L-Cysteine Production in *E. coli Effect of enhancement of expression of the yeaS gene in E. coli* was examined. A plasmid containing a mutant cysE gene was constructed first. Specifically, a pACYC-DE1 plasmid was constructed according to the method for constructing pACYC-DES described in Japanese Patent Laid-open No. 2005-137369 provided that the step of incorporating a mutant serA5 gene coding for a phosphoglycerate dehydrogenase desensitized to feedback inhibition by serine (described in U.S. Pat. No. 6,180,373) was omitted. While pACYC-DES carried the aforementioned mutant serA5, the gene coding for the mutant SAT desensitized to the feedback inhibition, the cysEX gene, and the ydeD gene coding for the L-cysteine and acetylserine secretion factor (U.S. Pat. No. 5,972,663), pACYC-DE1 constructed above did not contain serA5 mentioned above, but contained cysEX and ydeD. For expression of all the genes, the ompA promoter was used.

As described later, while YeaS was expected to be involved in secretion of L-cysteine, but it is thought that the ydeD product which is a secretion factor of L-cysteine enhances the background when the effect of YeaSF137S is evaluated. Therefore, in order to confirm net effect of the YeaSF137S, the ydeD gene was deleted from pACYC-DEL pACYC-DE1 was treated with MnuI and self-ligated to construct a plasmid in which about 330 bp of the internal sequence of the ydeD gene ORF was deleted. This plasmid not expressing YdeD functioning as an L-cysteine secretion factor, but carrying only CysEX was designated pACYC-E1. *E. coli* MG1655 was transformed with this pACYC-E1 plasmid to prepare an MG1655/pACYC-E1 strain. To this MG1655/pACYC-E1 strain as a host, the pMIV-Pnlp8-yeaSWT plasmid carrying the wild-type yeaS gene, the pMIV-Pnlp8-yeaS137 plasmid carrying the mutant yeaS gene, and pMIV-5JS as a control were introduced by electroporation, respectively. L-Cysteine production of the obtained strains was examined by test tube culture under the same conditions as those of the method described in Example 1 (Table 4). The test tube culture was simultaneously performed in quadruplicate for each strain, and averages of the results are shown in the table. It was found that L-cysteine production amounts were improved by increasing expression amounts of the yeaS gene and the mutant yeaS gene also in *E. coli* having an L-cysteine-producing ability. That is, it was confirmed that the yeaS gene product also showed an activity of improving L-cysteine-producing ability of a host cell compared with a non-modified strain also in *E. coli* having an L-cysteine-producing ability.

TABLE 4

Effect of enhancement of YeaSWT and YeaSF137S in *E. coli* cysteine-producing strain

| Plasmid introduced | L-Cysteine (g/L) |
|---|---|
| pMIV-5JS | 0.44 ± 0.20 |
| pMIV-Pnlp8-YeaS$^{WT}$ | 0.92 ± 0.05 |
| pMIV-Pnlp8-YeaS$^{F137S}$ | 0.98 ± 0.03 |

(11) Characterization of YeaSF137S

Figure 3:
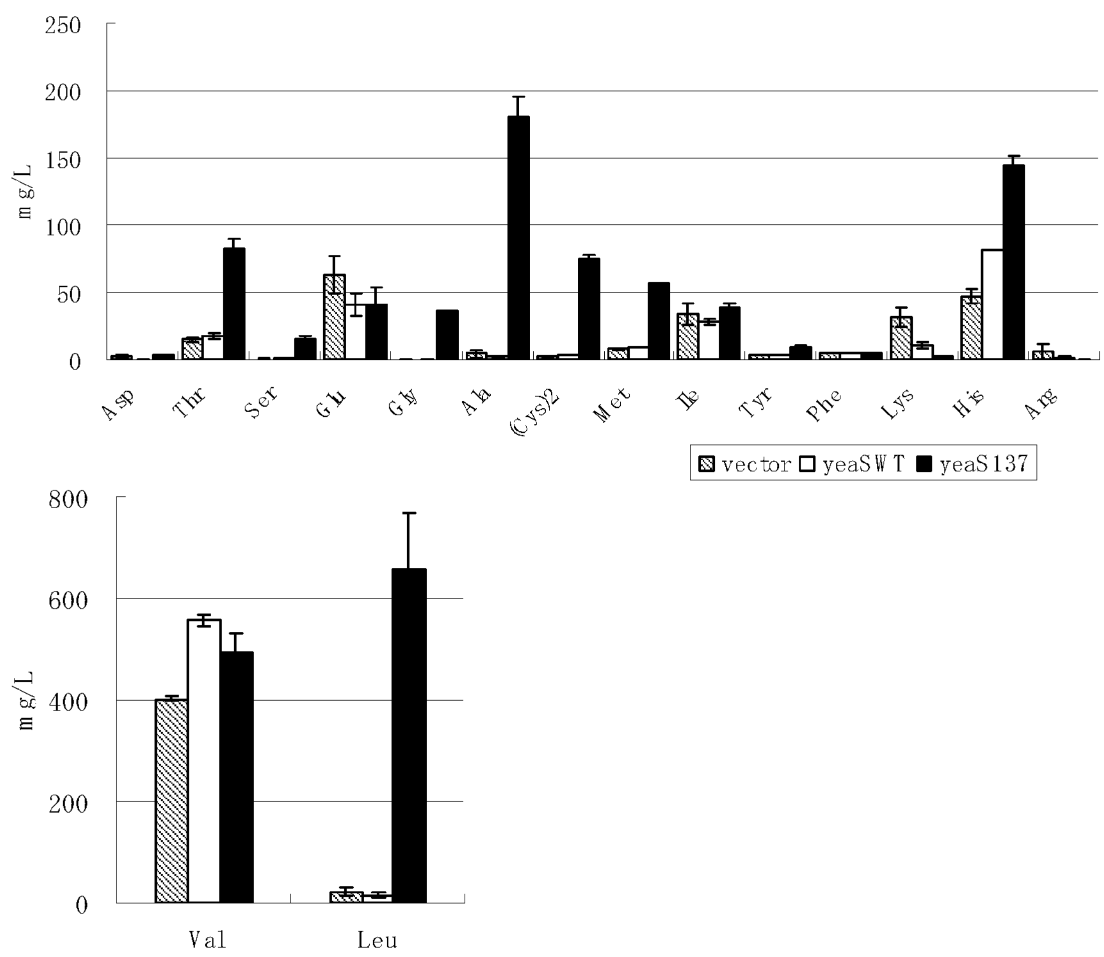
FIG. 3 shows amino acid concentrations in culture media of YeaSWT- and YeaSF137S-enhanced strains of *P. ananatis*.

The results described above revealed that YeaSF137S was useful for L-cysteine production, and it was considered that this could be due to increase of L-cysteine-secreting ability. Therefore, in order to investigate influence on secretion of other amino acids, each three samples of the media in which each of the aforementioned three strains, EYPSint-4M/pMIV-5JS, EYPSint-4M/pMIV-Pnlp8-YeaSWT, and EYPSint-4M/pMIV-Pnlp8-YeaSF137S, had been cultured, were diluted 20 times with 0.1 N hydrochloric acid, and contained various L-amino acids were quantified by using an amino acid analyzer (L-8500, Hitachi). The results are shown in FIG. 3. More various L-amino acids were secreted by a strain with YeaSF137S compared with a strain with YeaSWT, and especially secretion of L-leucine increased from 21 mg/L to 656 mg/L. From the above results, it was revealed that substitution of a serine residue for the phenylalanine residue at the 137th position of YeaS not only promoted accumulation of L-cysteine in the medium, but also promoted accumulation of other amino acids such as L-leucine, L-threonine, L-serine, glycine, L-alanine, L-cystine, L-methionine, L-histidine, and L-valine. Therefore, it is estimated that YeaSF137S also promotes secretion of these amino acids. Therefore, YeaSF137S is advantageous for fermentative production of these amino acids.

Figure 4:
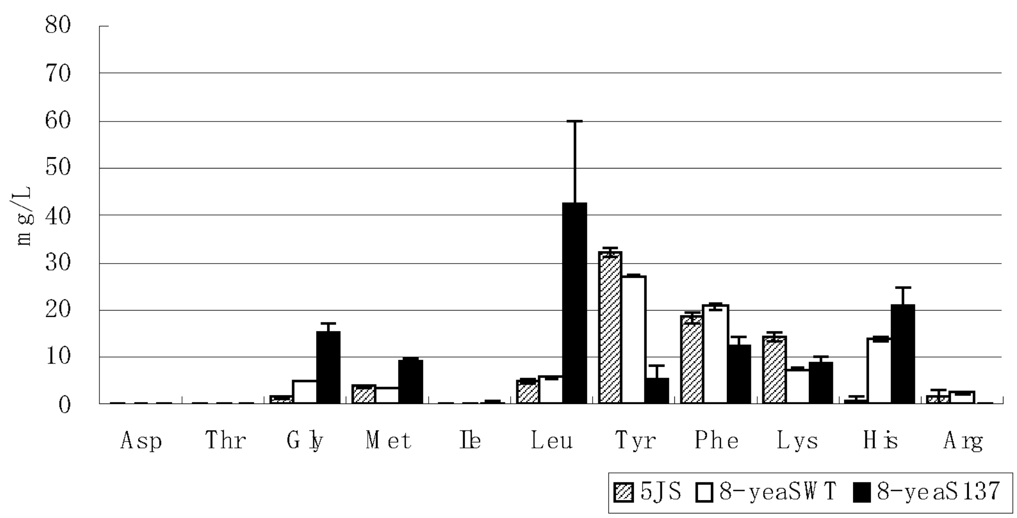
FIG. 4 shows amino acid concentrations in culture media of YeaSWT- and YeaSF137S-enhanced strains of *E. coli.*
Figure 4:
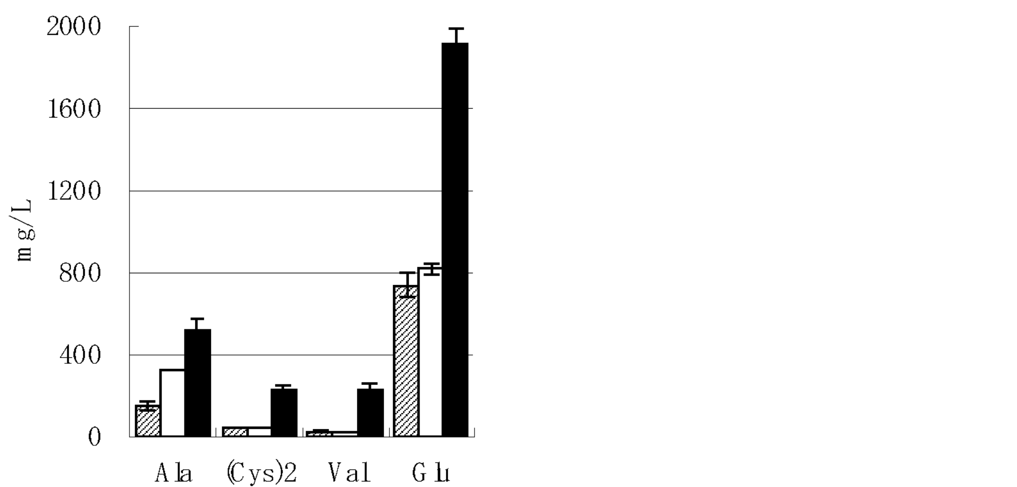

Furthermore, pMIV-5JS, pMIV-Pnlp8-YeaSWT and pMIV-Pnlp8-YeaSF137S-introduced strains were similarly prepared for *E. coli* MG1655, test tube culture was performed under the same conditions as those of the culture of EYPSint-4M(s), and amino acid analysis of the media was performed as described above. The results are shown in FIG. 4. Also in *E. coli, YeaSF*137S promoted accumulation of glycine, L-methionine, L-leucine, L-histidine, L-alanine, L-cystine, L-valine, and L-glutamic acid, and thus is advantageous for fermentative production of these amino acids.

(12) Examination of Effect of Substitution of Other Amino Acid Residues for Phenylalanine Residue at Position 137 of YesS Influence of substitution of an amino acid residue other than serine residue for the phenylalanine residue at the position 137 of YesS on L-cysteine production was examined. First, a DNA 'fragment 1' was amplified by PCR using pMIV-Pnlp8-YeaS as a template as well as P33 (aaacgtgagg aaatacctgg, SEQ ID NO: 52) and P34 (cgataaactg tacgaannnc gacacataga ac ("n" means that the corresponding residue can be any of a, t, g and c), SEQ ID NO: 53) as primers. The program consisted of 94° C. for 5 minutes, then 30 cycles of 98° C. for 5 seconds, 60° C. for 10 seconds, and 72° C. for 1 minute, and 72° C. for 1 minute as the final cycle. Furthermore, the DNA 'fragment 2' was similarly amplified by using P31 and P32 with the same cycle. Overlap PCR was performed by using a mixture of the 'fragment 1' and the 'fragment 2' diluted 10 times as a template as well as P32 and P33 as primers with the aforementioned program, and the obtained DNA fragment was purified, then treated with SalI and XbaI, and introduced into the aforementioned pMIV-Pnlp23 vector treated with the same enzymes to prepare pMIV-Pnlp23-YeaSF137*. After the sequence was confirmed, the plasmid carrying a mutant yeaS gene having a mutation for substitution of an amino acid residue other than serine residue for the phenylalanine residue at the 137th position was introduced into the *E. coli* MG1655 strain by electroporation, and the cells were inoculated on an M9 selection plate containing 1 mM L-cysteine prepared in the same manner as that described above, and cultured at 37° C. to examine the L-cysteine resistance of the strain.

L-Cysteine resistance was evaluated on the basis of that of the strain having phenylalanine (WT). As a result, degree of L-cysteine resistance increased in the strains having substitution of, besides serine (S), glutamine (Q), alanine (A), histidine (H), cysteine (C), and glycine (G). Especially high L-cysteine resistance was observed for a strain having substitution of a glutamine residue (F137Q).

Therefore, pMIV-Pnlp23-YeaSF137Q was treated with SalI and XbaI, and inserted into pMIV-Pnlp8 treated with the same enzymes to prepare pMIV-Pnlp8-YeaSF137Q ligated with yeaSF137Q under the control of pnlp8. This plasmid was introduced into an L-cysteine-producing strain of *P. ananatis*, and L-cysteine production culture was performed. As controls, EYPSint-1M(s) strains introduced with pMIV-Pnlp8-YeaSWT and pMIV-Pnlp8-YeaSF137S were used. The results are shown in Table 5. It was revealed that the activity of improving L-cysteine-producing ability of a host cell compared with a non-modified strain was more improved with the mutant YeaS in which a glutamine residue substituted for the phenylalanine residue at the 137th position (YeaSF137Q) compared with the wild-type YeaS.

TABLE 5

Effect of enhancement of YeaSWT, YeaSF137S and YeaSF137Q in cysteine-producing strain

| Plasmid introduced | Production amount of L-cysteine (g/L) |
|---|---|
| pMIV-5JS | 0.42 ± 0.12 |
| pMIV-Pnlp8-YeaS$^{F137S}$ | 1.32 ± 0.08 |
| pMIV-Pnlp8-YeaS$^{F137Q}$ | 1.09 ± 0.34 |

As described above, it was found that there was correlation between acquisition of L-cysteine resistance by increase of expression amount of a mutant yeaS and L-cysteine production. It is considered that the L-cysteine resistance is improved by promotion of extracellular secretion of L-cysteine. It can be considered that, if it is correct, mutant yeaS genes including a mutation for substitution of an alanine, histidine, cysteine, or glycine for the phenylalanine residue at the 137th position, which showed L-cysteine resistance improving effect on the M9 selection plate containing L-cysteine, are similarly effective for increasing L-cysteine production. In order to verify this expectation, confirmation can be performed by preparing pMIV-Pnlp8-YeaSF137A, pMIV-Pnlp8-YeaSF137H, pMIV-Pnlp8-YeaSF137C and pMIV-Pnlp8-YeaSF137G in the same manner as that described for the construction of pMIV-Pnlp8-YeaSF137Q mentioned above, introducing them into EYPSint-1M(s), and performing L-cysteine production culture using the obtained strains.

Explanation of Sequence Listing

SEQ ID NO: 1: Nucleotide sequence of wild-type yeaS gene

SEQ ID NO: 2: Amino acid sequence of wild-type YeaS

SEQ ID NO: 3: Nucleotide sequence of wild-type cysE gene

SEQ ID NO: 4: Amino acid sequence of serine acetyltransferase encoded by wild-type cysE SEQ ID NO: 5: Nucleotide sequence of Pnlp0

SEQ ID NO: 6: Nucleotide sequence of Pnlp8

SEQ ID NO: 7: Nucleotide sequence of Pnlp23

SEQ ID NO: 8: Nucleotide sequence of Pnlp4

SEQ ID NO: 9: Nucleotide sequence of Pnlp1

SEQ ID NO: 10: Nucleotide sequence of *Pantoea ananatis* wild-type serA gene

SEQ ID NO: 11: Amino acid sequence encoded by *Pantoea ananatis* wild-type serA gene SEQ ID NO: 12: Nucleotide sequence of cysPTWA gene cluster SEQ ID NO: 13: Amino acid sequence encoded by cysP gene SEQ ID NO: 14: Amino acid sequence encoded by cysT gene SEQ ID NO: 15: Amino acid sequence encoded by cysW gene SEQ ID NO: 16: Nucleotide sequence of cysA gene SEQ ID NO: 17: Amino acid sequence encoded by cysA gene SEQ ID NO: 18: Nucleotide sequence of cysM gene SEQ ID NO: 19: Amino acid sequence encoded by cysM gene SEQ ID NOS: 20 to 53: Primers P1 to P34

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid comprising:

a) culturing in a medium a bacterium belonging to the family Enterobacteriaceae, which is able to produce an L-amino acid, and has been modified to have a mutation in a yeaS gene selected from the group consisting of:

(I) replacing the amino acid residue at position 28 of SEQ ID NO: 2 with an amino acid residue other than threonine, (II) replacing the amino acid residue at position 137 of SEQ ID NO: 2 with an amino acid residue other than phenylalanine residue, (III) replacing the amino acid residue at position 188 of SEQ ID NO: 2 with an amino acid residue other than leucine, and, (IV) combinations thereof; and b) collecting the L-amino acid from the medium;

wherein the yeaS gene without said mutation encodes a protein selected from the group consisting of:

(A) a protein comprising the amino acid sequence of SEQ ID NO: 2, and (B) a protein comprising the amino acid sequence of SEQ ID NO: 2, but wherein 1 to 10 amino acid residues are substituted, and the protein has an activity of improving an L-cysteine-producing ability in the bacterium belonging to the family Enterobacteriaceae as compared to a non-modified bacterium when expression of the protein is increased in the bacterium.

2. The method according to claim 1, wherein the yeaS gene without said mutation is selected from the group consisting of:

(a) a DNA comprising the nucleotide sequence of SEQ ID NO: 1, and (b) a DNA which is able to hybridize with a sequence complementary to the nucleotide sequence of SEQ ID NO: 1, or a probe which can be prepared from the nucleotide sequence, under stringent conditions, and wherein said DNA encodes a protein having an activity of improving an L-cysteine-producing ability in the bacterium belonging to the family Enterobacteriaceae as compared to a non-modified strain when expression the protein is increased in the bacterium.

3. The method according to claim 1, wherein (i) said amino acid residue other than threonine is asparagine, (ii) said amino acid residue other than phenylalanine is selected from the group consisting of serine, glutamine, alanine, histidine, cysteine, and glycine, and (iii) said amino acid residue other than leucine is glutamine.

4. The method according to claim 3, wherein said amino acid other than phenylalanine is serine or glutamine.

5. The method according to claim 1, wherein the L-amino acid is selected from the group consisting of L-cysteine, L-leucine, L-threonine, L-serine, L-methionine, L-histidine, L-valine, L-glutamic acid, L-arginine, L-isoleucine, L-phenylalanine, L-tyrosine, L-tryptophan, and L-proline.

6. The method according to claim 5, wherein the L-amino acid is L-cysteine.

7. The method according to claim 6, wherein the bacterium has been further modified to increase activity of an L-cysteine biosynthesis system enzyme.

8. The method according to claim 7, wherein the L-cysteine biosynthesis system enzyme is serine acetyltransferase.

9. The method according to claim 8, wherein feedback inhibition of serine acetyltransferase by L-cysteine is reduced.

10. The method according to claim 1, wherein the bacterium is a *Pantoea* bacterium.

11. The method according to claim 10, wherein the bacterium is *Pantoea ananatis*.

12. The method according to claim 1, wherein the bacterium is *Escherichia coli.*

13. A bacterium belonging to the family Enterobacteriaceae, which is able to produce an L-amino acid, and has been modified to have a mutation in a yeaS gene selected from the group consisting of:

(I) replacing the threonine residue at position 28 of SEQ ID NO: 2 with an amino acid residue other than threonine, (II) replacing the phenylalanine residue at position 137 of SEQ ID NO: 2 with an amino acid residue other than phenylalanine, and (III) replacing the leucine residue at position 188 of SEQ ID NO: 2 with an amino acid residue other than leucine, and, (IV) combinations thereof; and wherein the yeaS gene without said mutation encodes a protein selected from the group consisting of:

(A) a protein comprising the amino acid sequence of SEQ ID NO: 2, and (B) a protein comprising the amino acid sequence of SEQ ID NO: 2, but wherein 1 to 10 amino acid residues are substituted, and the protein has an activity of improving the ability to produce L-cysteine when overexpressed in a bacterium belonging to the family Enterobacteriaceae as compared to a bacterium in which the protein is not overexpressed.

14. The bacterium according to claim 13, wherein the L-amino acid is L-cysteine.

15. A DNA which encodes a protein selected from the group consisting of:

(A) a protein comprising the amino acid sequence of SEQ ID NO: 2, and (B) a protein comprising the amino acid sequence of SEQ ID NO: 2, but wherein 1 to 10 amino acid residues are substituted, and the protein has an activity of improving the ability to produce L-cysteine when overexpressed in a bacterium belonging to the family Enterobacteriaceae as compared to a bacterium in which the protein is not overexpressed, wherein the protein has a mutation selected from the group consisting of:

(I) replacing the threonine residue at position 28 of SEQ ID NO: 2 with an amino acid residue other than threonine, (II) replacing the phenylalanine residue at position 137 of SEQ ID NO: 2 with an amino acid residue other than phenylalanine, (III) replacing the leucine residue at position 188 of SEQ ID NO: 2 with an amino acid residue other than leucine.

* * * * *

SEQUENCE LISTING

```
<160> NUMBER OF SEQ ID NOS: 53

<210> SEQ ID NO 1
<211> LENGTH: 1039
<212> TYPE: DNA
<213> ORGANISM: Escherichia coli
<220> FEATURE:
<221> NAME/KEY: CDS
<222> LOCATION: (201)..(839)

<400> SEQUENCE: 1

tgcggataac ggtagaattt ttacgccagt attttgccga gcactacccg aatttttcac      60

tggagcatgc ctgattaatg attcaattat cgggttgata tcaggttaaa acctgatttt     120

ctcctttcta agccgctaca gattggttag catattcacc tttaatcgcg catgatcgaa     180

agataattaa agaggttaat gtg ttc gct gaa tac ggg gtt ctg aat tac tgg     233
                      Val Phe Ala Glu Tyr Gly Val Leu Asn Tyr Trp
                      1               5                   10

acc tat ctg gtt ggg gcc att ttt att gtg ttg gtg cca ggg cca aat       281
Thr Tyr Leu Val Gly Ala Ile Phe Ile Val Leu Val Pro Gly Pro Asn
            15                  20                  25

acc ctg ttt gta ctc aaa aat agc gtc agt agc ggt atg aaa ggc ggt       329
Thr Leu Phe Val Leu Lys Asn Ser Val Ser Ser Gly Met Lys Gly Gly
        30                  35                  40

tat ctt gcg gcc tgc ggt gta ttt att ggc gat gcg gta ttg atg ttt       377
Tyr Leu Ala Ala Cys Gly Val Phe Ile Gly Asp Ala Val Leu Met Phe
    45                  50                  55

ctg gca tgg gct gga gtg gcg aca tta att aag acc acc ccg ata tta       425
Leu Ala Trp Ala Gly Val Ala Thr Leu Ile Lys Thr Thr Pro Ile Leu
60                  65                  70                  75

ttc aac att gta cgt tat ctt ggt gcg ttt tat ttg ctc tat ctg ggg       473
Phe Asn Ile Val Arg Tyr Leu Gly Ala Phe Tyr Leu Leu Tyr Leu Gly
                80                  85                  90

agt aaa att ctt tac gcg acc ctg aag ggt aaa aat agc gag gcc aaa       521
Ser Lys Ile Leu Tyr Ala Thr Leu Lys Gly Lys Asn Ser Glu Ala Lys
            95                  100                 105

tcc gat gag ccc caa tac ggt gct att ttt aaa cgc gcg tta att ttg       569
Ser Asp Glu Pro Gln Tyr Gly Ala Ile Phe Lys Arg Ala Leu Ile Leu
        110                 115                 120

agc ctg act aat ccg aaa gcc att ttg ttc tat gtg tcg ttt ttc gta       617
Ser Leu Thr Asn Pro Lys Ala Ile Leu Phe Tyr Val Ser Phe Phe Val
    125                 130                 135

cag ttt atc gat gtt aat gcc cca cat acg gga att tca ttc ttt att       665
Gln Phe Ile Asp Val Asn Ala Pro His Thr Gly Ile Ser Phe Phe Ile
140                 145                 150                 155

ctg gcg gcg acg ctg gaa ctg gtg agt ttc tgc tat ttg agc ttc ctg       713
Leu Ala Ala Thr Leu Glu Leu Val Ser Phe Cys Tyr Leu Ser Phe Leu
                160                 165                 170

att ata tct ggt gct ttt gtc acg cag tac ata cgt acc aaa aag aaa       761
Ile Ile Ser Gly Ala Phe Val Thr Gln Tyr Ile Arg Thr Lys Lys Lys
            175                 180                 185

ctg gct aaa gtt ggc aac tca ctg att ggt ttg atg ttc gtg ggt ttc       809
Leu Ala Lys Val Gly Asn Ser Leu Ile Gly Leu Met Phe Val Gly Phe
        190                 195                 200
```

```
gct gcc cga ctg gcg acg ctg caa tcc tga tgctttcagc ccgcgttgtc       859
Ala Ala Arg Leu Ala Thr Leu Gln Ser
    205                 210

gcgggcttcc catctataat cctccctgat tcttcgctga tatggtgcta aaaagtaacc    919

aataaatggt atttaaaatg caaattatca ggcgtaccct gaaacggctg gaataaaccg    979

ttttcagcgc attcaccgaa ggagggaaaa ggatgcttca aatcccacag aattatattc   1039


<210> SEQ ID NO 2
<211> LENGTH: 212
<212> TYPE: PRT
<213> ORGANISM: Escherichia coli

<400> SEQUENCE: 2

Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210


<210> SEQ ID NO 3
<211> LENGTH: 1422
<212> TYPE: DNA
<213> ORGANISM: Escherichia coli
<220> FEATURE:
<221> NAME/KEY: CDS
<222> LOCATION: (301)..(1119)

<400> SEQUENCE: 3

tcggtcaggg catggatgta caaagcgcgc aggagaagat tggtcaggtg gtggaaggct     60

accgcaatac gaaagaagtc cgcgaactgg cgcatcgctt cggcgttgaa atgccaataa    120

ccgaggaaat ttatcaagta ttatattgcg gaaaaaacgc gcgcgaggca gcattgactt    180

tactaggtcg tgcacgcaag gacgagcgca gcagccacta accccaggga acctttgtta    240
```

-continued

```
ccgctatgac ccggcccgcg cagaacgggc cggtcattat ctcatcgtgt ggagtaagca    300

atg tcg tgt gaa gaa ctg gaa att gtc tgg aac aat att aaa gcc gaa      348
Met Ser Cys Glu Glu Leu Glu Ile Val Trp Asn Asn Ile Lys Ala Glu
1               5                   10                  15

gcc aga acg ctg gcg gac tgt gag cca atg ctg gcc agt ttt tac cac      396
Ala Arg Thr Leu Ala Asp Cys Glu Pro Met Leu Ala Ser Phe Tyr His
            20                  25                  30

gcg acg cta ctc aag cac gaa aac ctt ggc agt gca ctg agc tac atg      444
Ala Thr Leu Leu Lys His Glu Asn Leu Gly Ser Ala Leu Ser Tyr Met
        35                  40                  45

ctg gcg aac aag ctg tca tcg cca att atg cct gct att gct atc cgt      492
Leu Ala Asn Lys Leu Ser Ser Pro Ile Met Pro Ala Ile Ala Ile Arg
    50                  55                  60

gaa gtg gtg gaa gaa gcc tac gcc gct gac ccg gaa atg atc gcc tct      540
Glu Val Val Glu Glu Ala Tyr Ala Ala Asp Pro Glu Met Ile Ala Ser
65                  70                  75                  80

gcg gcc tgt gat att cag gcg gtg cgt acc cgc gac ccg gca gtc gat      588
Ala Ala Cys Asp Ile Gln Ala Val Arg Thr Arg Asp Pro Ala Val Asp
                85                  90                  95

aaa tac tca acc ccg ttg tta tac ctg aag ggt ttt cat gcc ttg cag      636
Lys Tyr Ser Thr Pro Leu Leu Tyr Leu Lys Gly Phe His Ala Leu Gln
            100                 105                 110

gcc tat cgc atc ggt cac tgg ttg tgg aat cag ggg cgt cgc gca ctg      684
Ala Tyr Arg Ile Gly His Trp Leu Trp Asn Gln Gly Arg Arg Ala Leu
        115                 120                 125

gca atc ttt ctg caa aac cag gtt tct gtg acg ttc cag gtc gat att      732
Ala Ile Phe Leu Gln Asn Gln Val Ser Val Thr Phe Gln Val Asp Ile
    130                 135                 140

cac ccg gca gca aaa att ggt cgc ggt atc atg ctt gac cac gcg aca      780
His Pro Ala Ala Lys Ile Gly Arg Gly Ile Met Leu Asp His Ala Thr
145                 150                 155                 160

ggc atc gtc gtt ggt gaa acg gcg gtg att gaa aac gac gta tcg att      828
Gly Ile Val Val Gly Glu Thr Ala Val Ile Glu Asn Asp Val Ser Ile
                165                 170                 175

ctg caa tct gtg acg ctt ggc ggt acg ggt aaa tct ggt ggt gac cgt      876
Leu Gln Ser Val Thr Leu Gly Gly Thr Gly Lys Ser Gly Gly Asp Arg
            180                 185                 190

cac ccg aaa att cgt gaa ggt gtg atg att ggc gcg ggc gcg aaa atc      924
His Pro Lys Ile Arg Glu Gly Val Met Ile Gly Ala Gly Ala Lys Ile
        195                 200                 205

ctc ggc aat att gaa gtt ggg cgc ggc gcg aag att ggc gca ggt tcc      972
Leu Gly Asn Ile Glu Val Gly Arg Gly Ala Lys Ile Gly Ala Gly Ser
    210                 215                 220

gtg gtg ctg caa ccg gtg ccg ccg cat acc acc gcc gct ggc gtt ccg     1020
Val Val Leu Gln Pro Val Pro Pro His Thr Thr Ala Ala Gly Val Pro
225                 230                 235                 240

gct cgt att gtc ggt aaa cca gac agc gat aag cca tca atg gat atg     1068
Ala Arg Ile Val Gly Lys Pro Asp Ser Asp Lys Pro Ser Met Asp Met
                245                 250                 255

gac cag cat ttc aac ggt att aac cat aca ttt gag tat ggg gat ggg     1116
Asp Gln His Phe Asn Gly Ile Asn His Thr Phe Glu Tyr Gly Asp Gly
            260                 265                 270

atc taatgtcctg tgatcgtgcc ggatgcgatg taatcatcta tccggcctac          1169
Ile

agtaactaat ctctcaatac cgctcccgga taccccaact gccgccaggc ttcatacacc   1229

actaccgaca ccgcattgga cagattcatg ctgcggctgt ccggcaccat cggaatgcga   1289

attttttgtt cagcgggcag ggcatcaaga atgctcgctg gcaggccgcg tgtttccggg   1349
```

```
ccgaacatca gataatcgcc atcctgatag cttacggcgc tgtgagcagg tgtacctttc   1409

gtggtgaggg cga                                                      1422


<210> SEQ ID NO 4
<211> LENGTH: 273
<212> TYPE: PRT
<213> ORGANISM: Escherichia coli

<400> SEQUENCE: 4

Met Ser Cys Glu Glu Leu Glu Ile Val Trp Asn Asn Ile Lys Ala Glu
1               5                   10                  15

Ala Arg Thr Leu Ala Asp Cys Glu Pro Met Leu Ala Ser Phe Tyr His
            20                  25                  30

Ala Thr Leu Leu Lys His Glu Asn Leu Gly Ser Ala Leu Ser Tyr Met
        35                  40                  45

Leu Ala Asn Lys Leu Ser Ser Pro Ile Met Pro Ala Ile Ala Ile Arg
    50                  55                  60

Glu Val Val Glu Glu Ala Tyr Ala Ala Asp Pro Glu Met Ile Ala Ser
65                  70                  75                  80

Ala Ala Cys Asp Ile Gln Ala Val Arg Thr Arg Asp Pro Ala Val Asp
                85                  90                  95

Lys Tyr Ser Thr Pro Leu Leu Tyr Leu Lys Gly Phe His Ala Leu Gln
            100                 105                 110

Ala Tyr Arg Ile Gly His Trp Leu Trp Asn Gln Gly Arg Arg Ala Leu
        115                 120                 125

Ala Ile Phe Leu Gln Asn Gln Val Ser Val Thr Phe Gln Val Asp Ile
    130                 135                 140

His Pro Ala Ala Lys Ile Gly Arg Gly Ile Met Leu Asp His Ala Thr
145                 150                 155                 160

Gly Ile Val Val Gly Glu Thr Ala Val Ile Glu Asn Asp Val Ser Ile
                165                 170                 175

Leu Gln Ser Val Thr Leu Gly Gly Thr Gly Lys Ser Gly Gly Asp Arg
            180                 185                 190

His Pro Lys Ile Arg Glu Gly Val Met Ile Gly Ala Gly Ala Lys Ile
        195                 200                 205

Leu Gly Asn Ile Glu Val Gly Arg Gly Ala Lys Ile Gly Ala Gly Ser
    210                 215                 220

Val Val Leu Gln Pro Val Pro Pro His Thr Thr Ala Ala Gly Val Pro
225                 230                 235                 240

Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
            260                 265                 270

Ile


<210> SEQ ID NO 5
<211> LENGTH: 313
<212> TYPE: DNA
<213> ORGANISM: Escherichia coli

<400> SEQUENCE: 5

gcatgcttcc aactgcgcta atgacgcagc tggacgaagg cgggattctc gtcttacccg     60

taggggagga gcaccagtat ttgaaacggg tgcgtcgtcg gggaggcgaa tttattatcg    120

ataccgtgga ggccgtgcgc tttgtccctt tagtgaaggg tgagctggct taaaacgtga    180
```

```
ggaaatacct ggatttttcc tggttatttt gccgcaggtc agcgtatcgt gaacatcttt    240

tccagtgttc agtagggtgc cttgcacggt aattatgtca ctggttatta accaattttt    300

cctgggggtc gac                                                       313
```

<210> SEQ ID NO 6
<211> LENGTH: 312
<212> TYPE: DNA
<213> ORGANISM: Artificial Sequence
<220> FEATURE:
<223> OTHER INFORMATION: mutant nlpD promoter

<400> SEQUENCE: 6

```
gcatgcttcc aactgcgcta atgacgcagc tggacgaagg cgggattctc gtcttacccg     60

taggggagga gcaccagtat ttgaaacggg tgcgtcgtcg ggaggcgaa tttattatcg    120

ataccgtgga ggccgtgcgc tttgtccctt tagtgaaggg tgagctggct taaaacgtga    180

ggaaatacct ggatttttcc tggttatttt gccgcaggtc agcgtataat gaagatcttt    240

tccagtgttg acaagggtcc ttgcacggtt ataatgtcac tggttattaa ccaatttttc    300

ctgggggtcg ac                                                        312
```

<210> SEQ ID NO 7
<211> LENGTH: 313
<212> TYPE: DNA
<213> ORGANISM: Artificial Sequence
<220> FEATURE:
<223> OTHER INFORMATION: mutant nlpD promoter

<400> SEQUENCE: 7

```
gcatgcttcc aactgcgcta atgacgcagc tggacgaagg cgggattctc gtcttacccg     60

taggggagga gcaccagtat ttgaaacggg tgcgtcgtcg ggaggcgaa tttattatcg    120

ataccgtgga ggccgtgcgc tttgtccctt tagtgaaggg tgagctggct taaaacgtga    180

ggaaatacct ggatttttcc tggttatttt gccgcaggtc agcgtataat gaagatcttt    240

tccagtgttc agtagggtgc cttgcacggt tataatgtca ctggttatta accaattttt    300

cctgggggtc gac                                                       313
```

<210> SEQ ID NO 8
<211> LENGTH: 192
<212> TYPE: DNA
<213> ORGANISM: Artificial Sequence
<220> FEATURE:
<223> OTHER INFORMATION: mutant nlpD promoter

<400> SEQUENCE: 8

```
gcatgcacgc gtggcgatct ggcctgactg ccttgttagc atttcttcat aactgtttca     60

tggaatcagg tagttgatat tgctactatc cagttcattc aacgaaaatc cagcgtttaa    120

cgtgccgcac agtgtattgt gctggtgaga cgagtaagtc agttttttaa aggttgccac    180

cacggggtcg ac                                                        192
```

<210> SEQ ID NO 9
<211> LENGTH: 192
<212> TYPE: DNA
<213> ORGANISM: Artificial Sequence
<220> FEATURE:
<223> OTHER INFORMATION: mutant nlpD promoter

<400> SEQUENCE: 9

```
gcatgcacgc gtggcgatct ggcctgactg ccttgttagc atttcttcat aactgtttca     60
```

```
tggaatcagg tagttgatat tgctactatc cagttcattc aacgaaaatc cagcgtttaa    120

cgtgccgcac agtgtattgt gctggtgaga cgagtaagtc agttttttaa aggttgccac    180

cacggagtcg ac                                                        192


<210> SEQ ID NO 10
<211> LENGTH: 1779
<212> TYPE: DNA
<213> ORGANISM: Pantoea ananatis
<220> FEATURE:
<221> NAME/KEY: CDS
<222> LOCATION: (301)..(1536)

<400> SEQUENCE: 10

gtcaaaaccc tcaaaaaata aagcaccggg cgcacaacag ggcgcccgct ttttttgatt     60

taaaaaaact tttctcacca ggctgaaatt tggtgactta tgtcacataa ccgtcatcgg    120

cagcgggttc gttcttctcg atgcggccaa cccacgattt tgtctggcaa agtacgtcct    180

ctgagccctg ccatgctggc ggtcaggcaa tcgtttgtat tgccgcaggc gattttttttg    240

atattttgac agacggctga ctgcgttcag tcctcgttga attctgaata gggttgggaa    300

atg gca aag gta tca ctg gaa aaa gac aaa att aag ttc ctg ctg gtg      348
Met Ala Lys Val Ser Leu Glu Lys Asp Lys Ile Lys Phe Leu Leu Val
1               5                   10                  15

gaa ggt gtc cat cag agc gcg ctg gaa aat ctt cgt gct gca ggt tac      396
Glu Gly Val His Gln Ser Ala Leu Glu Asn Leu Arg Ala Ala Gly Tyr
            20                  25                  30

acc aat att gaa ttc cac aaa ggc gca ctg gat gcc gag gcg tta aaa      444
Thr Asn Ile Glu Phe His Lys Gly Ala Leu Asp Ala Glu Ala Leu Lys
        35                  40                  45

gct tcc gct cgc gat gcg cat ttt atc ggt atc cgt tcc cgt tcc caa      492
Ala Ser Ala Arg Asp Ala His Phe Ile Gly Ile Arg Ser Arg Ser Gln
    50                  55                  60

ctg acc gaa gag att ttt gcc gct gca gaa aaa ctg gta gcg gtg ggc      540
Leu Thr Glu Glu Ile Phe Ala Ala Ala Glu Lys Leu Val Ala Val Gly
65                  70                  75                  80

tgt ttc tgt atc gga acg aat cag gtt gat tta aat gcc gca gcg aaa      588
Cys Phe Cys Ile Gly Thr Asn Gln Val Asp Leu Asn Ala Ala Ala Lys
                85                  90                  95

cgc ggt atc ccg gtt ttt aac gca cct ttc tca aat acg cgc tct gtg      636
Arg Gly Ile Pro Val Phe Asn Ala Pro Phe Ser Asn Thr Arg Ser Val
            100                 105                 110

gcc gag ctg gtt att ggc gag atg ctg ctg atg ctg cgc ggt gtt ccg      684
Ala Glu Leu Val Ile Gly Glu Met Leu Leu Met Leu Arg Gly Val Pro
        115                 120                 125

gaa gcg aat gcc aaa gcg cac cgt ggt atc tgg aat aaa atc gcc aaa      732
Glu Ala Asn Ala Lys Ala His Arg Gly Ile Trp Asn Lys Ile Ala Lys
    130                 135                 140

ggc tct ttt gaa gcg cgc ggt aaa aag ctg ggt atc att ggc tat ggc      780
Gly Ser Phe Glu Ala Arg Gly Lys Lys Leu Gly Ile Ile Gly Tyr Gly
145                 150                 155                 160

cat atc ggt atg caa ctg ggc gtg ctg gca gaa agt ctg ggc atg cac      828
His Ile Gly Met Gln Leu Gly Val Leu Ala Glu Ser Leu Gly Met His
                165                 170                 175

gtt tac ttc tat gac atc gaa aac aag ctg ccg ttg ggc aac gca tca      876
Val Tyr Phe Tyr Asp Ile Glu Asn Lys Leu Pro Leu Gly Asn Ala Ser
            180                 185                 190

cag gtt cgt agc ctg acg cag ttg cta aat atg agt gac gtt gtc agc      924
Gln Val Arg Ser Leu Thr Gln Leu Leu Asn Met Ser Asp Val Val Ser
        195                 200                 205
```

```
ctg cat gtc ccg gaa acc gcc tct acg caa aat atg att tct gcc aat      972
Leu His Val Pro Glu Thr Ala Ser Thr Gln Asn Met Ile Ser Ala Asn
    210                 215                 220

gag ctg gct cag atg aag cct ggc ggc ctg ctg ata aat gcc tca cgc     1020
Glu Leu Ala Gln Met Lys Pro Gly Gly Leu Leu Ile Asn Ala Ser Arg
225                 230                 235                 240

ggc acc gtg gta gat att cct gct ttg tgc gaa gcg ctg gcc agc aag     1068
Gly Thr Val Val Asp Ile Pro Ala Leu Cys Glu Ala Leu Ala Ser Lys
                245                 250                 255

cag gtt ggt ggc gct gcg att gat gtg ttc cct gta gag ccg gcg acc     1116
Gln Val Gly Gly Ala Ala Ile Asp Val Phe Pro Val Glu Pro Ala Thr
            260                 265                 270

aac agc gat ccg ttt gtt tcc cca ctg agc gaa ttc gac aac gtt atc     1164
Asn Ser Asp Pro Phe Val Ser Pro Leu Ser Glu Phe Asp Asn Val Ile
        275                 280                 285

ctg acg ccg cac atc ggg gga tcg acg gaa gaa gct cag gag aat atc     1212
Leu Thr Pro His Ile Gly Gly Ser Thr Glu Glu Ala Gln Glu Asn Ile
    290                 295                 300

ggg att gaa gtc gcg ggc aag ctg gcg aaa tat tcg gat aac ggt tca     1260
Gly Ile Glu Val Ala Gly Lys Leu Ala Lys Tyr Ser Asp Asn Gly Ser
305                 310                 315                 320

acg ctg tcc gcc gtc aat ttc ccg gaa gtg tca ttg ccg atg cac ggc     1308
Thr Leu Ser Ala Val Asn Phe Pro Glu Val Ser Leu Pro Met His Gly
                325                 330                 335

att agc gcc agt cgt ctg ctg cat att cac gaa aac cgt ccg ggc gtt     1356
Ile Ser Ala Ser Arg Leu Leu His Ile His Glu Asn Arg Pro Gly Val
            340                 345                 350

ctc acc gcg atc aac cag att ttc gct gaa caa ggc atc aac att gcc     1404
Leu Thr Ala Ile Asn Gln Ile Phe Ala Glu Gln Gly Ile Asn Ile Ala
        355                 360                 365

gct cag tac ctg caa acc tct ccg atg atg ggt tat gtg gtc atc gac     1452
Ala Gln Tyr Leu Gln Thr Ser Pro Met Met Gly Tyr Val Val Ile Asp
    370                 375                 380

att gat gct gag cac gaa ctg gca gag aaa gct ctg caa ctg atg aag     1500
Ile Asp Ala Glu His Glu Leu Ala Glu Lys Ala Leu Gln Leu Met Lys
385                 390                 395                 400

gcg att ccg gga acg att cgc gcc cgc ctg ctt tac tgatcccacg          1546
Ala Ile Pro Gly Thr Ile Arg Ala Arg Leu Leu Tyr
                405                 410

ctgtcaccta cccgggcaca caagcatgcc cgggtttatt catcccatag ccacagtttt   1606

gatggcgtca gcacggccgg caaaggaatg tcccacgccg ctgtaggcag cgcgtcaacc   1666

cgctgacagt catgagcgat gcccaccggt aaaaacccat gctgtttcca gttctgtaag   1726

gtgcgatcgt agaagccgcc ccccattcct aaacgctgtc cggcgcgatc gaa          1779


<210> SEQ ID NO 11
<211> LENGTH: 412
<212> TYPE: PRT
<213> ORGANISM: Pantoea ananatis

<400> SEQUENCE: 11

Met Ala Lys Val Ser Leu Glu Lys Asp Lys Ile Lys Phe Leu Leu Val
1               5                   10                  15

Glu Gly Val His Gln Ser Ala Leu Glu Asn Leu Arg Ala Ala Gly Tyr
            20                  25                  30

Thr Asn Ile Glu Phe His Lys Gly Ala Leu Asp Ala Glu Ala Leu Lys
        35                  40                  45

Ala Ser Ala Arg Asp Ala His Phe Ile Gly Ile Arg Ser Arg Ser Gln
```

```
    50                  55                  60

Leu Thr Glu Glu Ile Phe Ala Ala Ala Glu Lys Leu Val Ala Val Gly
65                  70                  75                  80

Cys Phe Cys Ile Gly Thr Asn Gln Val Asp Leu Asn Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Met Leu Leu Met Leu Arg Gly Val Pro
        115                 120                 125

Glu Ala Asn Ala Lys Ala His Arg Gly Ile Trp Asn Lys Ile Ala Lys
    130                 135                 140

Gly Ser Phe Glu Ala Arg Gly Lys Lys Leu Gly Ile Ile Gly Tyr Gly
145                 150                 155                 160

His Ile Gly Met Gln Leu Gly Val Leu Ala Glu Ser Leu Gly Met His
                165                 170                 175

Val Tyr Phe Tyr Asp Ile Glu Asn Lys Leu Pro Leu Gly Asn Ala Ser
            180                 185                 190

Gln Val Arg Ser Leu Thr Gln Leu Leu Asn Met Ser Asp Val Val Ser
        195                 200                 205

Leu His Val Pro Glu Thr Ala Ser Thr Gln Asn Met Ile Ser Ala Asn
    210                 215                 220

Glu Leu Ala Gln Met Lys Pro Gly Gly Leu Leu Ile Asn Ala Ser Arg
225                 230                 235                 240

Gly Thr Val Val Asp Ile Pro Ala Leu Cys Glu Ala Leu Ala Ser Lys
                245                 250                 255

Gln Val Gly Gly Ala Ala Ile Asp Val Phe Pro Val Glu Pro Ala Thr
            260                 265                 270

Asn Ser Asp Pro Phe Val Ser Pro Leu Ser Glu Phe Asp Asn Val Ile
        275                 280                 285

Leu Thr Pro His Ile Gly Gly Ser Thr Glu Glu Ala Gln Glu Asn Ile
    290                 295                 300

Gly Ile Glu Val Ala Gly Lys Leu Ala Lys Tyr Ser Asp Asn Gly Ser
305                 310                 315                 320

Thr Leu Ser Ala Val Asn Phe Pro Glu Val Ser Leu Pro Met His Gly
                325                 330                 335

Ile Ser Ala Ser Arg Leu Leu His Ile His Glu Asn Arg Pro Gly Val
            340                 345                 350

Leu Thr Ala Ile Asn Gln Ile Phe Ala Glu Gln Gly Ile Asn Ile Ala
        355                 360                 365

Ala Gln Tyr Leu Gln Thr Ser Pro Met Met Gly Tyr Val Val Ile Asp
    370                 375                 380

Ile Asp Ala Glu His Glu Leu Ala Glu Lys Ala Leu Gln Leu Met Lys
385                 390                 395                 400

Ala Ile Pro Gly Thr Ile Arg Ala Arg Leu Leu Tyr
                405                 410


<210> SEQ ID NO 12
<211> LENGTH: 4403
<212> TYPE: DNA
<213> ORGANISM: Pantoea ananatis
<220> FEATURE:
<221> NAME/KEY: CDS
<222> LOCATION: (301)..(1311)
<220> FEATURE:
<221> NAME/KEY: CDS
<222> LOCATION: (1317)..(2147)
```

```
<220> FEATURE:
<221> NAME/KEY: CDS
<222> LOCATION: (2150)..(3022)

<400> SEQUENCE: 12

tacagcggaa cctggcacgg gccagaaggg ttgatgccgt cggatgacac actcaagagc     60

tggacgctca gcaaaattgt ctggcagcgc taagtctttt ttcacaccgc tcaaccgcag    120

ggcataaccg gccctgcgcg tccaattctg tttttcgtct gtcttttccc gccgccttat    180

gcctttttcg actttgaaat cagcaaacga tatataaaac cgttacgggt ttacgctgag    240

ttataaataa actgctgtat ctgcagatga gatctgcatc aaatttcctc agggtgaacc    300

atg acc tta cca gcg atg aaa aaa atc gtg agc gga ctc gca ctg tcg      348
Met Thr Leu Pro Ala Met Lys Lys Ile Val Ser Gly Leu Ala Leu Ser
1               5                   10                  15

ctg agt ctg gcc ggt gcc gca aac gcg acc gag ctg ttg aac agc tct      396
Leu Ser Leu Ala Gly Ala Ala Asn Ala Thr Glu Leu Leu Asn Ser Ser
            20                  25                  30

tac gat gtc gca cgt gaa tta ttt gtc gcc ctg aat gcg cct ttt gtc      444
Tyr Asp Val Ala Arg Glu Leu Phe Val Ala Leu Asn Ala Pro Phe Val
        35                  40                  45

agc cag tgg gat gcc agc cat cct gac gac aag ctg acc att aag atg      492
Ser Gln Trp Asp Ala Ser His Pro Asp Asp Lys Leu Thr Ile Lys Met
    50                  55                  60

tcc cat gcc ggg tca tcc aaa cag gcg ctg gcg atc ctg caa ggc ctg      540
Ser His Ala Gly Ser Ser Lys Gln Ala Leu Ala Ile Leu Gln Gly Leu
65                  70                  75                  80

cgt gcc gat gtg gtg acc tat aac cag gtc acc gat gtg cag gtg ctg      588
Arg Ala Asp Val Val Thr Tyr Asn Gln Val Thr Asp Val Gln Val Leu
                85                  90                  95

cac gat aaa ggc aaa ctg atc cct gcc gac tgg caa acc cgc ctg ccg      636
His Asp Lys Gly Lys Leu Ile Pro Ala Asp Trp Gln Thr Arg Leu Pro
            100                 105                 110

aat aac agt tcg ccg ttt tac tcc acc atg gcg ttc ctg gtg cgc aag      684
Asn Asn Ser Ser Pro Phe Tyr Ser Thr Met Ala Phe Leu Val Arg Lys
        115                 120                 125

gga aac cca aag cag att cac gac tgg tcc gat tta acc cgt gac gat      732
Gly Asn Pro Lys Gln Ile His Asp Trp Ser Asp Leu Thr Arg Asp Asp
    130                 135                 140

gtg aag ctg att ttt cct aat ccc aaa acc tcg ggc aac gga cgt tat      780
Val Lys Leu Ile Phe Pro Asn Pro Lys Thr Ser Gly Asn Gly Arg Tyr
145                 150                 155                 160

acc tat ctt gct gcc tgg ggc gcc gcc agc aac act gac ggg ggc gat      828
Thr Tyr Leu Ala Ala Trp Gly Ala Ala Ser Asn Thr Asp Gly Gly Asp
                165                 170                 175

cag gct aaa acc cgc gct ttt atg aca aaa ttt ctg aaa aat gtt gaa      876
Gln Ala Lys Thr Arg Ala Phe Met Thr Lys Phe Leu Lys Asn Val Glu
            180                 185                 190

gtc ttc gat acc ggt ggc cga ggt gct acg acc acc ttt gct gaa cgc      924
Val Phe Asp Thr Gly Gly Arg Gly Ala Thr Thr Thr Phe Ala Glu Arg
        195                 200                 205

ggt ctg ggc gat gtg ttg atc agt ttt gag tct gaa gtg aat aac atc      972
Gly Leu Gly Asp Val Leu Ile Ser Phe Glu Ser Glu Val Asn Asn Ile
    210                 215                 220

cgc aac cag tac ggc aaa gac gac tac gaa gtc gtg gtg cct aaa acc     1020
Arg Asn Gln Tyr Gly Lys Asp Asp Tyr Glu Val Val Val Pro Lys Thr
225                 230                 235                 240

gat att ctc gcg gag ttt ccc gtt gcc tgg gta gat aaa aac gtc gag     1068
Asp Ile Leu Ala Glu Phe Pro Val Ala Trp Val Asp Lys Asn Val Glu
                245                 250                 255
```

-continued

```
cag aat aaa aca gcc gat gca gcg aaa gcc tat ctg acc tgg ctg tat     1116
Gln Asn Lys Thr Ala Asp Ala Ala Lys Ala Tyr Leu Thr Trp Leu Tyr
            260                 265                 270

tct cct gcg gcg cag aaa att att acg gat ttc tat tac cgc gtg aac     1164
Ser Pro Ala Ala Gln Lys Ile Ile Thr Asp Phe Tyr Tyr Arg Val Asn
        275                 280                 285

aat ccg cag tta atg gcg cag caa aaa gcc cgt ttt cct gcc acg aac     1212
Asn Pro Gln Leu Met Ala Gln Gln Lys Ala Arg Phe Pro Ala Thr Asn
    290                 295                 300

ctg ttt cgt gtt gaa gac att ttt ggc ggc tgg gat aac gtg atg aaa     1260
Leu Phe Arg Val Glu Asp Ile Phe Gly Gly Trp Asp Asn Val Met Lys
305                 310                 315                 320

acc cat ttc gcc agc ggt ggc gag cta gac cag tta tta gcg gcg ggg     1308
Thr His Phe Ala Ser Gly Gly Glu Leu Asp Gln Leu Leu Ala Ala Gly
                325                 330                 335

cgg tgatc atg ttt gca gcc agc caa aaa cgc gtc ctg ccc ggt ttc ggt   1358
Arg       Met Phe Ala Ala Ser Gln Lys Arg Val Leu Pro Gly Phe Gly
                    340                 345                 350

ctc agc ctg ggc acc agc ctg ctc ttt acc tgt ctg gtg ctg ctg ctg     1406
Leu Ser Leu Gly Thr Ser Leu Leu Phe Thr Cys Leu Val Leu Leu Leu
            355                 360                 365

cca atc agc gca ctg att atg cag ctg tcg cag atg acg ttg cag caa     1454
Pro Ile Ser Ala Leu Ile Met Gln Leu Ser Gln Met Thr Leu Gln Gln
        370                 375                 380

tac tgg gac gtg gtc acc aat ccg cag ctc atc gcg gcc tat aag gtc     1502
Tyr Trp Asp Val Val Thr Asn Pro Gln Leu Ile Ala Ala Tyr Lys Val
    385                 390                 395

acg ctg ctg tcg gcc ggt gtg gcc tca ctg ttt aat gcc gta ttc ggc     1550
Thr Leu Leu Ser Ala Gly Val Ala Ser Leu Phe Asn Ala Val Phe Gly
400                 405                 410                 415

atg tta atg gcg tgg atc tta acg cgt tac cgt ttt ccg ggc cgc acg     1598
Met Leu Met Ala Trp Ile Leu Thr Arg Tyr Arg Phe Pro Gly Arg Thr
                420                 425                 430

ctg ctc gat ggt ctg atg gat ctg ccg ttt gcg ctg ccg acc gcg gtt     1646
Leu Leu Asp Gly Leu Met Asp Leu Pro Phe Ala Leu Pro Thr Ala Val
            435                 440                 445

gct ggc ctg acg ctg gcc ggt ctg ttt tcc gtg aac ggc tgg tac gga     1694
Ala Gly Leu Thr Leu Ala Gly Leu Phe Ser Val Asn Gly Trp Tyr Gly
        450                 455                 460

caa tgg ttc gcg cat ttt gat atc aag atc tcc tat acc tgg atc ggt     1742
Gln Trp Phe Ala His Phe Asp Ile Lys Ile Ser Tyr Thr Trp Ile Gly
    465                 470                 475

atc gcg ctc gcg atg gcc ttc acc agt att ccg ttt gtg gtg cgt acc     1790
Ile Ala Leu Ala Met Ala Phe Thr Ser Ile Pro Phe Val Val Arg Thr
480                 485                 490                 495

gtg cag ccg gtg ctg gaa gag ctg ggg cct gaa tat gag gaa gcg gct     1838
Val Gln Pro Val Leu Glu Glu Leu Gly Pro Glu Tyr Glu Glu Ala Ala
                500                 505                 510

caa acg ctg ggc gcc acg ccc tgg cag agc ttc cgc cgg gtc gtt ctg     1886
Gln Thr Leu Gly Ala Thr Pro Trp Gln Ser Phe Arg Arg Val Val Leu
            515                 520                 525

cct gaa gtg gca ccg gcc tta ctt gcg ggc acc gcg ctg tcg ttt acc     1934
Pro Glu Val Ala Pro Ala Leu Leu Ala Gly Thr Ala Leu Ser Phe Thr
        530                 535                 540

cgc agc ctg ggc gag ttt ggt gcg gta atc ttt att gcc ggc aac atc     1982
Arg Ser Leu Gly Glu Phe Gly Ala Val Ile Phe Ile Ala Gly Asn Ile
    545                 550                 555

gct tgg aaa acc gaa gtg acc tcg ctg atg atc ttc gtg cgc ctg cag     2030
Ala Trp Lys Thr Glu Val Thr Ser Leu Met Ile Phe Val Arg Leu Gln
```

```
560                 565                 570                 575

gag ttt gac tat ccg gca gcc agc gcc att gcc tcg gtc att ctg gcg      2078
Glu Phe Asp Tyr Pro Ala Ala Ser Ala Ile Ala Ser Val Ile Leu Ala
                580                 585                 590

gca tca ctg ctg tta ctt ttc gct atc aat acc tta caa agc cgc ttt      2126
Ala Ser Leu Leu Leu Leu Phe Ala Ile Asn Thr Leu Gln Ser Arg Phe
            595                 600                 605

ggt cgt cgt ctg gga ggc cat ta atg gca gag att tcg caa ctc aat       2173
Gly Arg Arg Leu Gly Gly His    Met Ala Glu Ile Ser Gln Leu Asn
        610                    615                 620

cat gcc gac cgc cag cct gtt aac tgg gcc aag tgg ctg ctt att ggt      2221
His Ala Asp Arg Gln Pro Val Asn Trp Ala Lys Trp Leu Leu Ile Gly
        625                 630                 635

att ggt gcg ctg ata tcc ttg ctg ctg ctg gtc gtg ccg atg gtg tcc      2269
Ile Gly Ala Leu Ile Ser Leu Leu Leu Leu Val Val Pro Met Val Ser
    640                 645                 650

atc ttc tgg gag gcc ctg cat aaa gga ctg ggc gtc acc tta agt aat      2317
Ile Phe Trp Glu Ala Leu His Lys Gly Leu Gly Val Thr Leu Ser Asn
655                 660                 665                 670

ctg acc gac agc gac atg ctc cat gcc ata tgg ctc acg gtg ctg gtc      2365
Leu Thr Asp Ser Asp Met Leu His Ala Ile Trp Leu Thr Val Leu Val
                675                 680                 685

gca ttg att acc gtg ccg gtg aat tta gtg ttc ggc acg ctg ctg gcc      2413
Ala Leu Ile Thr Val Pro Val Asn Leu Val Phe Gly Thr Leu Leu Ala
            690                 695                 700

tgg ctg gtg aca cgc ttt acc ttt ccg gga cgt cag ctg ctt ttg acg      2461
Trp Leu Val Thr Arg Phe Thr Phe Pro Gly Arg Gln Leu Leu Leu Thr
        705                 710                 715

ctg ttc gat att ccc ttt gcg gta tcg cct gtg gtc gcc ggt ctg atg      2509
Leu Phe Asp Ile Pro Phe Ala Val Ser Pro Val Val Ala Gly Leu Met
    720                 725                 730

tat ctc ctg ttc tgg ggc att aac ggc ccg gcg ggc ggc tgg ctg gat      2557
Tyr Leu Leu Phe Trp Gly Ile Asn Gly Pro Ala Gly Gly Trp Leu Asp
735                 740                 745                 750

gcc cat aat att cag gtg atg ttc tcc tgg cct ggc atg gtg ctg gtc      2605
Ala His Asn Ile Gln Val Met Phe Ser Trp Pro Gly Met Val Leu Val
                755                 760                 765

acc gtc ttc gtt acc tgt ccg ttt gtg gtg cgc gaa ctg gtg ccg gtg      2653
Thr Val Phe Val Thr Cys Pro Phe Val Val Arg Glu Leu Val Pro Val
            770                 775                 780

atg ctg agc cag ggc agt cat gaa gat gaa gcc gcg gtg ctg tta ggt      2701
Met Leu Ser Gln Gly Ser His Glu Asp Glu Ala Ala Val Leu Leu Gly
        785                 790                 795

gcc tcg ggc tgg cag atg ttc cgt cgc gtg acg ctg ccg aat att cgc      2749
Ala Ser Gly Trp Gln Met Phe Arg Arg Val Thr Leu Pro Asn Ile Arg
    800                 805                 810

tgg gcc atg ctg tat ggc gtc gtg ctg acc aac gcc cgc gcg att ggt      2797
Trp Ala Met Leu Tyr Gly Val Val Leu Thr Asn Ala Arg Ala Ile Gly
815                 820                 825                 830

gag ttt ggc gcg gtt tcc gtg gtt tcg ggt tct att cgc ggt gaa acc      2845
Glu Phe Gly Ala Val Ser Val Val Ser Gly Ser Ile Arg Gly Glu Thr
                835                 840                 845

tac act tta ccg ctt cag gtt gaa tta ctg cat cag gat tac aac acg      2893
Tyr Thr Leu Pro Leu Gln Val Glu Leu Leu His Gln Asp Tyr Asn Thr
            850                 855                 860

gtg ggc gcc ttt act gcc gca gcc tta ctg acc gtg atg gca atc gtg      2941
Val Gly Ala Phe Thr Ala Ala Ala Leu Leu Thr Val Met Ala Ile Val
        865                 870                 875

acg ctg ttt ctg aaa agc att gtg caa tgg cgt tta gag caa cag cac      2989
```

```
Thr Leu Phe Leu Lys Ser Ile Val Gln Trp Arg Leu Glu Gln Gln His
    880                 885                 890

aaa cgc ctg caa ctg gag gac aat cat gag cat tgagattaac cagatcaaca   3042
Lys Arg Leu Gln Leu Glu Asp Asn His Glu His
895                 900                 905

aatcctttgg tcgcacagcg gtgctgaacg atatctcact ggatattcct tctggccaga   3102

tggtggcctt actggggccg tccggttccg gtaaaaccac gctgctgcgc atcattgctg   3162

gactggaaca tcagaacagc ggtcagattc gttttcacga ccacgatgtc agccgcctgc   3222

acgcccgcga tcgccaggtc ggatttgtct tccagcacta tgcgctgttc cgtcatatga   3282

cggtcttcga caatattgcc tttggcctga ccgtgctgcc gcgccgtgag cgtccgtcca   3342

gtgcggaaat taaaaaacgc gtcacgcgcc tgctggagat ggtgcagctt tcccatctgg   3402

cgaaccgttt cccggcccag ctttcgggag ggcagaagca gcgcgtcgcg ctggcaagag   3462

ccctggccgt ggaaccgcaa atcctgttgc tggatgagcc ctttggtgcg ctggacgctc   3522

aggtgcgtaa agagctgcgc cgttggttac gtcagctgca cgaagaattg aagttcacca   3582

gcgtgttcgt cacccacgat caggaagagg cgatggaagt ggccgatcgc gtggtggtga   3642

tgagccaggg cagcatcgaa caggtgggga cgccggatga agtctggcgc gatcccgcca   3702

cgcgcttcgt gctggaattc ctgggtgagg ttaaccgctt cgacggtgaa gtgcatggtt   3762

ctcagttcca tgtcggggcg caccactggc cgttaggcta tacctctgca catcagggcg   3822

cggtcgatct gttcctgcgc ccgtgggaaa tcgacgtttc gcgcagaagt agcctggaaa   3882

cgccgctgcc cgttcaggtc ttagaagtga gtcctcgtgg tcacttctgg cagctggtgg   3942

tgcagccaac gggatggcag agcgagccct tctcgctggt ctttgacggt gaacagaccg   4002

cgccgttgcg cggcgagcgc ctgttcgtgg ggctgcagca ggccagactg taccagggcg   4062

cgacaccgtt acgggcggtt gcctttgcac acagcgcctg ataggttgag tgaatgttaa   4122

acgcccggag gcgcttcccg cgatccgggc tttttaatgg caaggtttgt aacctgtaga   4182

cctgataaga cgcgcaagcg tcgcatcagg caacaccacg tatggataga gatcgtgagt   4242

acattagaac aaacaatagg caatacgcct ctggtgaagt tgcagcgaat ggggccggat   4302

aacggcagtg aagtgtggtt aaaactggaa ggcaataacc cggcaggttc ggtgaaagat   4362

cgtgcggcac tttcgatgat cgtcgaggcg gaaaagcgcg g                       4403


<210> SEQ ID NO 13
<211> LENGTH: 337
<212> TYPE: PRT
<213> ORGANISM: Pantoea ananatis

<400> SEQUENCE: 13

Met Thr Leu Pro Ala Met Lys Lys Ile Val Ser Gly Leu Ala Leu Ser
1               5                   10                  15

Leu Ser Leu Ala Gly Ala Ala Asn Ala Thr Glu Leu Leu Asn Ser Ser
            20                  25                  30

Tyr Asp Val Ala Arg Glu Leu Phe Val Ala Leu Asn Ala Pro Phe Val
        35                  40                  45

Ser Gln Trp Asp Ala Ser His Pro Asp Asp Lys Leu Thr Ile Lys Met
    50                  55                  60

Ser His Ala Gly Ser Ser Lys Gln Ala Leu Ala Ile Leu Gln Gly Leu
65                  70                  75                  80

Arg Ala Asp Val Val Thr Tyr Asn Gln Val Thr Asp Val Gln Val Leu
                85                  90                  95
```

```
His Asp Lys Gly Lys Leu Ile Pro Ala Asp Trp Gln Thr Arg Leu Pro
            100                 105                 110

Asn Asn Ser Ser Pro Phe Tyr Ser Thr Met Ala Phe Leu Val Arg Lys
        115                 120                 125

Gly Asn Pro Lys Gln Ile His Asp Trp Ser Asp Leu Thr Arg Asp Asp
    130                 135                 140

Val Lys Leu Ile Phe Pro Asn Pro Lys Thr Ser Gly Asn Gly Arg Tyr
145                 150                 155                 160

Thr Tyr Leu Ala Ala Trp Gly Ala Ala Ser Asn Thr Asp Gly Gly Asp
                165                 170                 175

Gln Ala Lys Thr Arg Ala Phe Met Thr Lys Phe Leu Lys Asn Val Glu
            180                 185                 190

Val Phe Asp Thr Gly Gly Arg Gly Ala Thr Thr Thr Phe Ala Glu Arg
        195                 200                 205

Gly Leu Gly Asp Val Leu Ile Ser Phe Glu Ser Glu Val Asn Asn Ile
    210                 215                 220

Arg Asn Gln Tyr Gly Lys Asp Asp Tyr Glu Val Val Val Pro Lys Thr
225                 230                 235                 240

Asp Ile Leu Ala Glu Phe Pro Val Ala Trp Val Asp Lys Asn Val Glu
                245                 250                 255

Gln Asn Lys Thr Ala Asp Ala Ala Lys Ala Tyr Leu Thr Trp Leu Tyr
            260                 265                 270

Ser Pro Ala Ala Gln Lys Ile Ile Thr Asp Phe Tyr Tyr Arg Val Asn
        275                 280                 285

Asn Pro Gln Leu Met Ala Gln Gln Lys Ala Arg Phe Pro Ala Thr Asn
    290                 295                 300

Leu Phe Arg Val Glu Asp Ile Phe Gly Gly Trp Asp Asn Val Met Lys
305                 310                 315                 320

Thr His Phe Ala Ser Gly Gly Glu Leu Asp Gln Leu Leu Ala Ala Gly
                325                 330                 335

Arg


<210> SEQ ID NO 14
<211> LENGTH: 277
<212> TYPE: PRT
<213> ORGANISM: Pantoea ananatis

<400> SEQUENCE: 14

Met Phe Ala Ala Ser Gln Lys Arg Val Leu Pro Gly Phe Gly Leu Ser
1               5                   10                  15

Leu Gly Thr Ser Leu Leu Phe Thr Cys Leu Val Leu Leu Leu Pro Ile
            20                  25                  30

Ser Ala Leu Ile Met Gln Leu Ser Gln Met Thr Leu Gln Gln Tyr Trp
        35                  40                  45

Asp Val Val Thr Asn Pro Gln Leu Ile Ala Ala Tyr Lys Val Thr Leu
    50                  55                  60

Leu Ser Ala Gly Val Ala Ser Leu Phe Asn Ala Val Phe Gly Met Leu
65                  70                  75                  80

Met Ala Trp Ile Leu Thr Arg Tyr Arg Phe Pro Gly Arg Thr Leu Leu
                85                  90                  95

Asp Gly Leu Met Asp Leu Pro Phe Ala Leu Pro Thr Ala Val Ala Gly
            100                 105                 110

Leu Thr Leu Ala Gly Leu Phe Ser Val Asn Gly Trp Tyr Gly Gln Trp
        115                 120                 125
```

```
Phe Ala His Phe Asp Ile Lys Ile Ser Tyr Thr Trp Ile Gly Ile Ala
    130                 135                 140

Leu Ala Met Ala Phe Thr Ser Ile Pro Phe Val Val Arg Thr Val Gln
145                 150                 155                 160

Pro Val Leu Glu Glu Leu Gly Pro Glu Tyr Glu Glu Ala Ala Gln Thr
                165                 170                 175

Leu Gly Ala Thr Pro Trp Gln Ser Phe Arg Arg Val Val Leu Pro Glu
            180                 185                 190

Val Ala Pro Ala Leu Leu Ala Gly Thr Ala Leu Ser Phe Thr Arg Ser
        195                 200                 205

Leu Gly Glu Phe Gly Ala Val Ile Phe Ile Ala Gly Asn Ile Ala Trp
    210                 215                 220

Lys Thr Glu Val Thr Ser Leu Met Ile Phe Val Arg Leu Gln Glu Phe
225                 230                 235                 240

Asp Tyr Pro Ala Ala Ser Ala Ile Ala Ser Val Ile Leu Ala Ala Ser
                245                 250                 255

Leu Leu Leu Leu Phe Ala Ile Asn Thr Leu Gln Ser Arg Phe Gly Arg
            260                 265                 270

Arg Leu Gly Gly His
        275


<210> SEQ ID NO 15
<211> LENGTH: 291
<212> TYPE: PRT
<213> ORGANISM: Pantoea ananatis

<400> SEQUENCE: 15

Met Ala Glu Ile Ser Gln Leu Asn His Ala Asp Arg Gln Pro Val Asn
1               5                   10                  15

Trp Ala Lys Trp Leu Leu Ile Gly Ile Gly Ala Leu Ile Ser Leu Leu
            20                  25                  30

Leu Leu Val Val Pro Met Val Ser Ile Phe Trp Glu Ala Leu His Lys
        35                  40                  45

Gly Leu Gly Val Thr Leu Ser Asn Leu Thr Asp Ser Asp Met Leu His
    50                  55                  60

Ala Ile Trp Leu Thr Val Leu Val Ala Leu Ile Thr Val Pro Val Asn
65                  70                  75                  80

Leu Val Phe Gly Thr Leu Leu Ala Trp Leu Val Thr Arg Phe Thr Phe
                85                  90                  95

Pro Gly Arg Gln Leu Leu Leu Thr Leu Phe Asp Ile Pro Phe Ala Val
            100                 105                 110

Ser Pro Val Val Ala Gly Leu Met Tyr Leu Leu Phe Trp Gly Ile Asn
        115                 120                 125

Gly Pro Ala Gly Gly Trp Leu Asp Ala His Asn Ile Gln Val Met Phe
    130                 135                 140

Ser Trp Pro Gly Met Val Leu Val Thr Val Phe Val Thr Cys Pro Phe
145                 150                 155                 160

Val Val Arg Glu Leu Val Pro Val Met Leu Ser Gln Gly Ser His Glu
                165                 170                 175

Asp Glu Ala Ala Val Leu Leu Gly Ala Ser Gly Trp Gln Met Phe Arg
            180                 185                 190

Arg Val Thr Leu Pro Asn Ile Arg Trp Ala Met Leu Tyr Gly Val Val
        195                 200                 205

Leu Thr Asn Ala Arg Ala Ile Gly Glu Phe Gly Ala Val Ser Val Val
    210                 215                 220
```

```
Ser Gly Ser Ile Arg Gly Glu Thr Tyr Thr Leu Pro Leu Gln Val Glu
225                 230                 235                 240

Leu Leu His Gln Asp Tyr Asn Thr Val Gly Ala Phe Thr Ala Ala Ala
                245                 250                 255

Leu Leu Thr Val Met Ala Ile Val Thr Leu Phe Leu Lys Ser Ile Val
            260                 265                 270

Gln Trp Arg Leu Glu Gln Gln His Lys Arg Leu Gln Leu Glu Asp Asn
        275                 280                 285

His Glu His
    290


<210> SEQ ID NO 16
<211> LENGTH: 1403
<212> TYPE: DNA
<213> ORGANISM: Pantoea ananatis
<220> FEATURE:
<221> NAME/KEY: CDS
<222> LOCATION: (15)..(1103)

<400> SEQUENCE: 16

actggaggac aatc atg agc att gag att aac cag atc aac aaa tcc ttt       50
                Met Ser Ile Glu Ile Asn Gln Ile Asn Lys Ser Phe
                1               5                   10

ggt cgc aca gcg gtg ctg aac gat atc tca ctg gat att cct tct ggc       98
Gly Arg Thr Ala Val Leu Asn Asp Ile Ser Leu Asp Ile Pro Ser Gly
        15                  20                  25

cag atg gtg gcc tta ctg ggg ccg tcc ggt tcc ggt aaa acc acg ctg      146
Gln Met Val Ala Leu Leu Gly Pro Ser Gly Ser Gly Lys Thr Thr Leu
    30                  35                  40

ctg cgc atc att gct gga ctg gaa cat cag aac agc ggt cag att cgt      194
Leu Arg Ile Ile Ala Gly Leu Glu His Gln Asn Ser Gly Gln Ile Arg
45                  50                  55                  60

ttt cac gac cac gat gtc agc cgc ctg cac gcc cgc gat cgc cag gtc      242
Phe His Asp His Asp Val Ser Arg Leu His Ala Arg Asp Arg Gln Val
                65                  70                  75

gga ttt gtc ttc cag cac tat gcg ctg ttc cgt cat atg acg gtc ttc      290
Gly Phe Val Phe Gln His Tyr Ala Leu Phe Arg His Met Thr Val Phe
            80                  85                  90

gac aat att gcc ttt ggc ctg acc gtg ctg ccg cgc cgt gag cgt ccg      338
Asp Asn Ile Ala Phe Gly Leu Thr Val Leu Pro Arg Arg Glu Arg Pro
        95                  100                 105

tcc agt gcg gaa att aaa aaa cgc gtc acg cgc ctg ctg gag atg gtg      386
Ser Ser Ala Glu Ile Lys Lys Arg Val Thr Arg Leu Leu Glu Met Val
    110                 115                 120

cag ctt tcc cat ctg gcg aac cgt ttc ccg gcc cag ctt tcg gga ggg      434
Gln Leu Ser His Leu Ala Asn Arg Phe Pro Ala Gln Leu Ser Gly Gly
125                 130                 135                 140

cag aag cag cgc gtc gcg ctg gca aga gcc ctg gcc gtg gaa ccg caa      482
Gln Lys Gln Arg Val Ala Leu Ala Arg Ala Leu Ala Val Glu Pro Gln
                145                 150                 155

atc ctg ttg ctg gat gag ccc ttt ggt gcg ctg gac gct cag gtg cgt      530
Ile Leu Leu Leu Asp Glu Pro Phe Gly Ala Leu Asp Ala Gln Val Arg
            160                 165                 170

aaa gag ctg cgc cgt tgg tta cgt cag ctg cac gaa gaa ttg aag ttc      578
Lys Glu Leu Arg Arg Trp Leu Arg Gln Leu His Glu Glu Leu Lys Phe
        175                 180                 185

acc agc gtg ttc gtc acc cac gat cag gaa gag gcg atg gaa gtg gcc      626
Thr Ser Val Phe Val Thr His Asp Gln Glu Glu Ala Met Glu Val Ala
    190                 195                 200
```

```
gat cgc gtg gtg gtg atg agc cag ggc agc atc gaa cag gtg ggg acg      674
Asp Arg Val Val Val Met Ser Gln Gly Ser Ile Glu Gln Val Gly Thr
205                 210                 215                 220

ccg gat gaa gtc tgg cgc gat ccc gcc acg cgc ttc gtg ctg gaa ttc      722
Pro Asp Glu Val Trp Arg Asp Pro Ala Thr Arg Phe Val Leu Glu Phe
                225                 230                 235

ctg ggt gag gtt aac cgc ttc gac ggt gaa gtg cat ggt tct cag ttc      770
Leu Gly Glu Val Asn Arg Phe Asp Gly Glu Val His Gly Ser Gln Phe
            240                 245                 250

cat gtc ggg gcg cac cac tgg ccg tta ggc tat acc tct gca cat cag      818
His Val Gly Ala His His Trp Pro Leu Gly Tyr Thr Ser Ala His Gln
        255                 260                 265

ggc gcg gtc gat ctg ttc ctg cgc ccg tgg gaa atc gac gtt tcg cgc      866
Gly Ala Val Asp Leu Phe Leu Arg Pro Trp Glu Ile Asp Val Ser Arg
    270                 275                 280

aga agt agc ctg gaa acg ccg ctg ccc gtt cag gtc tta gaa gtg agt      914
Arg Ser Ser Leu Glu Thr Pro Leu Pro Val Gln Val Leu Glu Val Ser
285                 290                 295                 300

cct cgt ggt cac ttc tgg cag ctg gtg gtg cag cca acg gga tgg cag      962
Pro Arg Gly His Phe Trp Gln Leu Val Val Gln Pro Thr Gly Trp Gln
                305                 310                 315

agc gag ccc ttc tcg ctg gtc ttt gac ggt gaa cag acc gcg ccg ttg     1010
Ser Glu Pro Phe Ser Leu Val Phe Asp Gly Glu Gln Thr Ala Pro Leu
            320                 325                 330

cgc ggc gag cgc ctg ttc gtg ggg ctg cag cag gcc aga ctg tac cag     1058
Arg Gly Glu Arg Leu Phe Val Gly Leu Gln Gln Ala Arg Leu Tyr Gln
        335                 340                 345

ggc gcg aca ccg tta cgg gcg gtt gcc ttt gca cac agc gcc tga         1103
Gly Ala Thr Pro Leu Arg Ala Val Ala Phe Ala His Ser Ala
    350                 355                 360

taggttgagt gaatgttaaa cgcccggagg cgcttcccgc gatccgggct ttttaatggc   1163

aaggtttgta acctgtagac ctgataagac gcgcaagcgt cgcatcaggc aacaccacgt   1223

atggatagag atcgtgagta cattagaaca aacaataggc aatacgcctc tggtgaagtt   1283

gcagcgaatg gggccggata acggcagtga agtgtggtta aaactggaag gcaataaccc   1343

ggcaggttcg gtgaaagatc gtgcggcact ttcgatgatc gtcgaggcgg aaaagcgcgg   1403


<210> SEQ ID NO 17
<211> LENGTH: 362
<212> TYPE: PRT
<213> ORGANISM: Pantoea ananatis

<400> SEQUENCE: 17

Met Ser Ile Glu Ile Asn Gln Ile Asn Lys Ser Phe Gly Arg Thr Ala
1               5                   10                  15

Val Leu Asn Asp Ile Ser Leu Asp Ile Pro Ser Gly Gln Met Val Ala
            20                  25                  30

Leu Leu Gly Pro Ser Gly Ser Gly Lys Thr Thr Leu Leu Arg Ile Ile
        35                  40                  45

Ala Gly Leu Glu His Gln Asn Ser Gly Gln Ile Arg Phe His Asp His
    50                  55                  60

Asp Val Ser Arg Leu His Ala Arg Asp Arg Gln Val Gly Phe Val Phe
65                  70                  75                  80

Gln His Tyr Ala Leu Phe Arg His Met Thr Val Phe Asp Asn Ile Ala
                85                  90                  95

Phe Gly Leu Thr Val Leu Pro Arg Arg Glu Arg Pro Ser Ser Ala Glu
            100                 105                 110
```

```
Ile Lys Lys Arg Val Thr Arg Leu Leu Glu Met Val Gln Leu Ser His
        115                 120                 125

Leu Ala Asn Arg Phe Pro Ala Gln Leu Ser Gly Gly Gln Lys Gln Arg
    130                 135                 140

Val Ala Leu Ala Arg Ala Leu Ala Val Glu Pro Gln Ile Leu Leu Leu
145                 150                 155                 160

Asp Glu Pro Phe Gly Ala Leu Asp Ala Gln Val Arg Lys Glu Leu Arg
                165                 170                 175

Arg Trp Leu Arg Gln Leu His Glu Glu Leu Lys Phe Thr Ser Val Phe
            180                 185                 190

Val Thr His Asp Gln Glu Glu Ala Met Glu Val Ala Asp Arg Val Val
        195                 200                 205

Val Met Ser Gln Gly Ser Ile Glu Gln Val Gly Thr Pro Asp Glu Val
    210                 215                 220

Trp Arg Asp Pro Ala Thr Arg Phe Val Leu Glu Phe Leu Gly Glu Val
225                 230                 235                 240

Asn Arg Phe Asp Gly Glu Val His Gly Ser Gln Phe His Val Gly Ala
                245                 250                 255

His His Trp Pro Leu Gly Tyr Thr Ser Ala His Gln Gly Ala Val Asp
            260                 265                 270

Leu Phe Leu Arg Pro Trp Glu Ile Asp Val Ser Arg Arg Ser Ser Leu
        275                 280                 285

Glu Thr Pro Leu Pro Val Gln Val Leu Glu Val Ser Pro Arg Gly His
    290                 295                 300

Phe Trp Gln Leu Val Val Gln Pro Thr Gly Trp Gln Ser Glu Pro Phe
305                 310                 315                 320

Ser Leu Val Phe Asp Gly Glu Gln Thr Ala Pro Leu Arg Gly Glu Arg
                325                 330                 335

Leu Phe Val Gly Leu Gln Gln Ala Arg Leu Tyr Gln Gly Ala Thr Pro
            340                 345                 350

Leu Arg Ala Val Ala Phe Ala His Ser Ala
        355                 360


<210> SEQ ID NO 18
<211> LENGTH: 1512
<212> TYPE: DNA
<213> ORGANISM: Artificial Sequence
<220> FEATURE:
<223> OTHER INFORMATION: primer
<220> FEATURE:
<221> NAME/KEY: CDS
<222> LOCATION: (301)..(1212)

<400> SEQUENCE: 18

agccgctggg gtggtacaac gaaccgctga cggtcgtgat gcatggcgac gatgccccgc      60

agcgtggcga gcgtttattc gttggtctgc aacatgcgcg gctgtataac ggcgacgagc     120

gtatcgaaac ccgcgatgag gaacttgctc tcgcacaaag cgcctgatag gttgagtgaa     180

tgttaaacgc ccggaggcgc ttcccgcgat ccgggctttt taatggcaag gtttgtaacc     240

tgtagacctg ataagacgcg caagcgtcgc atcaggcaac accacgtatg gatagagatc     300

gtg agt aca tta gaa caa aca ata ggc aat acg cct ctg gtg aag ttg       348
Val Ser Thr Leu Glu Gln Thr Ile Gly Asn Thr Pro Leu Val Lys Leu
1               5                   10                  15

cag cga atg ggg ccg gat aac ggc agt gaa gtg tgg tta aaa ctg gaa       396
Gln Arg Met Gly Pro Asp Asn Gly Ser Glu Val Trp Leu Lys Leu Glu
            20                  25                  30
```

```
ggc aat aac ccg gca ggt tcg gtg aaa gat cgt gcg gca ctt tcg atg      444
Gly Asn Asn Pro Ala Gly Ser Val Lys Asp Arg Ala Ala Leu Ser Met
        35                  40                  45

atc gtc gag gcg gaa aag cgc ggg gaa att aaa ccg ggt gat gtc tta      492
Ile Val Glu Ala Glu Lys Arg Gly Glu Ile Lys Pro Gly Asp Val Leu
    50                  55                  60

atc gaa gcc acc agt ggt aac acc ggc att gcg ctg gca atg att gcc      540
Ile Glu Ala Thr Ser Gly Asn Thr Gly Ile Ala Leu Ala Met Ile Ala
65                  70                  75                  80

gcg ctg aaa ggc tat cgc atg aaa ttg ctg atg ccc gac aac atg agc      588
Ala Leu Lys Gly Tyr Arg Met Lys Leu Leu Met Pro Asp Asn Met Ser
                85                  90                  95

cag gaa cgc cgt gcg gcg atg cgt gct tat ggt gcg gaa ctg att ctt      636
Gln Glu Arg Arg Ala Ala Met Arg Ala Tyr Gly Ala Glu Leu Ile Leu
            100                 105                 110

gtc acc aaa gag cag ggc atg gaa ggt gcg cgc gat ctg gcg ctg gag      684
Val Thr Lys Glu Gln Gly Met Glu Gly Ala Arg Asp Leu Ala Leu Glu
        115                 120                 125

atg gcg aat cgt ggc gaa gga aag ctg ctc gat cag ttc aat aat ccc      732
Met Ala Asn Arg Gly Glu Gly Lys Leu Leu Asp Gln Phe Asn Asn Pro
    130                 135                 140

gat aac cct tat gcg cat tac acc acc act ggg ccg gaa atc tgg cag      780
Asp Asn Pro Tyr Ala His Tyr Thr Thr Thr Gly Pro Glu Ile Trp Gln
145                 150                 155                 160

caa acc ggc ggg cgc atc act cat ttt gtc tcc agc atg ggg acg acc      828
Gln Thr Gly Gly Arg Ile Thr His Phe Val Ser Ser Met Gly Thr Thr
                165                 170                 175

ggc act atc acc ggc gtc tca cgc ttt atg cgc gaa caa tcc aaa ccg      876
Gly Thr Ile Thr Gly Val Ser Arg Phe Met Arg Glu Gln Ser Lys Pro
            180                 185                 190

gtg acc att gtc ggc ctg caa ccg gaa gag ggc agc agc att ccc ggc      924
Val Thr Ile Val Gly Leu Gln Pro Glu Glu Gly Ser Ser Ile Pro Gly
        195                 200                 205

att cgc cgc tgg cct acg gaa tat ctg ccg ggg att ttc aac gct tct      972
Ile Arg Arg Trp Pro Thr Glu Tyr Leu Pro Gly Ile Phe Asn Ala Ser
    210                 215                 220

ctg gtg gat gag gtg ctg gat att cat cag cgc gat gcg gaa aac acc     1020
Leu Val Asp Glu Val Leu Asp Ile His Gln Arg Asp Ala Glu Asn Thr
225                 230                 235                 240

atg cgc gaa ctg gcg gtg cgg gaa gga ata ttc tgt ggc gtc agc tcc     1068
Met Arg Glu Leu Ala Val Arg Glu Gly Ile Phe Cys Gly Val Ser Ser
                245                 250                 255

ggc ggc gcg gtt gcc gga gca ctg cgg gtg gca aaa gct aac cct gac     1116
Gly Gly Ala Val Ala Gly Ala Leu Arg Val Ala Lys Ala Asn Pro Asp
            260                 265                 270

gcg gtg gtg gtg gcg atc atc tgc gat cgt ggc gat cgc tac ctt tct     1164
Ala Val Val Val Ala Ile Ile Cys Asp Arg Gly Asp Arg Tyr Leu Ser
        275                 280                 285

acc ggg gtg ttt ggg gaa gag cat ttt agc cag ggg gcg ggg att taa     1212
Thr Gly Val Phe Gly Glu Glu His Phe Ser Gln Gly Ala Gly Ile
    290                 295                 300

ggattaatag catcggagac tgatgacaaa cgcaaaactg cctgatgcgc tacgcttatc   1272

aggcctacaa ggtttctgca atatattgaa ttagcacgat tttgtaggcc ggataaggcg   1332

tttacgccgc atccggcata aacaaagcgc acttttttaa cagttgttgc tgccgacaaa   1392

tgcagtattt aattttcgtg aggaaacgcc gtaaggtcat caatcatttt ttgaagtatt   1452

ggtgagtcct gaccgtcacc ccattgaaga atttttgcgg taagctgatg acgcgctagt   1512
```

<210> SEQ ID NO 19
<211> LENGTH: 303
<212> TYPE: PRT
<213> ORGANISM: Artificial Sequence
<220> FEATURE:
<223> OTHER INFORMATION: Synthetic Construct

<400> SEQUENCE: 19

```
Val Ser Thr Leu Glu Gln Thr Ile Gly Asn Thr Pro Leu Val Lys Leu
1               5                   10                  15

Gln Arg Met Gly Pro Asp Asn Gly Ser Glu Val Trp Leu Lys Leu Glu
            20                  25                  30

Gly Asn Asn Pro Ala Gly Ser Val Lys Asp Arg Ala Ala Leu Ser Met
        35                  40                  45

Ile Val Glu Ala Glu Lys Arg Gly Glu Ile Lys Pro Gly Asp Val Leu
    50                  55                  60

Ile Glu Ala Thr Ser Gly Asn Thr Gly Ile Ala Leu Ala Met Ile Ala
65                  70                  75                  80

Ala Leu Lys Gly Tyr Arg Met Lys Leu Leu Met Pro Asp Asn Met Ser
                85                  90                  95

Gln Glu Arg Arg Ala Ala Met Arg Ala Tyr Gly Ala Glu Leu Ile Leu
            100                 105                 110

Val Thr Lys Glu Gln Gly Met Glu Gly Ala Arg Asp Leu Ala Leu Glu
        115                 120                 125

Met Ala Asn Arg Gly Glu Gly Lys Leu Leu Asp Gln Phe Asn Asn Pro
    130                 135                 140

Asp Asn Pro Tyr Ala His Tyr Thr Thr Thr Gly Pro Glu Ile Trp Gln
145                 150                 155                 160

Gln Thr Gly Gly Arg Ile Thr His Phe Val Ser Ser Met Gly Thr Thr
                165                 170                 175

Gly Thr Ile Thr Gly Val Ser Arg Phe Met Arg Glu Gln Ser Lys Pro
            180                 185                 190

Val Thr Ile Val Gly Leu Gln Pro Glu Glu Gly Ser Ser Ile Pro Gly
        195                 200                 205

Ile Arg Arg Trp Pro Thr Glu Tyr Leu Pro Gly Ile Phe Asn Ala Ser
    210                 215                 220

Leu Val Asp Glu Val Leu Asp Ile His Gln Arg Asp Ala Glu Asn Thr
225                 230                 235                 240

Met Arg Glu Leu Ala Val Arg Glu Gly Ile Phe Cys Gly Val Ser Ser
                245                 250                 255

Gly Gly Ala Val Ala Gly Ala Leu Arg Val Ala Lys Ala Asn Pro Asp
            260                 265                 270

Ala Val Val Val Ala Ile Ile Cys Asp Arg Gly Asp Arg Tyr Leu Ser
        275                 280                 285

Thr Gly Val Phe Gly Glu Glu His Phe Ser Gln Gly Ala Gly Ile
    290                 295                 300
```

<210> SEQ ID NO 20
<211> LENGTH: 36
<212> TYPE: DNA
<213> ORGANISM: Artificial Sequence
<220> FEATURE:
<223> OTHER INFORMATION: primer P1

<400> SEQUENCE: 20

```
agctgagtcg acccccagga aaaattggtt aataac                              36
```

<210> SEQ ID NO 21
<211> LENGTH: 33
<212> TYPE: DNA
<213> ORGANISM: Artificial Sequence
<220> FEATURE:
<223> OTHER INFORMATION: primer P2

<400> SEQUENCE: 21
agctgagcat gcttccaact gcgctaatga cgc 33

<210> SEQ ID NO 22
<211> LENGTH: 33
<212> TYPE: DNA
<213> ORGANISM: Artificial Sequence
<220> FEATURE:
<223> OTHER INFORMATION: primer P3

<400> SEQUENCE: 22
agctgatcta gaaaacagaa tttgcctggc ggc 33

<210> SEQ ID NO 23
<211> LENGTH: 33
<212> TYPE: DNA
<213> ORGANISM: Artificial Sequence
<220> FEATURE:
<223> OTHER INFORMATION: primer P4

<400> SEQUENCE: 23
agctgaggat ccaggaagag tttgtagaaa cgc 33

<210> SEQ ID NO 24
<211> LENGTH: 32
<212> TYPE: DNA
<213> ORGANISM: Artificial Sequence
<220> FEATURE:
<223> OTHER INFORMATION: primer P5

<400> SEQUENCE: 24
agctgagtcg acgtgttcgc tgaatacggg gt 32

<210> SEQ ID NO 25
<211> LENGTH: 32
<212> TYPE: DNA
<213> ORGANISM: Artificial Sequence
<220> FEATURE:
<223> OTHER INFORMATION: primer P6

<400> SEQUENCE: 25
agctgatcta gagaaagcat caggattgca gc 32

<210> SEQ ID NO 26
<211> LENGTH: 59
<212> TYPE: DNA
<213> ORGANISM: Artificial Sequence
<220> FEATURE:
<223> OTHER INFORMATION: primer P7
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:

<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 26
atcgtgaaga tcttttccag tgttnannag ggtgccttgc acggtnatna ngtcactgg 59

<210> SEQ ID NO 27
<211> LENGTH: 32
<212> TYPE: DNA
<213> ORGANISM: Artificial Sequence
<220> FEATURE:
<223> OTHER INFORMATION: primer P8
<220> FEATURE:
<221> NAME/KEY: misc_feature
<222> LOCATION: (16)..(20)
<223> OTHER INFORMATION: n is a, c, g, or t

<400> SEQUENCE: 27
tggaaaagat cttcannnnn cgctgacctg cg 32

<210> SEQ ID NO 28
<211> LENGTH: 30
<212> TYPE: DNA
<213> ORGANISM: Artificial Sequence
<220> FEATURE:
<223> OTHER INFORMATION: primer P9

<400> SEQUENCE: 28
catgccatgg tcgctgaata cggggttctg 30

<210> SEQ ID NO 29
<211> LENGTH: 27
<212> TYPE: DNA
<213> ORGANISM: Artificial Sequence
<220> FEATURE:
<223> OTHER INFORMATION: primer P10

<400> SEQUENCE: 29
aactgcagtc aggattgcag cgtcgcc 27

<210> SEQ ID NO 30
<211> LENGTH: 24
<212> TYPE: DNA
<213> ORGANISM: Artificial Sequence
<220> FEATURE:
<223> OTHER INFORMATION: primer P11

<400> SEQUENCE: 30
aaagccacgt tgtgtctcaa aatc 24

<210> SEQ ID NO 31
<211> LENGTH: 23
<212> TYPE: DNA
<213> ORGANISM: Artificial Sequence
<220> FEATURE:
<223> OTHER INFORMATION: primer P12

<400> SEQUENCE: 31
ggtgttgctg actcatacca ggc 23

<210> SEQ ID NO 32
<211> LENGTH: 21

<212> TYPE: DNA
<213> ORGANISM: Artificial Sequence
<220> FEATURE:
<223> OTHER INFORMATION: primer P13

<400> SEQUENCE: 32
gacaattaat catccggctc g 21

<210> SEQ ID NO 33
<211> LENGTH: 20
<212> TYPE: DNA
<213> ORGANISM: Artificial Sequence
<220> FEATURE:
<223> OTHER INFORMATION: primer P14

<400> SEQUENCE: 33
tttatcagac cgcttctgcg 20

<210> SEQ ID NO 34
<211> LENGTH: 60
<212> TYPE: DNA
<213> ORGANISM: Artificial Sequence
<220> FEATURE:
<223> OTHER INFORMATION: primer P15

<400> SEQUENCE: 34
tccgctcacg atttttttca tcgctggtaa ggtcatttat cccccaggaa aaattggtta 60

<210> SEQ ID NO 35
<211> LENGTH: 63
<212> TYPE: DNA
<213> ORGANISM: Artificial Sequence
<220> FEATURE:
<223> OTHER INFORMATION: primer P16

<400> SEQUENCE: 35
tttcacaccg ctcaaccgca gggcataacc ggcccttgaa gcctgctttt ttatactaag 60
ttg 63

<210> SEQ ID NO 36
<211> LENGTH: 20
<212> TYPE: DNA
<213> ORGANISM: Artificial Sequence
<220> FEATURE:
<223> OTHER INFORMATION: primer P17

<400> SEQUENCE: 36
ctttgtccct ttagtgaagg 20

<210> SEQ ID NO 37
<211> LENGTH: 44
<212> TYPE: DNA
<213> ORGANISM: Artificial Sequence
<220> FEATURE:
<223> OTHER INFORMATION: primer P18

<400> SEQUENCE: 37
agctgatcta gaagctgact cgagttaatg gcctcccaga cgac 44

<210> SEQ ID NO 38
<211> LENGTH: 33
<212> TYPE: DNA
<213> ORGANISM: Artificial Sequence
<220> FEATURE:
<223> OTHER INFORMATION: primer P19

<400> SEQUENCE: 38
agctgagtcg acatggcaaa ggtatcactg gaa 33

<210> SEQ ID NO 39
<211> LENGTH: 34
<212> TYPE: DNA
<213> ORGANISM: Artificial Sequence
<220> FEATURE:
<223> OTHER INFORMATION: primer P20

<400> SEQUENCE: 39
gagaacgccc gggcgggctt cgtgaatatg cagc 34

<210> SEQ ID NO 40
<211> LENGTH: 32
<212> TYPE: DNA
<213> ORGANISM: Artificial Sequence
<220> FEATURE:
<223> OTHER INFORMATION: primer P21

<400> SEQUENCE: 40
agctgatcta gacgtgggat cagtaaagca gg 32

<210> SEQ ID NO 41
<211> LENGTH: 22
<212> TYPE: DNA
<213> ORGANISM: Artificial Sequence
<220> FEATURE:
<223> OTHER INFORMATION: primer P22

<400> SEQUENCE: 41
aaaaccgccc gggcgttctc ac 22

<210> SEQ ID NO 42
<211> LENGTH: 43
<212> TYPE: DNA
<213> ORGANISM: Artificial Sequence
<220> FEATURE:
<223> OTHER INFORMATION: primer P23

<400> SEQUENCE: 42
agctgaaagc ttgcatgcac gcgtggcgat ctggcctgac tgc 43

<210> SEQ ID NO 43
<211> LENGTH: 39
<212> TYPE: DNA
<213> ORGANISM: Artificial Sequence
<220> FEATURE:
<223> OTHER INFORMATION: primer P24

<400> SEQUENCE: 43
agctgagtcg accccgtggt ggcaaccttt aaaaaactg 39

<210> SEQ ID NO 44
<211> LENGTH: 39
<212> TYPE: DNA
<213> ORGANISM: Artificial Sequence
<220> FEATURE:
<223> OTHER INFORMATION: primer P25
<220> FEATURE:
<221> NAME/KEY: misc_feature
<222> LOCATION: (13)..(15)
<223> OTHER INFORMATION: n is a, c, g, or t

<400> SEQUENCE: 44
agctgagtcg acnnngtggt ggcaaccttt aaaaaactg 39

<210> SEQ ID NO 45
<211> LENGTH: 35
<212> TYPE: DNA
<213> ORGANISM: Artificial Sequence
<220> FEATURE:
<223> OTHER INFORMATION: primer P26

<400> SEQUENCE: 45
agctgagtcg acgtgagtac attagaacaa acaat 35

<210> SEQ ID NO 46
<211> LENGTH: 33
<212> TYPE: DNA
<213> ORGANISM: Artificial Sequence
<220> FEATURE:
<223> OTHER INFORMATION: primer P27

<400> SEQUENCE: 46
agctgatcta gaagtctccg atgctattaa tcc 33

<210> SEQ ID NO 47
<211> LENGTH: 32
<212> TYPE: DNA
<213> ORGANISM: Artificial Sequence
<220> FEATURE:
<223> OTHER INFORMATION: primer P28

<400> SEQUENCE: 47
cgataaactg tacgaaagac gacacataga ac 32

<210> SEQ ID NO 48
<211> LENGTH: 25
<212> TYPE: DNA
<213> ORGANISM: Artificial Sequence
<220> FEATURE:
<223> OTHER INFORMATION: primer P29

<400> SEQUENCE: 48
cgcggatcca gtggtcattt agtgc 25

<210> SEQ ID NO 49
<211> LENGTH: 28
<212> TYPE: DNA
<213> ORGANISM: Artificial Sequence
<220> FEATURE:
<223> OTHER INFORMATION: primer P30

<400> SEQUENCE: 49
cgcggatcct gtgggatttg aagcatcc 28

<210> SEQ ID NO 50
<211> LENGTH: 32
<212> TYPE: DNA
<213> ORGANISM: Artificial Sequence
<220> FEATURE:
<223> OTHER INFORMATION: primer P31

<400> SEQUENCE: 50
aagtcgacgt gttcgctgaa tacggggttc tg 32

<210> SEQ ID NO 51
<211> LENGTH: 27
<212> TYPE: DNA
<213> ORGANISM: Artificial Sequence
<220> FEATURE:

```
<223> OTHER INFORMATION: primer P32

<400> SEQUENCE: 51

aatctagatc aggattgcag cgtcgcc                              27


<210> SEQ ID NO 52
<211> LENGTH: 20
<212> TYPE: DNA
<213> ORGANISM: Artificial Sequence
<220> FEATURE:
<223> OTHER INFORMATION: primer P33

<400> SEQUENCE: 52

aaacgtgagg aaatacctgg                                      20


<210> SEQ ID NO 53
<211> LENGTH: 32
<212> TYPE: DNA
<213> ORGANISM: Artificial Sequence
<220> FEATURE:
<223> OTHER INFORMATION: primer P34
<220> FEATURE:
<221> NAME/KEY: misc_feature
<222> LOCATION: (17)..(19)
<223> OTHER INFORMATION: n is a, c, g, or t

<400> SEQUENCE: 53

cgataaactg tacgaannnc gacacataga ac                        32
```